US008765182B2

(12) United States Patent
Day et al.

(10) Patent No.: US 8,765,182 B2
(45) Date of Patent: Jul. 1, 2014

(54) MICROSPHERES

(75) Inventors: Richard Michael Day, London (GB); Jonny Blaker, Bucks (GB)

(73) Assignee: UCL Business PLC, London (GB)

( * ) Notice: Subject to any disclaimer, the term of this patent is extended or adjusted under 35 U.S.C. 154(b) by 316 days.

(21) Appl. No.: 12/665,865

(22) PCT Filed: Jun. 20, 2008

(86) PCT No.: PCT/GB2008/002122
§ 371 (c)(1),
(2), (4) Date: Jun. 8, 2010

(87) PCT Pub. No.: WO2008/155558
PCT Pub. Date: Dec. 24, 2008

(65) Prior Publication Data
US 2010/0247663 A1    Sep. 30, 2010

(30) Foreign Application Priority Data
Jun. 20, 2007  (GB) .................................. 0711952.2

(51) Int. Cl.
A61K 9/14    (2006.01)
A61K 9/19    (2006.01)
A61K 9/50    (2006.01)
A61K 9/16    (2006.01)

(52) U.S. Cl.
CPC ... *A61K 9/19* (2013.01); *A61K 9/50* (2013.01); *A61K 9/1682* (2013.01)
USPC .......................................................... 424/489

(58) Field of Classification Search
None
See application file for complete search history.

(56) References Cited

U.S. PATENT DOCUMENTS

| 4,743,545 | A  | * | 5/1988 | Torobin .......................... 435/41 |
| 5,047,180 | A  | * | 9/1991 | Steiner et al. ...................... 264/5 |
| 5,853,698 | A  | * | 12/1998 | Straub et al. ................. 424/9.52 |
| 6,713,083 | B1 |   | 3/2004 | McGregor |
| 7,005,118 | B2 | * | 2/2006 | Terres Rojas et al. ........ 423/702 |
| 2003/0157030 | A1 | * | 8/2003 | Davis et al. .................... 424/46 |
| 2006/0154067 | A1 |   | 7/2006 | Cooper et al. |

FOREIGN PATENT DOCUMENTS

EP  0303259 A2  2/1989
GB  2399084 A  9/2004

OTHER PUBLICATIONS

International Search Report, Jun. 2009.

* cited by examiner

*Primary Examiner* — Bethany Barham
(74) *Attorney, Agent, or Firm* — Banner & Witcoff, Ltd

(57) ABSTRACT

The invention relates to the production of microspheres having radial pores using thermally induced phase separation, especially microspheres for use in tissue engineering.

24 Claims, 35 Drawing Sheets

- • - PLGA Spheres
- ♦ Media + bugs
- ◊ Silver media (2h exposure to +Ag spheres)
- —□— PLGA with PG minus Ag
- * PLGA with PG plus 5% spheres floating
- —▵— PLGA with PG plus 5%Ag
- ▲ PLGA with PG minus Ag 5 spheres floating (a) Control TIPS Microspheres 1wk
original mag x 25

(b) Control TIPS Microspheres 1wk
original mag x 25

(c) Control TIPS Microspheres 1wk
original mag x 200

Control TIPS Microspheres 2wks
original mag x 25

Control TIPS Microspheres 2wks
original mag x 50

Control TIPS Microspheres 6wks
original mag x 50

Control TIPS Microspheres 6wks
original mag x 100

(a) Control TIPS Microspheres 2wks
original mag x 25

(b) Control TIPS Microspheres 2wks
original mag x 100

(c) TIPS Microspheres + 10% 45S5
bioactive glass 2wks
original mag x 50

(d) TIPS Microspheres + 10% 45S5
bioactive glass 2wks
original mag x 200

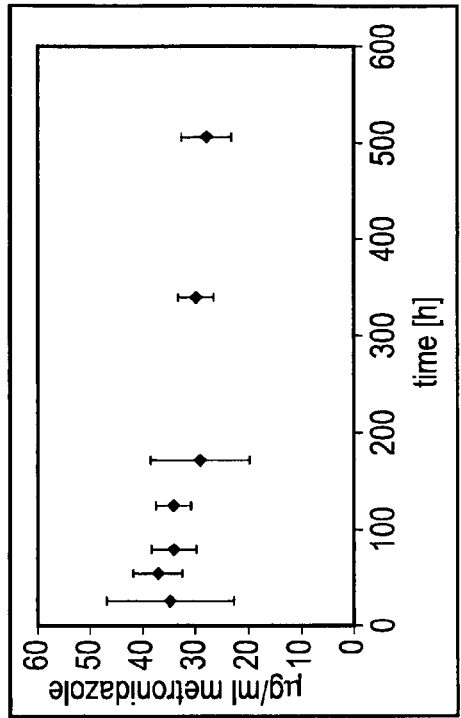
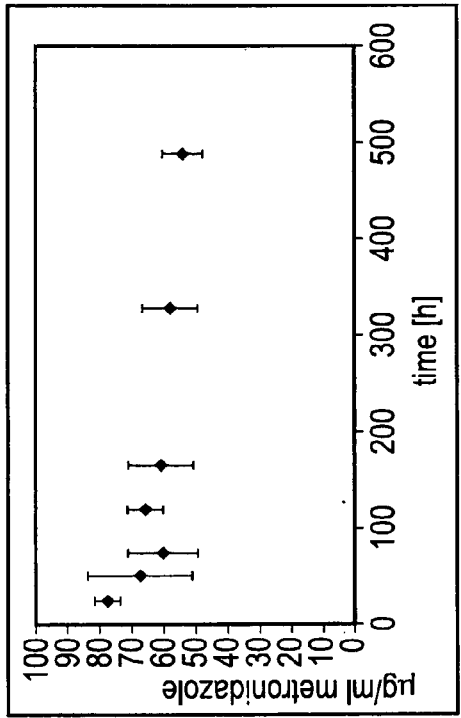
FIG. 17a
FIG. 17b
FIG. 18a
FIG. 18b

MICROSPHERES

The invention relates to the production of microspheres using thermally induced phase separation, especially microspheres for use in tissue engineering.

It is known in the prior art to use scaffolds to fill voids in damaged tissue. It is often desirable to use injectable scaffolds that are able to conform to the void to be filled because a prior knowledge of the exact shape and size of the cavity is not required and irregular shaped voids can be more easily filled. Further, for scaffolds such as microspheres it is useful for the microsphere network to have sufficiently large pores to allow the infiltration of tissue. Prior art systems include an injectable gas foaming poly-propylene fumarate-based matrix containing microspheres (Kempen D H R, Lu L, Kim C, Zhu X, Dhert W J A, Currier B L, Yaszemski M J. Controlled drug release from a novel injectable biodegradable microsphere/scaffold composite based on poly(propylene fumarate). J. Biomed. Mater. Res. 2006 (77A) 103-111), in situ formation of porosity in a matrix based on differential polymer degradation using microspheres (Shastri V P, Hildgen P, Langer R. In situ pore formation in a polymer matrix by differential polymer degradation. Biomaterials 2003 (24) 3133-3137), particulate leaching, gas foaming (Behravesh E, Jo S, Zygourakis K, Mikos A G. Synthesis of in Situ Cross-Linkable Macroporous Biodegradable Poly(propylene fumarate-co-ethylene glycol) Hydrogels. Biomacromolecules 2002 (3) 374-381) and air entraining using surfactant molecules (Sarda S, Nilsson M, Balcells M, Fernandez E. Influence of surfactant molecules as air-entraining agent for bone cement macroporosity. J. Biomed. Mater. Res. 2003 (65A) 215-221). Solid poly(lactide-co-glycolide) (PLGA) microspheres have been investigated as injectable systems for cartilage (Kang S, Jeon O, Kim B. Poly(lactic-co-glycolic acid) microspheres as an injectable scaffold for cartilage tissue engineering. Tissue Engineering 2005 11(3/4) 438-447) and adipose tissue engineering (Choi Y S, Park S, Suh H. Adipose tissue engineering using mesenchymal stem cells attached to injectable PLGA spheres. Biomaterials 2005 (26) 5855-5863).

Biodegradable microspheres may also be useful for the delivery and controlled release of bioactive compounds such as therapeutics, proteins and nucleic acids. Encapsulation of such compounds allows controlled release and protection of the non-released material from degradation. This is particularly useful when the compounds have short half lives or cannot be administered orally.

Various technologies have been used for microsphere preparation (Freitas S, Merkle H P, Gander B. Microencapsulation by solvent extraction/evaporation: reviewing the state of the art of microsphere preparation process technology. J. Cont. Rel. 2005 (102) 313-332). Among these are static mixing, extrusion through needles, membranes and microfabricated microchannel devices, dripping using electrostatic forces and ultrasonic jet excitation (Freitas S, Merkle H P, Gander B. Microencapsulation by solvent extraction/evaporation: reviewing the state of the art of microsphere preparation process technology. J. Cont. Rel. 2005 (102) 313-332). A number of studies have investigated the preparation of biodegradable poly(lactide-co-glycolide) (PLGA) microspheres using the water/oil/water (W/O/W) double emulsion methods aimed at delivering hydrophilic and macromolecular protein and peptide drugs in a sustained manner (Park T G, Lu W, Crofts G J. Importance of in vitro experimental conduits on protein release kinetics, stability and polymer degradation in protein encapsulated poly(D,L-lactic acid-co-glycolic acid) microspheres. J. Cont. Rel. 1995 (33) 211-222, Fu K, Harrell R, Zinski K, Um C, Jaklenec A, Frazier J, Lotan N, Burke P, Klibanov A M, Langer R. A potential approach for decreasing the burst effect of protein from PLGA microspheres. J. Pharm. Sci. 2003 (92) 1582-91 and Wei G, Pettway G J, McCauley L K, Ma X P. The release profiles and bioactivity of parathyroid hormone from poly(lactic-co-glycolic acid) microspheres. Biomaterials 2004 (25) 345-352). Sphere size and distributions are often poorly controllable with emulsion microsphere fabrication routes, with typical standard deviations of mean diameter being 25 to 50% of the target size, in addition to defect formations (such as hollow shells) (Berkland C, Kim K, Pack D W. Fabrication of PLG microspheres with precisely controlled monodisperse size distributions. J. Cont. Rel. 2001 (73) 59-74). Therefore a system capable of precise microsphere fabrication with high drug encapsulation efficacy is desirable to provide an efficient route to commercial manufacture and clinical implementation of drug-loaded microspheres. Fabrication of PLGA microspheres with precisely controlled and monodisperse size distributions has been achieved by spraying polymer-containing solutions through a nozzle with acoustic excitation to produce uniform droplets, or an annular non-solvent carrier system allowing further control of the droplet size (Berkland C, Kim K, Pack D W. Fabrication of PLG microspheres with precisely controlled monodisperse size distributions. J. Cont. Rel. 2001 (73) 59-74), which has been applied to produce uniform spheres with average diameters from ~5 to >500 Microspheres have also been formed by dropping polymer solutions containing dispersed protein particles via electrostatic forces into cold methanol (at −75° C.) for particle collection and solvent extraction (Amsden B G, Goosen M F. An examination of factors affecting the size, distribution and release characteristics of polymer microbeads made using electrostatics. J. Cont. Rel. 1997 (43) 183-196). To eliminate the initial burst and better control the release of the highly water-soluble cardiotoxic drug doxorubicin, double-walled microspheres with the drug encapsulated in the inner core have been fabricated (Tan E C, Lin R, Wang C. Fabrication of double-walled microspheres for the sustained release of doxorubicin. J. Coll. Int. Sci. 2005 (291) 135-143.) with PLLA shells and PLGA cores using the solvent evaporation technique—a modified oil-oil-water emulsion solvent evaporation technique, which involves the phase separation phenomenon of a binary composite of these two polymers.

Porous biodegradable microspheres are desirable for tissue engineering and drug delivery applications because the constituent amount of polymer is reduced compared with solid microspheres, yet the scaffold volume is kept constant and the degradation mechanism is a more predictable erosion type occurring through water hydrolysis of ester bonds. Several techniques have been applied to fabricate porous microspheres, including rapid solvent removal by introducing a temperature gradient (Jeyanthi R, Thanoo B C, Metha R C, DeLuca. Effect of solvent removal technique on the matrix characteristics of polylactide/glycolide microspheres for peptide delivery. J. Cont. Rel. 1996 (38) 235-244.), gas foaming (Kim T K, Yoon J J, Lee D S, Park T G. Gas foamed open porous biodegradable polymeric microspheres. Biomaterials 2006 (27) 152-159.), double emulsification (W/O/W) (Crofts G, Park T G. Preparation of porous and nonporous biodegradable polymeric hollow microspheres. J. Cont. Rel. 1995 (35) 91-105), and solution induced phase separation (Hong Y, Gao C, Shi Y, Shen J. Preparation of porous polylactide microspheres by emulsion-solvent evaporation based on solution induced phase separation. Polym. Adv. Technol. 2005 (16) 622-627). However many of these procedures are complicated for repeatable production, and with some the microspheres may still receive prolonged exposure to an aqueous continuous phase. Thermally induced phase separation (TIPS) has been applied to generate highly porous foams as monoliths (Nam Y S and Park T G. Porous biodegradable polymeric scaffolds prepared by thermally induced phase separation. J. Biomed. Mater. Res. 1999 (47) 8-17), but to date this process has not be applied to the fabrication of porous microspheres.

U.S. Pat. No. 4,837,285 describes the formation of beads from collagen. In that method, collagen is dispersed in acetic acid. Droplets of the beads resulting from the dispersed system are introduced into liquid nitrogen and then lyophilised to produce beads. The beads contain irregular pore with no consistency as to pave direction, probably due to the fact that the collagen is dispersed in the acetic acid, rather than dissolved therein.

The inventors have developed a new strategy for producing microspheres using thermally induced phase separation (TIPS). The microspheres produced using the methods developed by the inventors are structurally different to presently known microspheres. The structural differences result in improved characteristics such as mechanical strength and the ability to select pore size and whether or not the microspheres are covered with a skin.

According to the invention there is provided a microsphere having radial pores.

The term microsphere refers to one of a preparation of uniform substantially spherical particles. The term is well known in the art.

The microspheres of the invention contain a number of radial pores. This means that the pores extend from the central part of the microsphere towards the surface, preferably substantially parallel to the radii of the microsphere. The pores are preferably tubular and interconnected. The radial pores provide the microspheres with a level of mechanical strength not previously seen in microspheres. This means the spheres may be used without being cross linked together.

The term microsphere as used herein is intended to encompass nanospheres, microspheres and also larger microsphere-like particles. Nanospheres generally have a diameter of 100 nm or less. Preferably, however, the term microsphere as used herein does not encompass nanospheres. Such a microsphere is preferably about 10 to 2000 µm in diameter as characterised by electron microscopy, such as scanning electron microscopy. A microsphere-like particle is a spherical particle which has similar characteristics to a microsphere except that, in this context, it is larger than 1000 µm in diameter. The diameter of the microsphere may be selected according to the intended use. For example, the microsphere may be around 10 to 20 µm in diameter for use in inhalation or drug delivery or may be around 200 to 600 µm in diameter, especially between 300 and 400 µm in diameter for tissue engineering. The microspheres are preferably less than 300 µm in diameter, more preferably less than 250 µm in diameter.

The pore size may also be selected according to the intended use. The pores are preferably between 1 and 100 µm in diameter, more preferably between 1 and 70 µm, more preferably between 1 and 50 µm, even more preferably between 1 and 30 µm. Further, the pores are preferably regular in size, that is to say the pores are preferably substantially the same diameter. Porous microspheres produced according to the invention have good mechanical strength due to the nature of the pores. Preferably the microspheres have "mechanical resistance" of 10 kPa or above, more preferably 100 kPa or above.

The microsphere may include a skin region at the surface or may be skinless. The surface topography of the skin can be controlled by the processing parameters. For example microspheres with a smooth surface, peppered with pores of 1 to 5 µm with a chevron like pattern due to the solvent crystallisation at the exterior of the drop are produced using neat PLGA for the TIPS process, whereas emulsion TIPS microspheres produced using water mixed into the polymer solution produce a rugose, interconnected and disrupted surface, which is of similar structure to the interior.

The microsphere is produced from polymers. Any polymer may be used, but the polymer is preferably pharmaceutically acceptable and must be completely soluble in a solvent. The polymer may be degradable or non-degradable. It may be synthetic or non-synthetic. In one embodiment, a combination of polymers can be used, for example, a synthetic polymer used in combination with a non-synthetic polymer. Example polymers include poly($\alpha$-hydroxyester), polyanhydrides, polyorthoesters, polyphosphazines, polypropylene fumarate, poly(propylene-fumarate-co-ethylene glycol), polyethylene oxide, polyhydroxybutyrate (PHB) and polyhydroxyvalerate (PHV). Co-polymers of two or more polymers may also be used, especially of PHB and PHV. Others include poly($\alpha$-hydroxyester)-co-PEG copolymer, or co-polymers including a Pegylated drug. Natural polymers that may be used include fibrin. Preferably the polymer is not chitosan.

The microspheres may contain encapsulated additives, such as, for example, glasses, glass-ceramics, or ceramics containing, for example $NaH_2PO_4$, $CaCO_3$, $P_2O_5$, and $Ag_2SO_4$; proteins or peptides such as antibodies or fragments thereof; nucleic acids; and therapeutic agents.

The microsphere is preferably produced by thermally induced phase separation. In particular, the microsphere may be produced by the following methods.

In particular, the inventors have designed methods for producing the microspheres. According to the invention, there is provided a method of producing microspheres comprising the steps of:

a) dissolving a polymer in a solvent;
b) quenching droplets of the solution in a quenching fluid; and
c) freeze-drying the resulting spheres.

The polymer is preferably as defined above.

Any appropriate solvent may be used. The solvent is selected to have a higher freeze temperature higher than the temperature of the quench fluid. Example solvents include dimethylcarbonate, chloroform, acetone, dimethylchloride, tetrahydrofuran and supercritical carbon dioxide.

When supercritical carbon dioxide is used as a solvent, its primary mode of action is through plasticisation of the polymer although when the solution is quenched the supercritical carbon dioxide will separate from the polymer in a similar way to other solvents creating microspheres with radial pores.

The quenching fluid may be a liquid or a gas. It must have a temperature below that of the freezing temperature of the solvent. Example quenching fluids include liquid nitrogen, liquid oxygen, liquid $CO_2$, freon, water, ethanol, methanol.

The solution may be introduced into the quenching fluid using any appropriate method. For example, droplets may be produced using a syringe or a vibrating needle. Alternatively, the solution may be sprayed through an atomiser, using, for example, an aerosol propelled or pumped system, or pulled into the quenching solution using electrostatic force or coaxial air stream.

The method may additionally comprise sonicating the solution. This may be in the presence of water which can act to form an emulsion. This allows smaller spheres to be produced.

Further provided is a method of producing a microsphere comprising the steps of:
a) dissolving a polymer in a solvent;
b) agitating or homogenising the solution in water;
c) rapidly freezing the solution; and
d) freeze-drying the resulting spheres.

The methods may additionally comprise the step of mixing the polymer with an agent to be encapsulated within the microsphere. Such agents may include, for example, glasses, glass-ceramics, or ceramics containing, for example $NaH_2PO_4$, $CaCO_3$, $P_2O_5$, $Ag_2SO_4$; proteins or peptides such as antibodies or fragments thereof; nucleic acids; and therapeutic agents.

The pore structure may be altered by including other phases in the solution, such as water, or by combining with a third leachable phase such as ice microparticulates, salt/sucrose/paraffin wax/rapidly degrading polymer, or by using gas-foaming reagents, such as citric acid and sodium bicarbonate. The polymer/solvent ratio and freeze rate can be adjusted to control pore structure. Also by combining solvents (i.e., miscible/non-miscible solvents) with the polymer, voids may be introduced on freeze-drying, thereby controlling pore structure. Accordingly, the method may include the step of introducing a further phase into the solution, the phase being, for example, a further solvent, a leachable phase or a gas foaming reagent.

The pores are typically interconnected and tubular. In particular, the pores are radial, that is to say extending from close to the centre of the microsphere to the surface.

Also provided is a microsphere produced by the methods of the invention.

The microspheres may be used in various therapeutic methods. Accordingly, there is provided a microsphere according to the invention for use in therapy.

In particular, the microspheres may be used to fill cavities and wounds such as fistulas, abscesses, bed sores and ulcers, especially of the leg or foot. They may also be used in tissue augmentation for plastic and reconstructive surgery. The microspheres may also be used in bone filling. As the pore structures can be tailored carefully, it is possible to mimic the pore differences between cortical and cancellous bone. The radial pores of the microspheres give optimal mechanical properties for the amount of polymer used. This means that a patient may be able to bear weight on the wound or other area to which the microspheres have been added. Mechanical stimulation of this nature may promote wound healing.

Further, as discussed above, the microspheres are suitable carrier for bioactive additives, such as glasses and glass-ceramics, allowing delivery of bioactive agents to wounds, bones and surgical sites in a controlled manner. The microspheres show high encapsulation efficiency, whilst maintaining pore interconnectivity. The microspheres show such high levels of encapsulation because there is no need to wash the microspheres following freeze drying. Hence, there is reduced leaching of the encapsulated agents.

Accordingly, there is provided the use of a microsphere according to the invention in the preparation of a scaffold or the preparation of a medicament for the treatment of a wound.

The term wound is herein used to mean an external or internal wound, such as a fistula, abscess, bed sore, ulcer and any other wound requiring tissue augmentation.

The type of polymer (e.g. permanent or degradable, natural or synthetic), porosity, mechanical strength and size may be selected depending on the type of tissue at the wound site. The microspheres may contain additives for delivery to the wound. For example, for fistula repair in Crohn's disease metronidazole or anti-TNF-α antibody may be added to the microspheres. These may be incorporated during the fabrication process or loaded afterwards. The latter would enable dosages to be tailored for individual patients.

Also provided is a method of treating a wound, comprising filling the wound with microspheres according to the invention.

The invention will now be described in detail, by way of example only, with reference to the drawings, in which.

Figure 3:
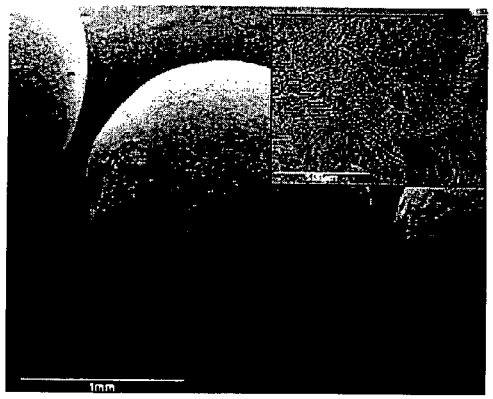
Figure 4A:
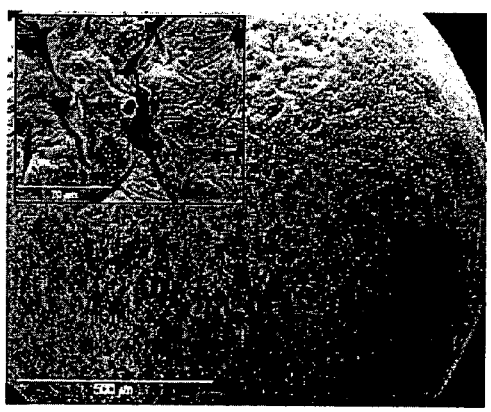

FIG. 3 is a low magnification SEM of the well formed PLGA TIPS microspheres. The exterior of the microspheres produced from neat PLGA consists of a skin region of about 2 μm thickness with a smooth polymer surface, peppered with pores of 1 to 5 μm with a chevron like pattern due to the solvent crystallisation at the exterior of the drop, as shown in the inset at higher magnification FIG. 4a shows an emulsion TIPS microsphere produced using water to polymer solution ratio of 0.25:1 showing a rugose and disrupted surface as shown by the inset at high magnification.

Figure 4B:
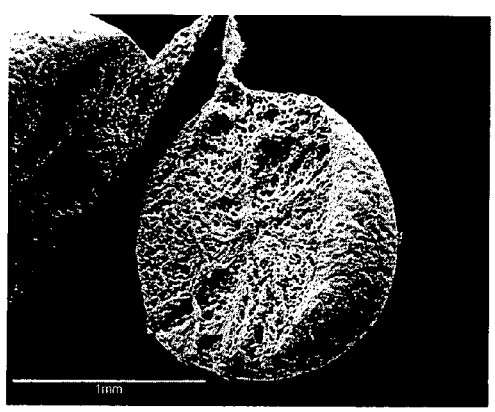

FIG. 4b shows a cross section of an emulsion TIPS microsphere produced using a water to polymer solution ratio of 0.5:1 showing a more open pore structure with large number of interconnected spherical pores of ~50 to 70 μm diameter in a fibre-like network.

Figure 4C:
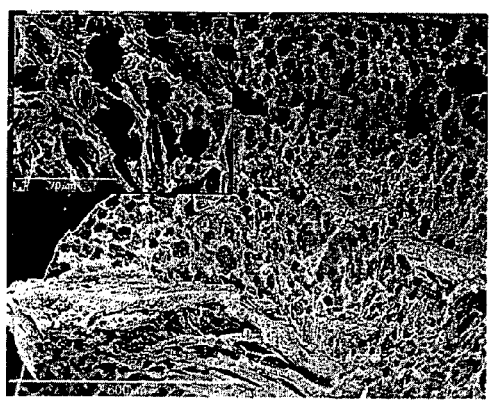

FIG. 4c shows a cross section of an emulsion TIPS microsphere produced using a water to polymer solution ratio of 0.25:1, which in comparison to the PLGA/DMC TIPS spheres shows a more open pore structure with less channel-like pores and a large number of interconnected spherical pores of ~50 μm diameter.

Figure 5:
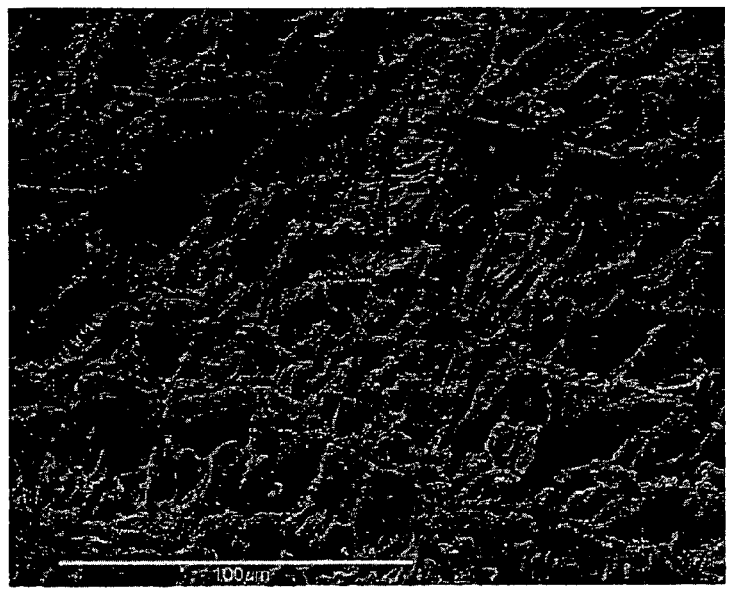

FIG. 5 is a SEM image of a cross section of a microsphere made in accordance with the invention containing anti-microbial bioactive phosphate glass (jagged shards).

Figure 6A:
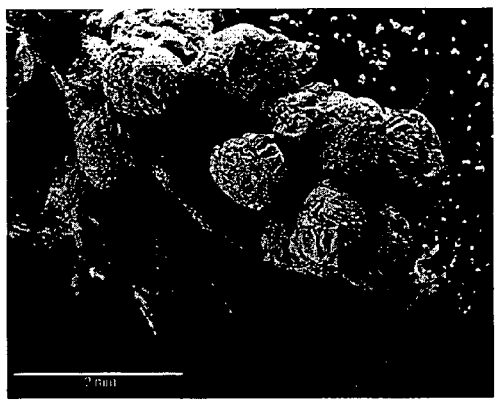

FIG. 6a is a low magnification SEM of emulsion TIPS spheres produced using water to polymer solution ratio of 1:1. The spheres are fragile and contain many smaller TIPS microspheres.

Figure 6B:

FIG. 6b is a high magnification SEM of emulsion TIPS microspheres produced using water to polymer solution ratio of 1:1. The smaller microspheres were present inside the larger fragile spheres produced during TIPS processing.

Figure 6C:
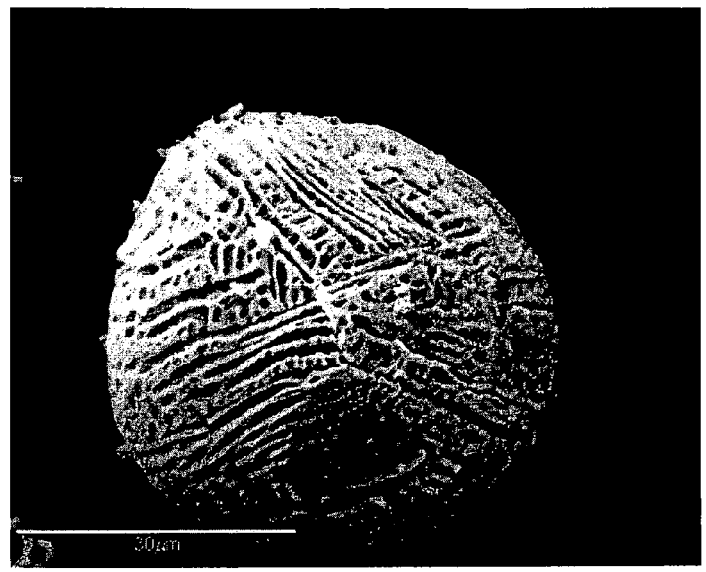

FIG. 6c is a high magnification SEM showing the open porous surface of an emulsion TIPS microsphere produced using water to polymer solution ratio of 1:1.

Figure 7:
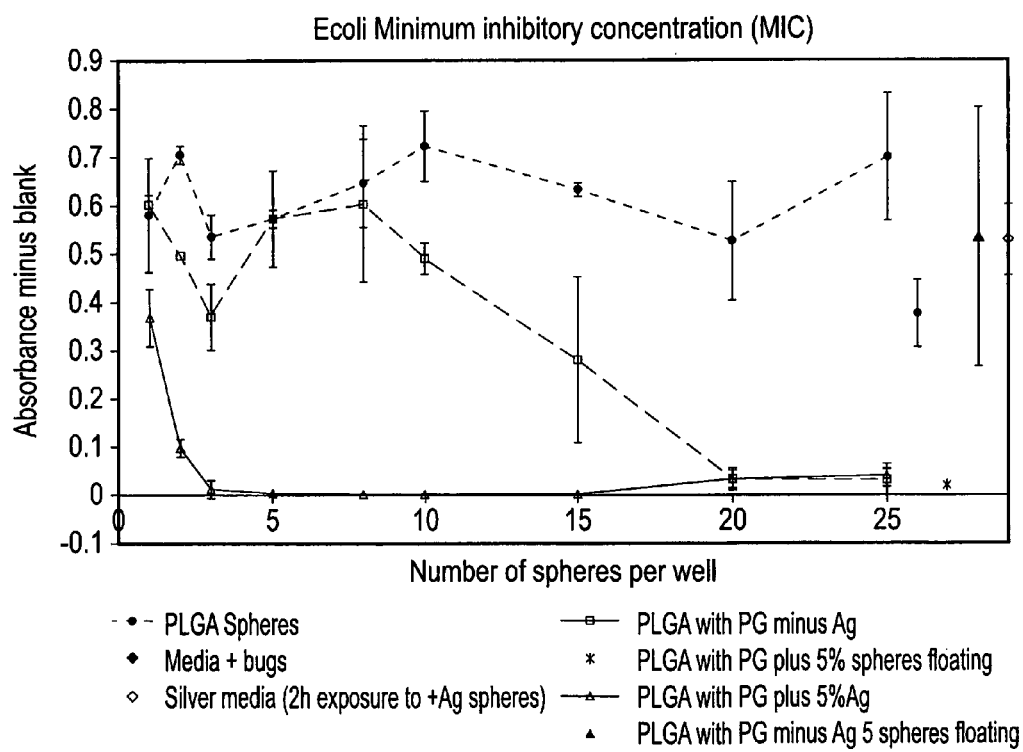

FIG. 7 shows the turbidity determination of media including the microspheres shown in FIG. 5 to indicate bacterial inhibition.

Figure 8:
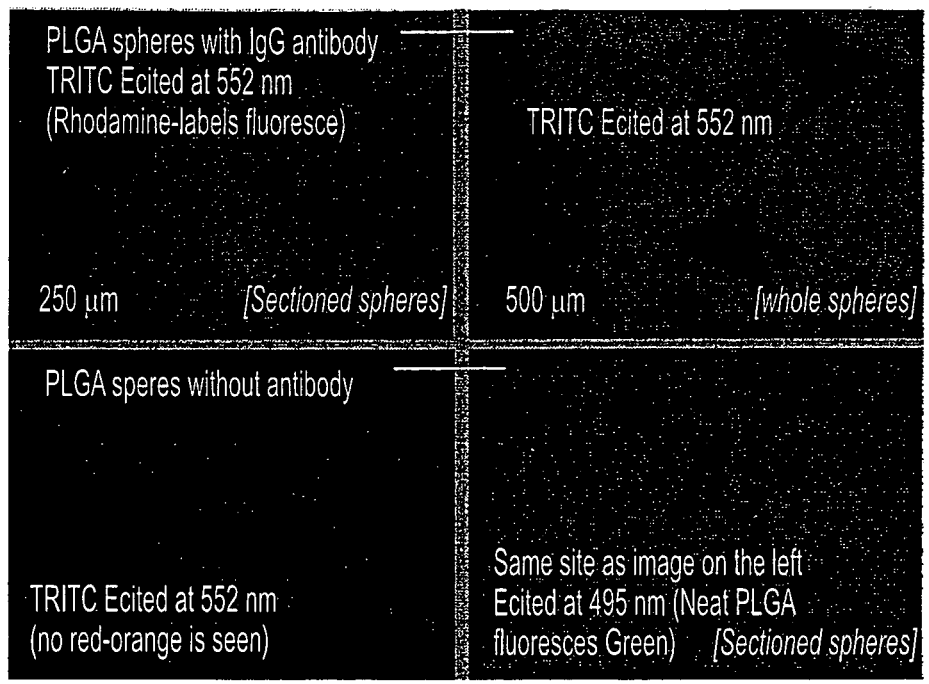

FIG. 8 shows PGLA microspheres labelled with antibody.

Figure 9:
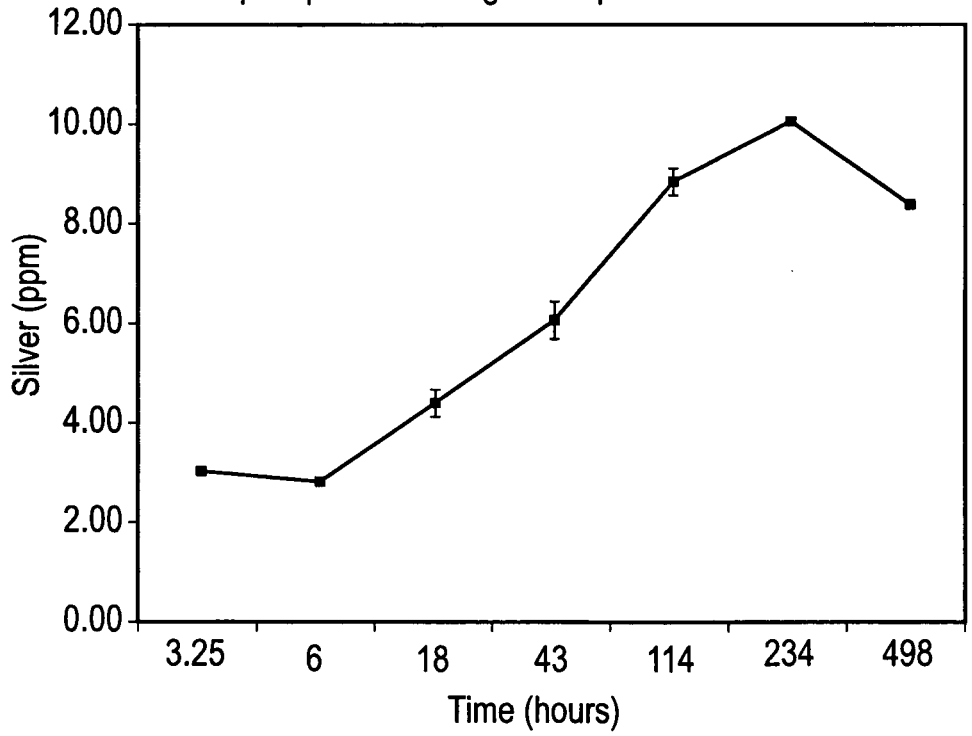

FIG. 9 shows the dissolution of silver from microspheres containing silver doped-phosphate glass.

Figure 10:
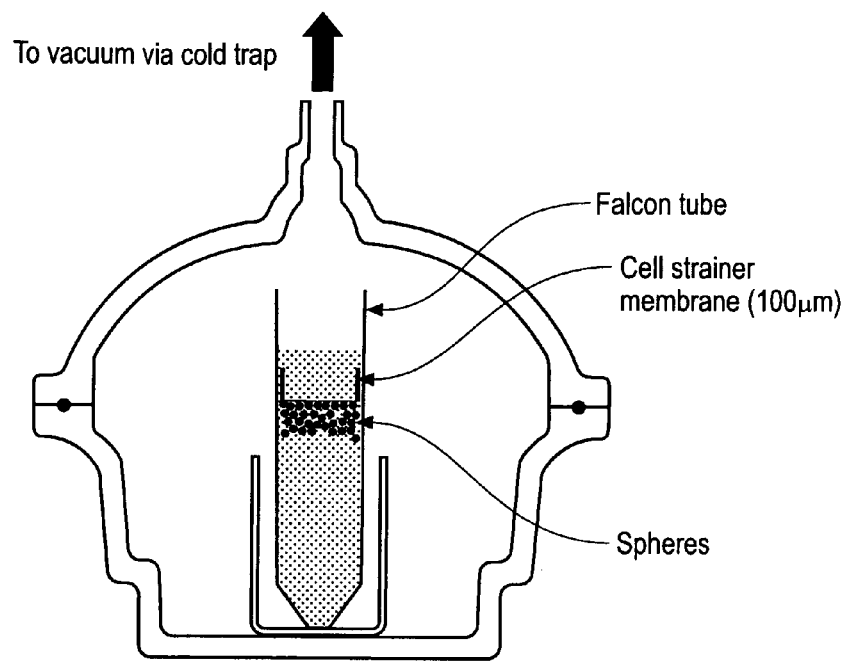
Figure 11:
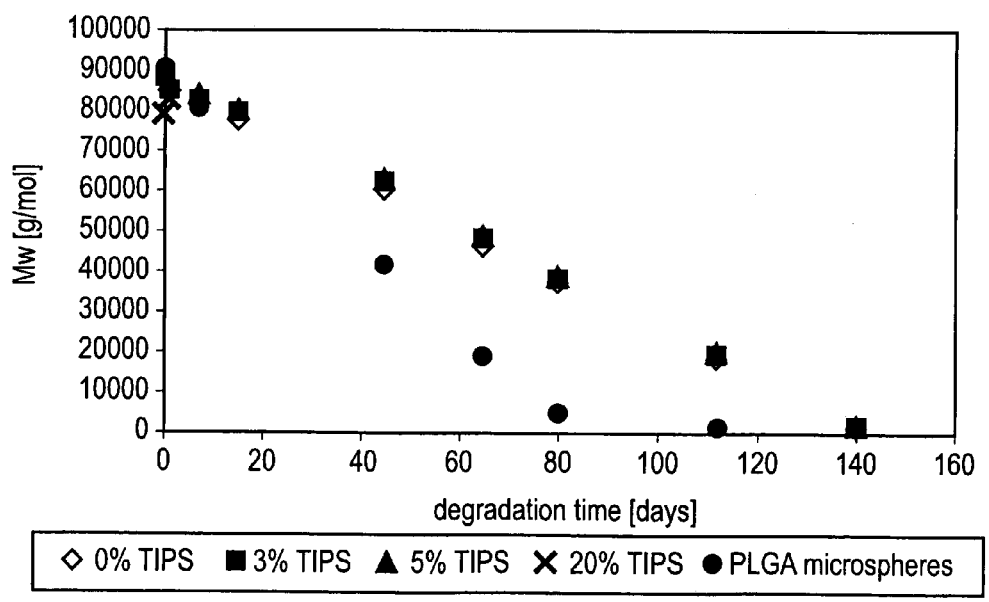

FIG. 10 shows a schematic representation of the rig used to sink the spheres and fully infuse them with test fluids FIG. 11 shows the change in weight average molecular weight (Mw) as a function of degradation time in PBS at 37° C.

Figure 12:
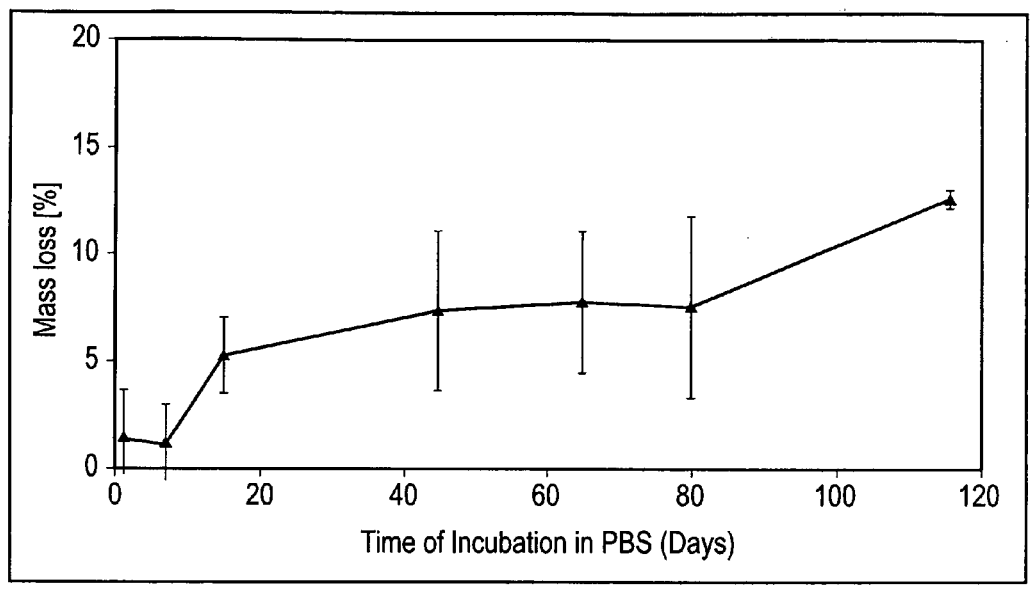

FIG. 12 shows mass loss for microspheres incubated in PBS.

Figure 13:
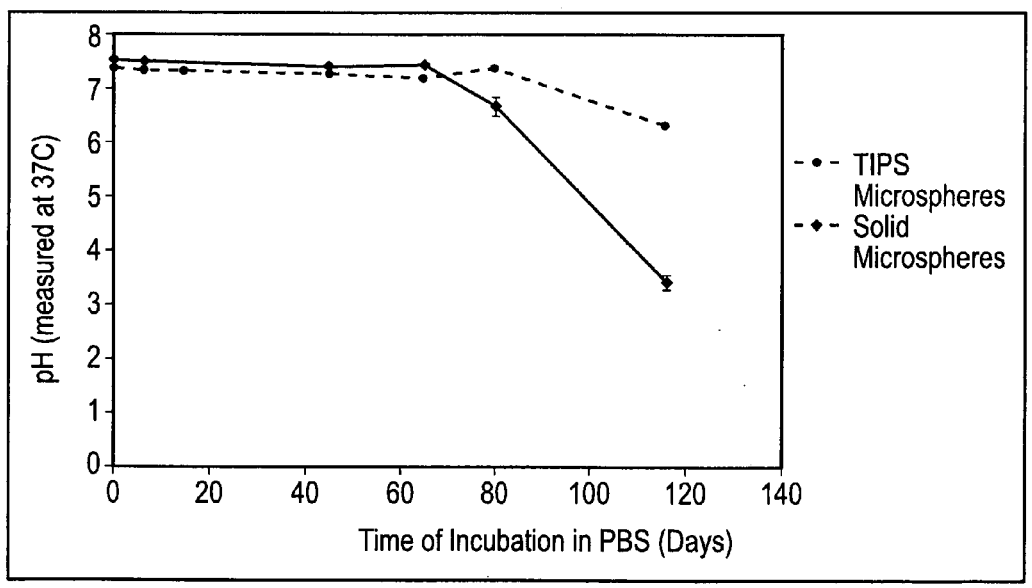

FIG. 13 shows the change in pH for prior art spheres and microspheres according to the invention following incubation in PBS.

Figure 14:
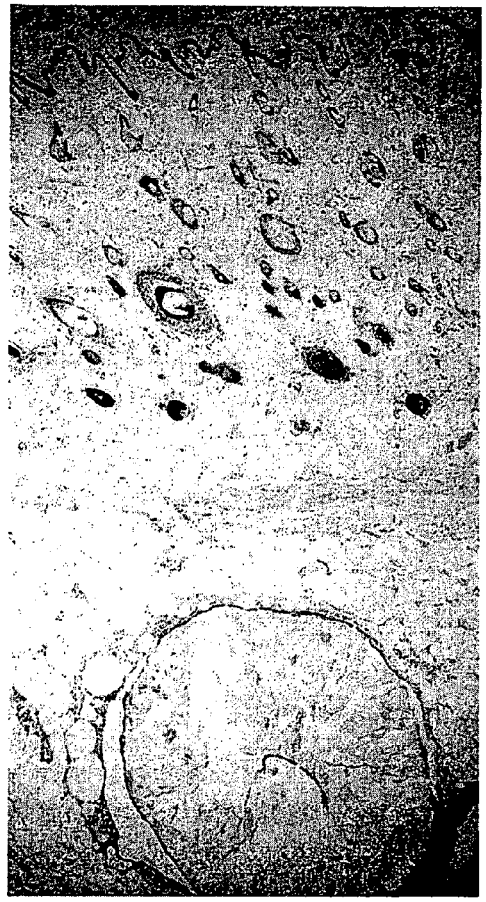
Figure 14:
Figure 14:
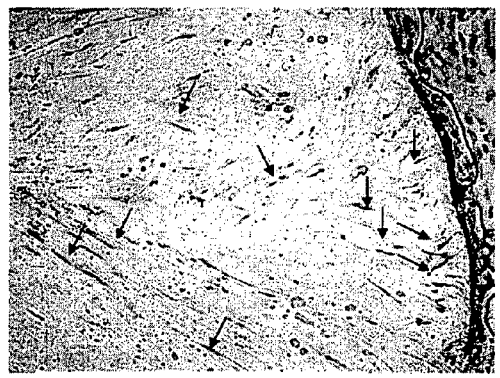
Figure 15:
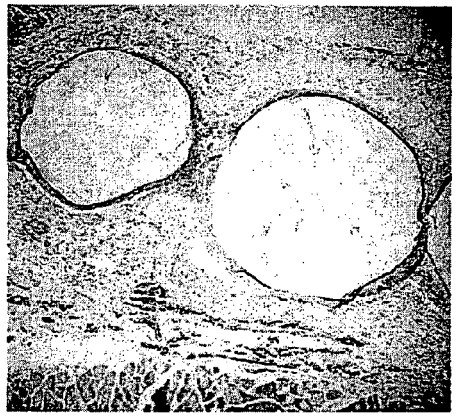
Figure 15:
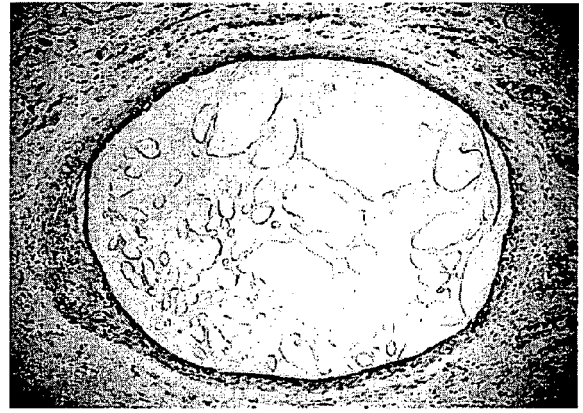
Figure 15:
Figure 15:
Figure 16:
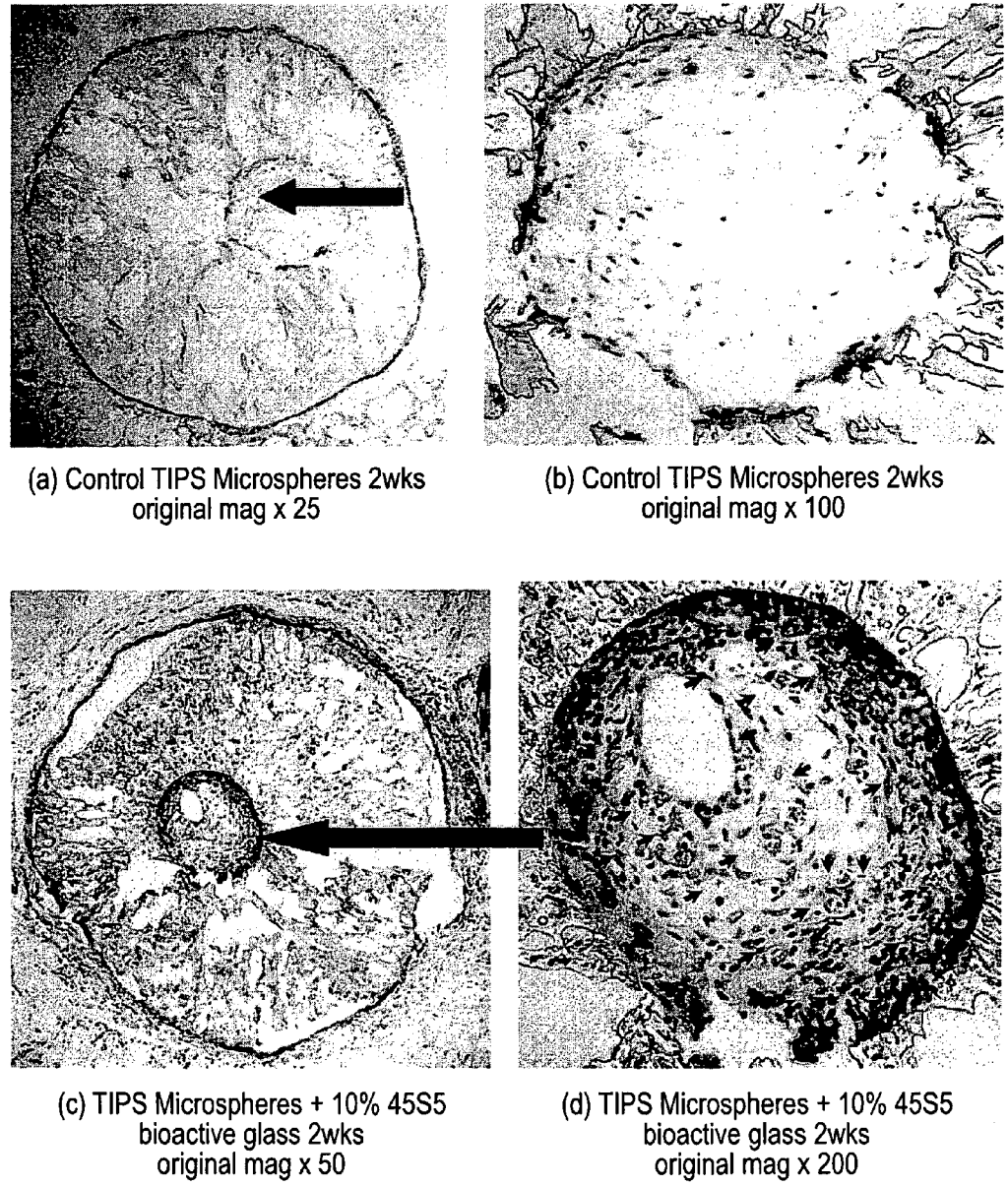

FIGS. 14, 15 and 16 show microspheres following implantation into tissue.

FIGS. 17 and 18 show metronidazole release from microspheres containing 1.25% (w/w) and 2.5% (w/w) metronidazole respectively.

Figure 19:

FIG. 19 shows microspheres produced from fibrin using the method of the present invention.

Figure 20:
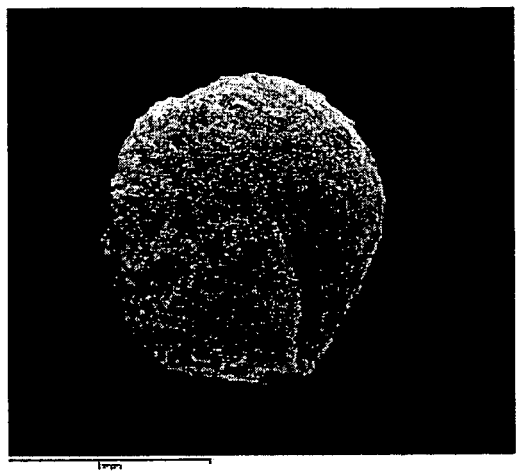
Figure 20:
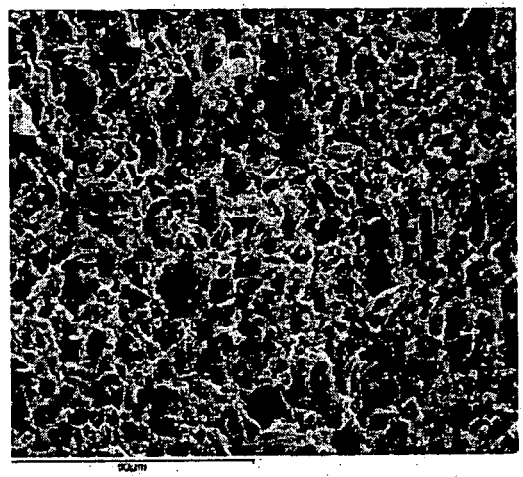
Figure 20:
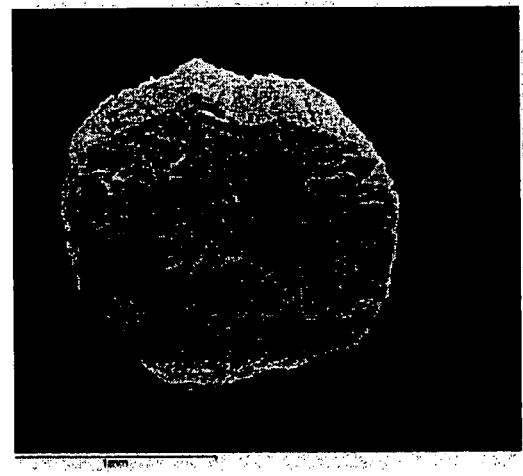
Figure 20:
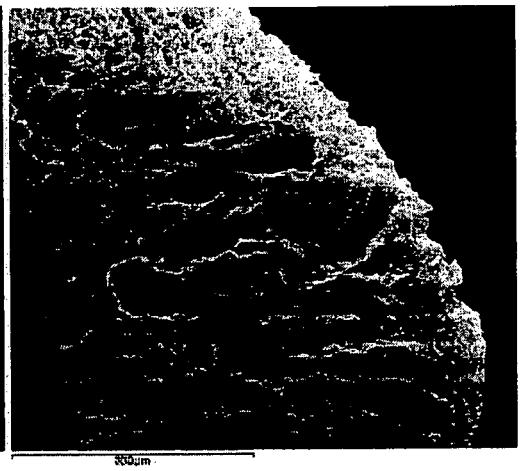

FIG. 20 shows microspheres produced from collagen using the method of U.S. Pat. No. 4,837,285, as a comparative example.

Figure 21:
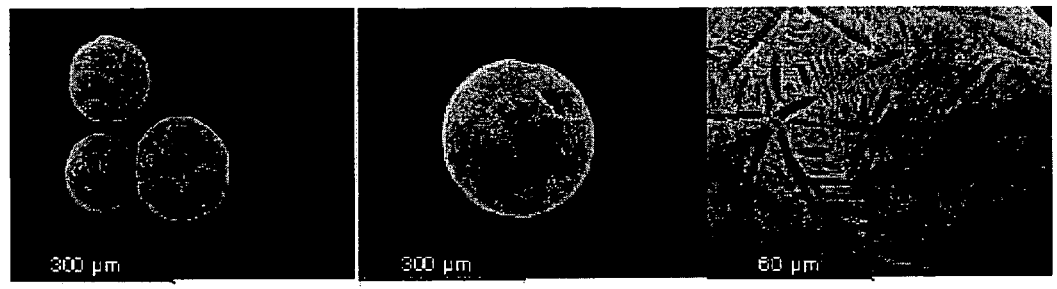

FIG. 21 is a scanning electron micrograph of TIPS microspheres produced using the encapsulation unit. The large void opening onto the surface is still present in the microspheres together with the characteristic chevron patterning.

Figure 22:
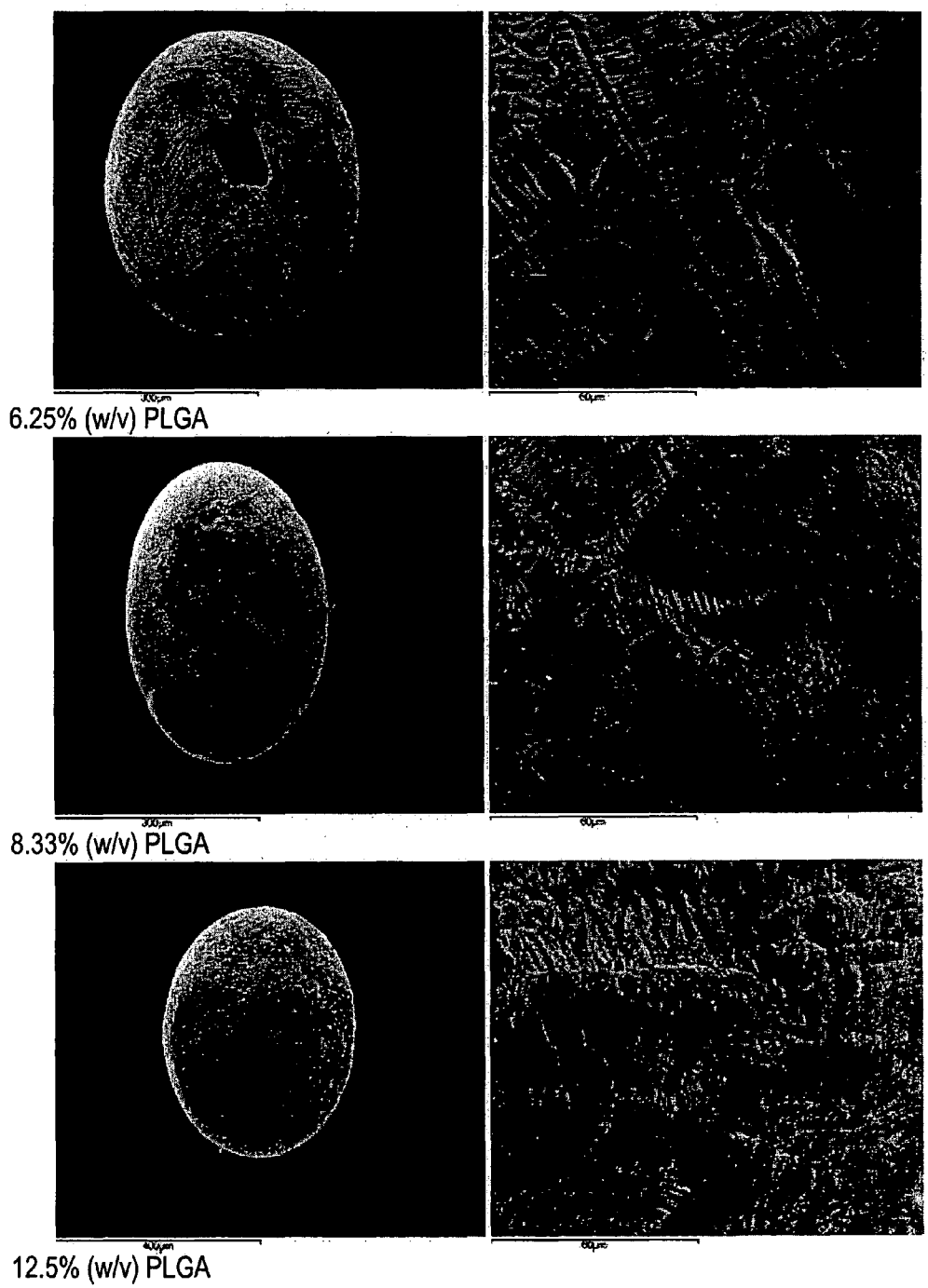

FIG. 22 is a scanning electron micrograph of TIPS microspheres produced using the encapsulation unit. Higher weight/volume % of polymer produced less porous microspheres.

Figure 23:
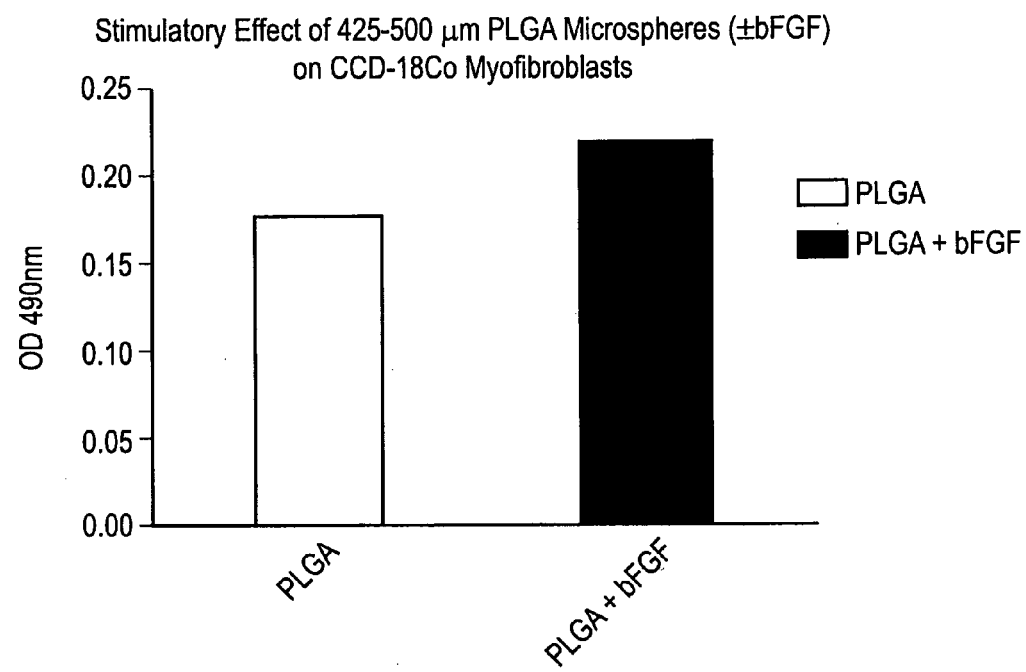

FIG. 23 shows that TIPS microspheres containing bFGF stimulated a significant increase in total cell number compared with control microspheres. ***p<0.0001

Figure 24:
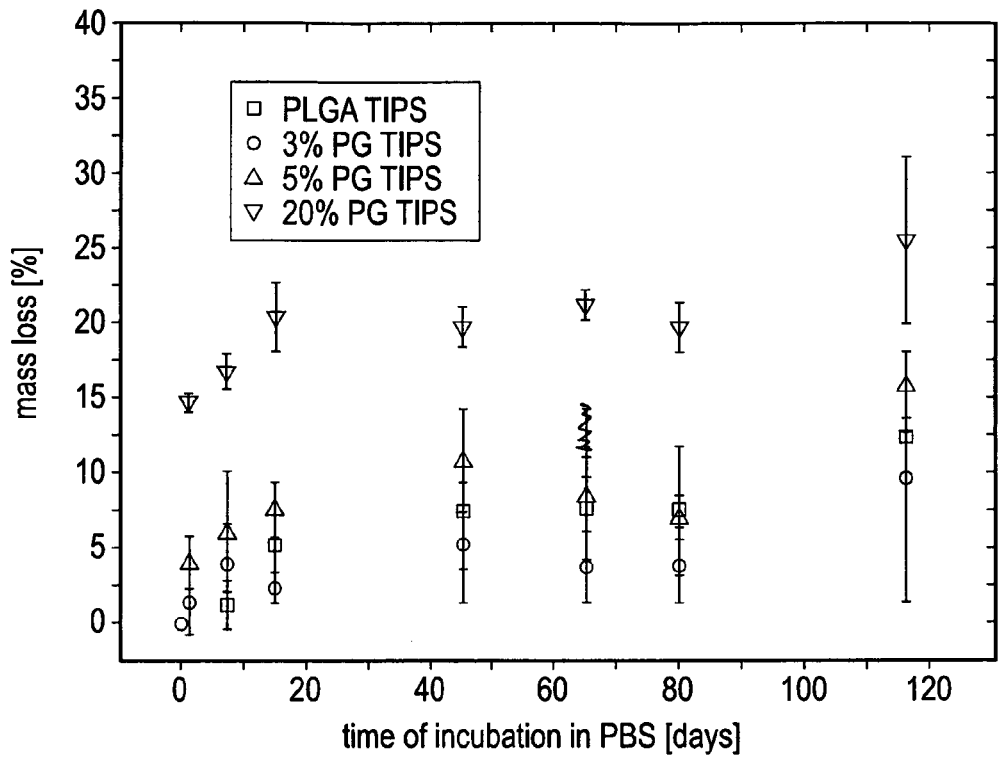

FIG. 24 shows change in mass loss of the spheres as a function of degradation time in phosphate buffered saline at 37° C. for TIPS microspheres.

Figure 25:
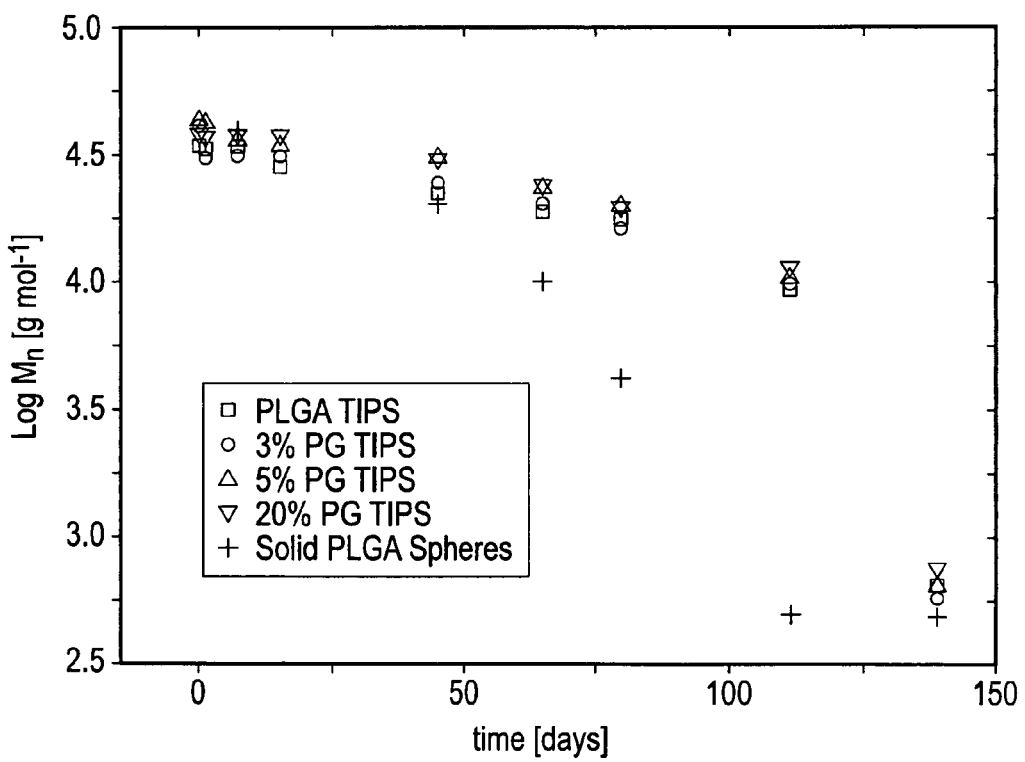

FIG. 25 shows change in number average polymer molecular weight as a function of degradation time in phosphate buffered saline at 37° C.

Figure 26:
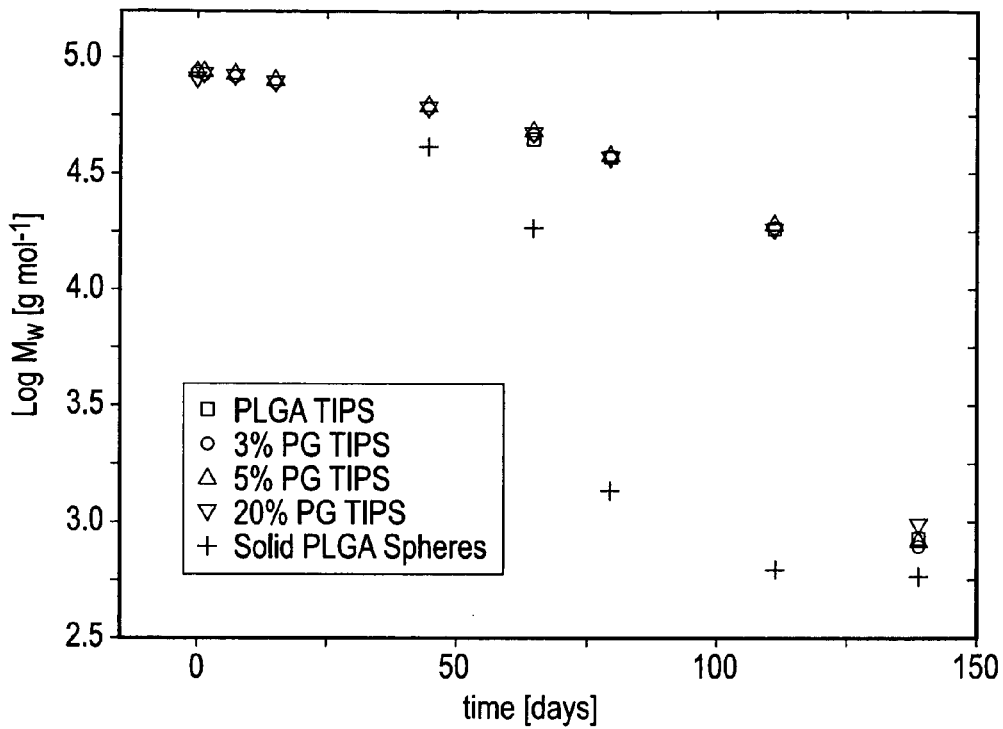

FIG. 26 shows change in weight average polymer molecular weight as a function of degradation time in phosphate buffered saline at 37° C.

Figure 27:
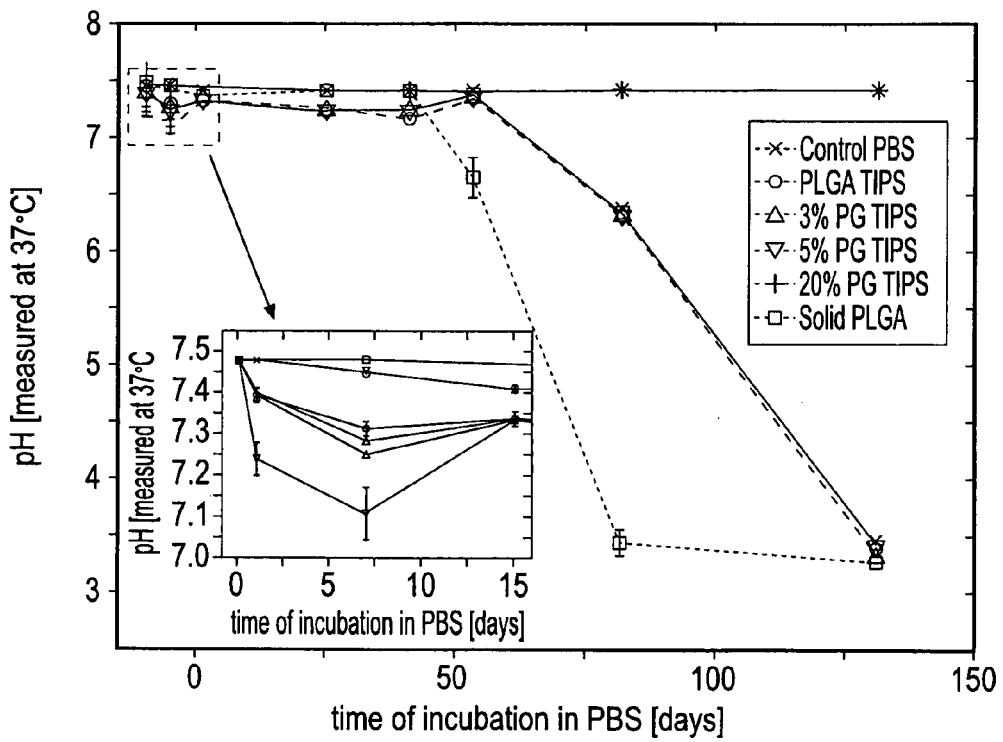

FIG. 27 shows change in pH of the phosphate buffered saline media as a function of degradation time. The initial reduction in pH for the phosphate glass samples is due to the evolution of phosphoric acid.

Figure 28:
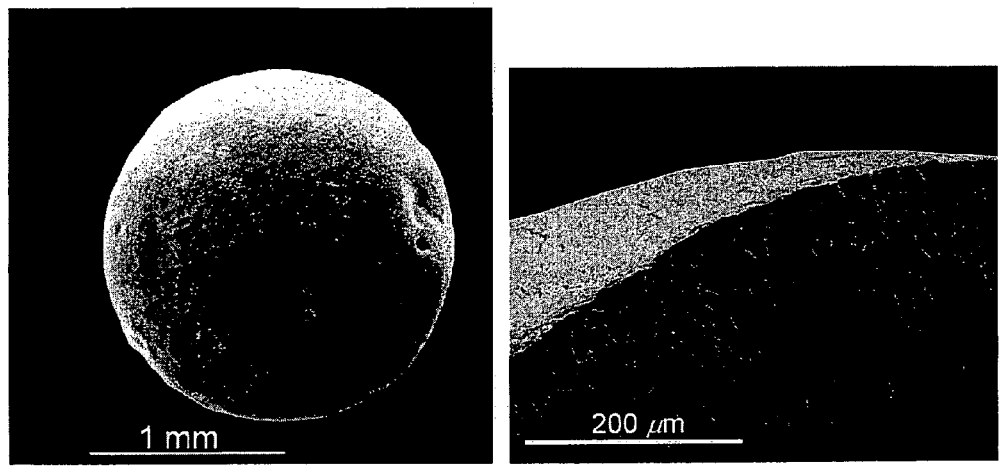

FIG. 28 shows neat PLGA TIPS microsphere after 3 days degradation shown exterior (left) and sectioned (right). Note the porous structure extending to the exterior surface.

Figure 29:
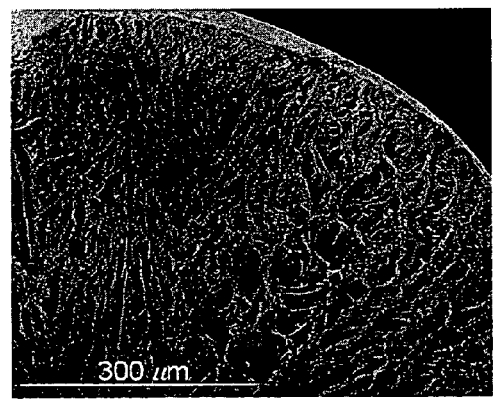

FIG. 29 shows that after 45 days degradation all TIPS microspheres started to show the onset of densification and shrinkage from the exterior (slight reduction in porosity at the exterior). Shown here is a 20 wt. % phosphate glass filled PLGA sample.

Figure 30:
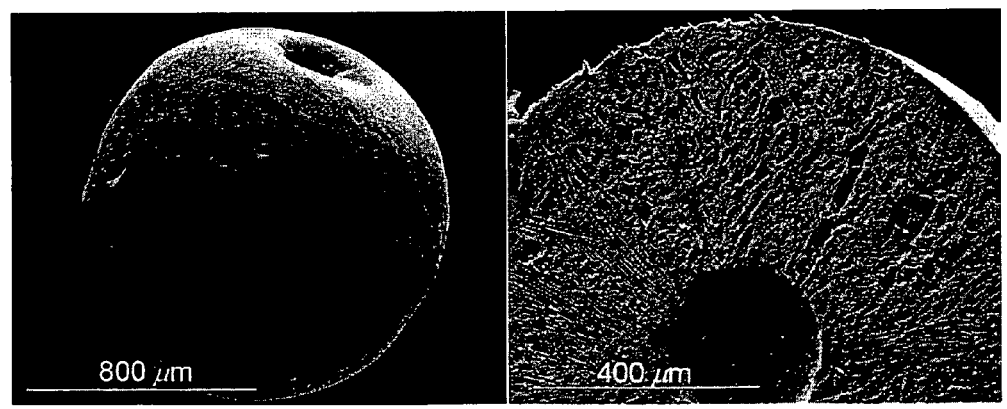

FIG. 30 shows that after 65 days all TIPS microspheres (shown here 20 wt. % phosphate glass filled PLGA-TIPS sample exhibited reduced diameter, corresponding to the densification of the exterior pore structure. Porosity appears progressively reduced from the outside to the centre. (Left image shows the exterior; right the sectioned sphere.)

Figure 31:
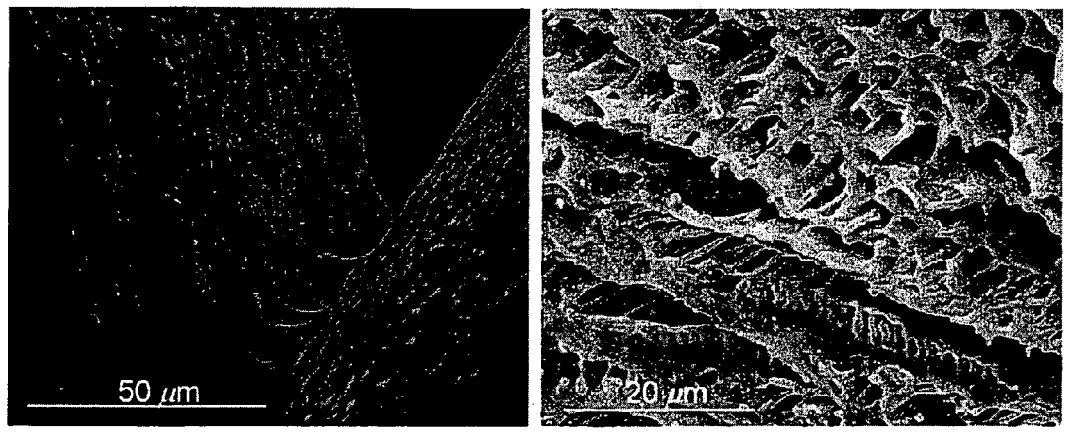

FIG. 31 is a SEM image showing the joining of spheres after 65 days, this behaviour was typical of all types microspheres; solid microspheres exhibit similar behaviour but at 80 days. This behaviour is due to plasticisation of the polymer and reduction in glass transition temperature. At this time point, much of the interior pore morphology is maintained, as shown (right) for the sectioned spheres.

Figure 32:
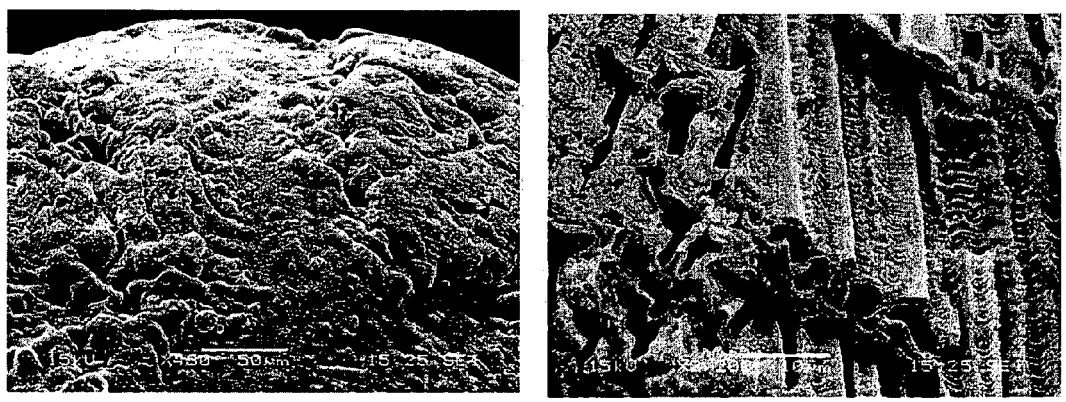

FIG. 32 shows that after 80 days degradation the TIPS microspheres started to show signs of blistering on the exterior, however, the internal porous structure (right) remained morphologically similar (though was increasingly brittle).

Figure 33:
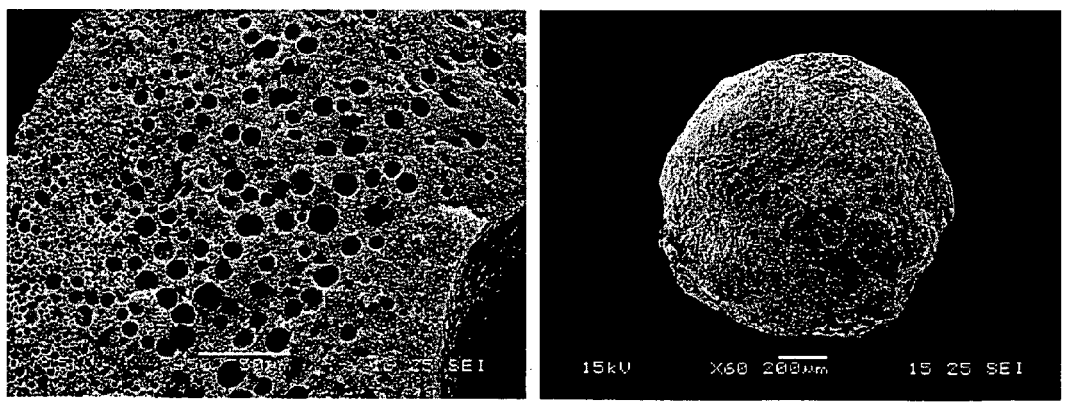

FIG. 33 shows that after 112 days degradation, TIPS microspheres exhibited signs of significant degradation, with blistering in the thickest polymer wall sections and the appearance of many spherical pores, replacing the tubular pore structure. (The diameter of the microspheres (as shown right) had significantly reduced in size.

Figure 34:
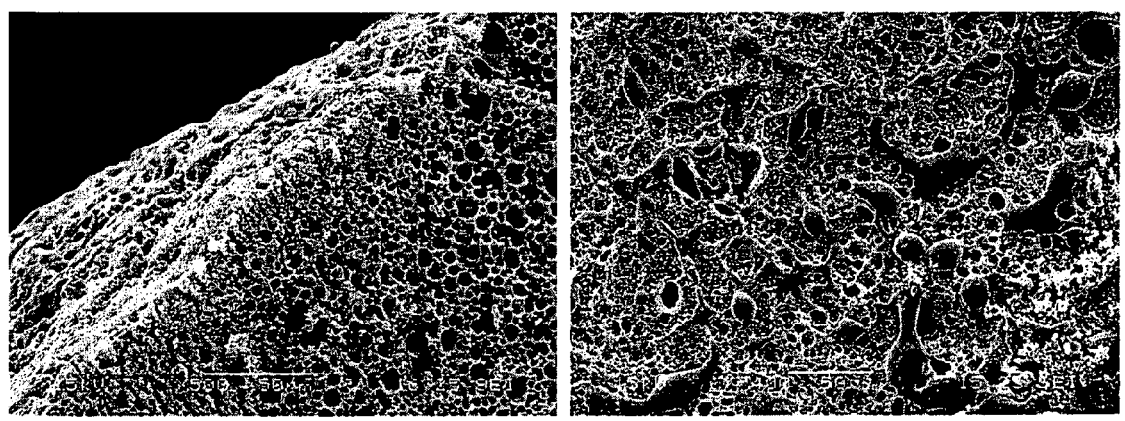

FIG. 34 is SEM images of TIPS microspheres degraded for 112 days, showing the internal (left) and external (right) pore structure. The previously well ordered 'chevron'-like exterior had become replaced by a more open spherical porous structure, which was consistent throughout the TIPS microspheres.

Figure 35A:
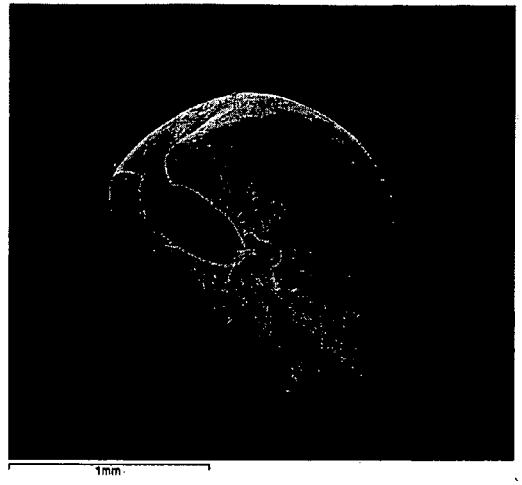
Figure 35B:
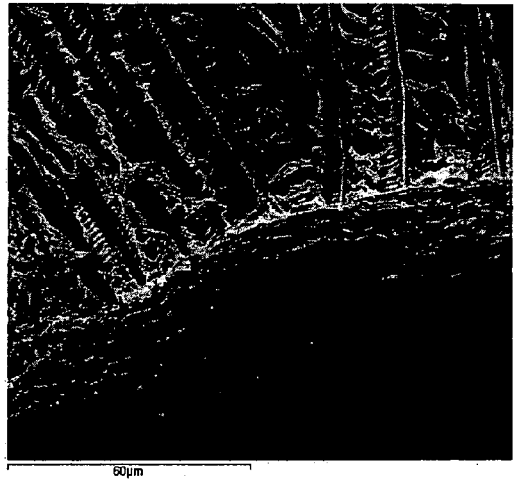
Figure 35C:
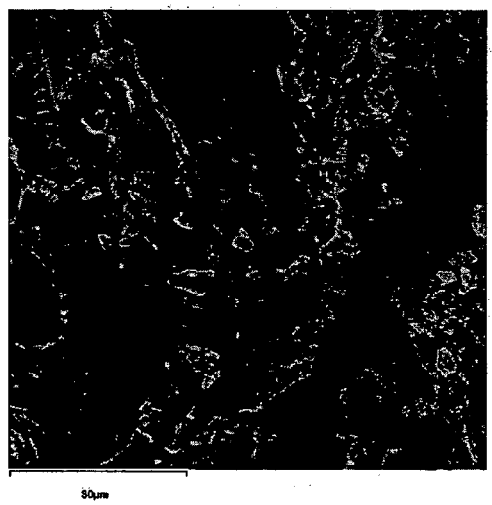
Figure 36:
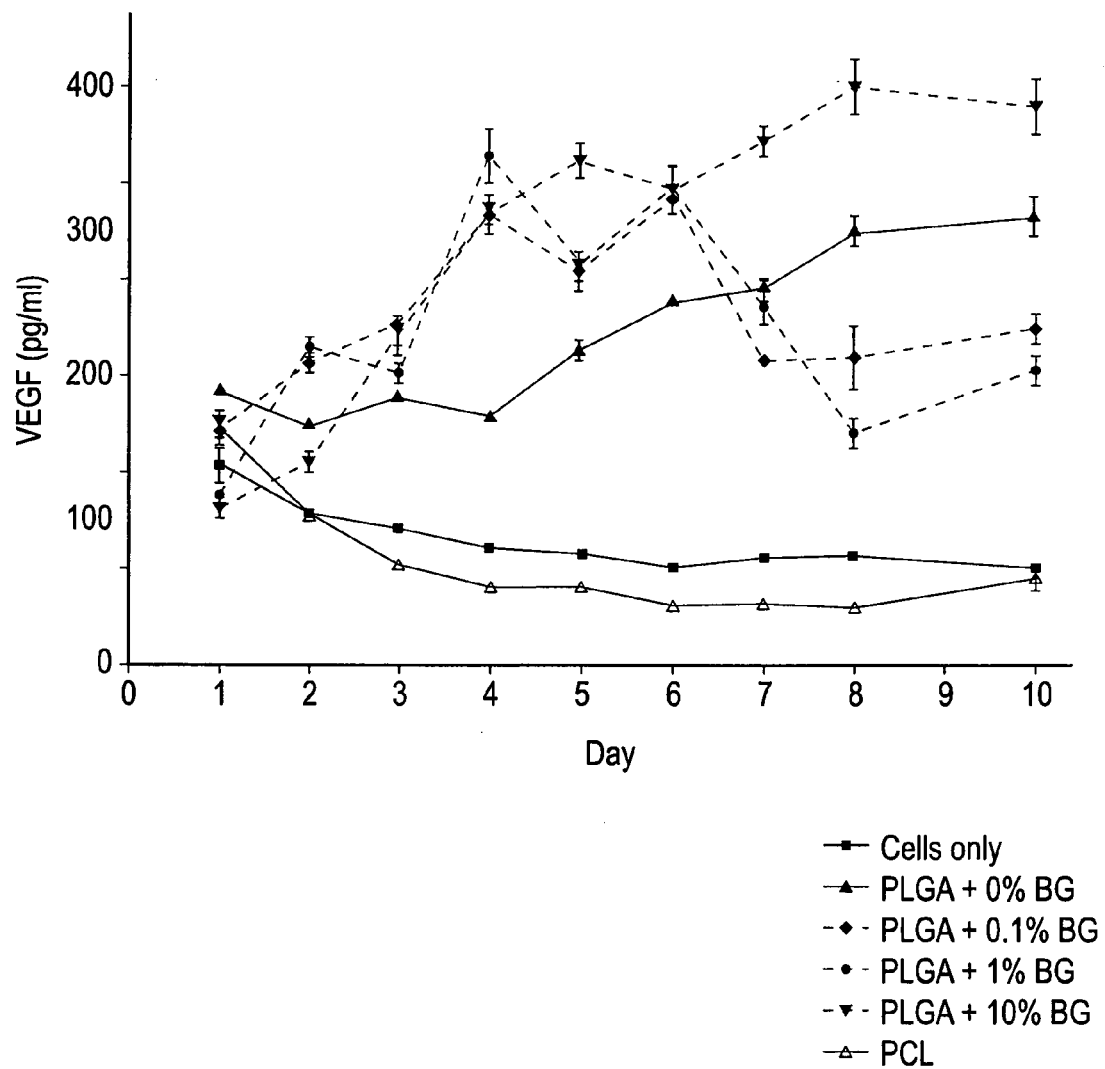

FIG. 35 is a SEM showing the typical morphology of bisected TIPS microspheres. (a) The microsphere surface consists of a skin about 2 μm thick with pores arranged in a chevron-like pattern. The interior of the microspheres show a highly ordered interconnected tubular morphology with a ladder-like substructure orientated in a radial pattern towards a void inside the microsphere that is also connected to the exterior surface via a neck. (b) Pores passing through the microsphere open out into the void. (c) The walls of pores in TIPS-BG microspheres contain evenly distributed BG particles FIG. 36 shows VEGF secretion from myofibroblasts in response to PLGA microspheres containing different concentration of BG or neat PCL microspheres.

Figure 37:
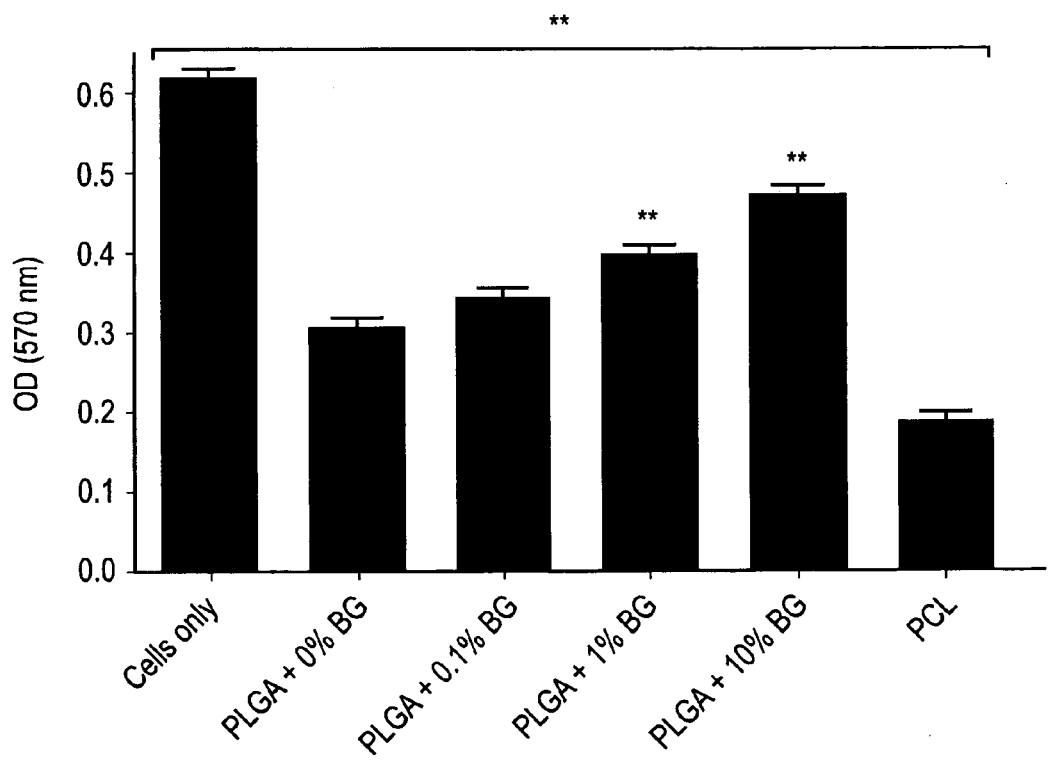

FIG. 37 shows cell viability in response to microspheres containing different concentrations of BG. All types of microspheres produced a significant reduction in cell viability compared with unstimulated control cells (P<0.01). Significantly more viable cells were associated with PLGA microspheres containing 1% and 10% BG compared with neat PLGA microspheres.

Figure 38:
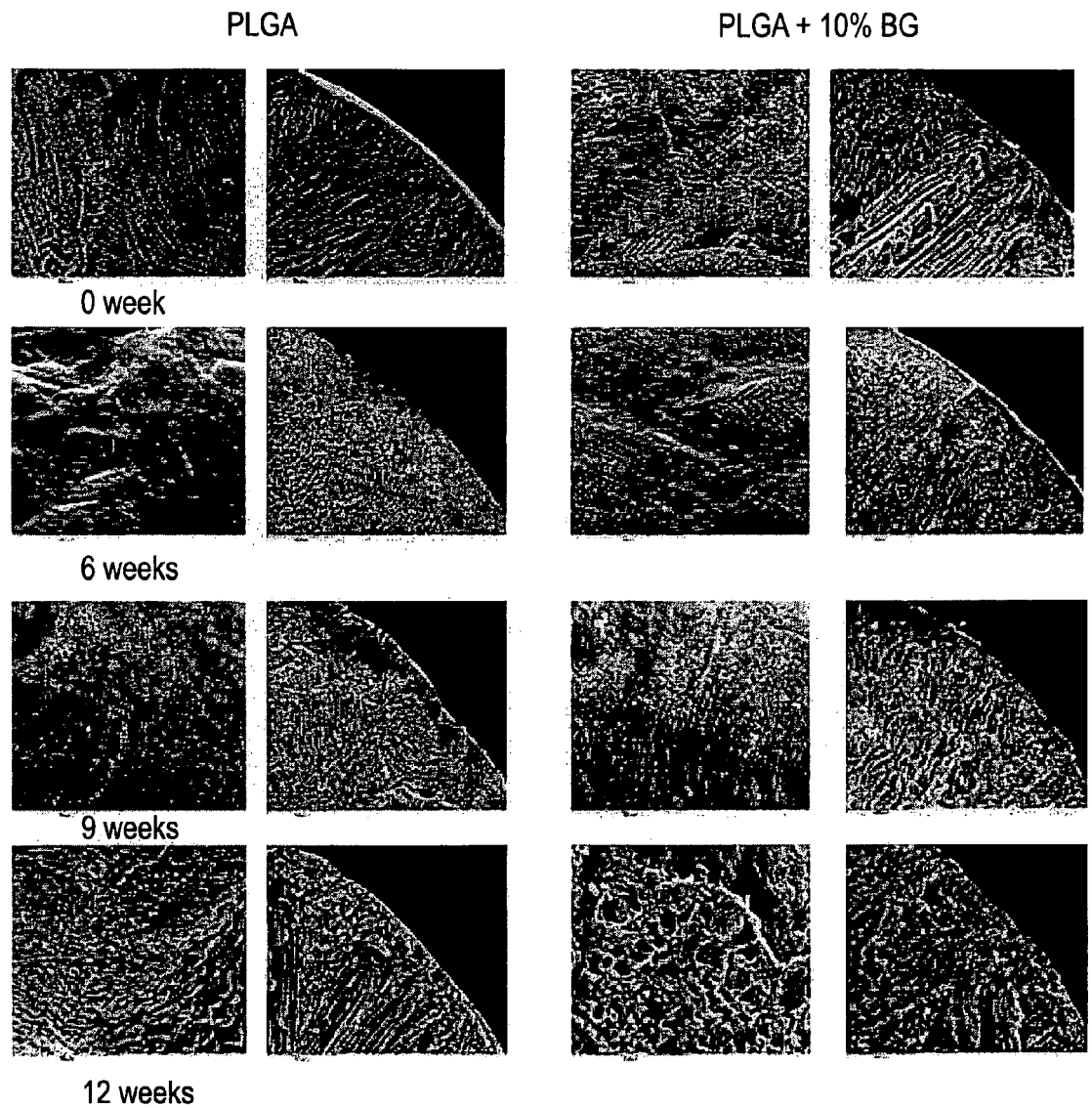

FIG. 38 is a SEM of neat PLGA and PLGA-BG TIPS microspheres. Surface porosity, with pores arranged in chevron-like patterns, is similar for both types of microsphere up to week 9. At week 12 the surface of both types of microsphere appears distorted with the ordered porosity being replaced by a more rugose topography. Bisected microspheres reveal the highly ordered interconnected tubular morphologies with a ladder-like substructure largely intact after 12 weeks degradation.

Figure 39:
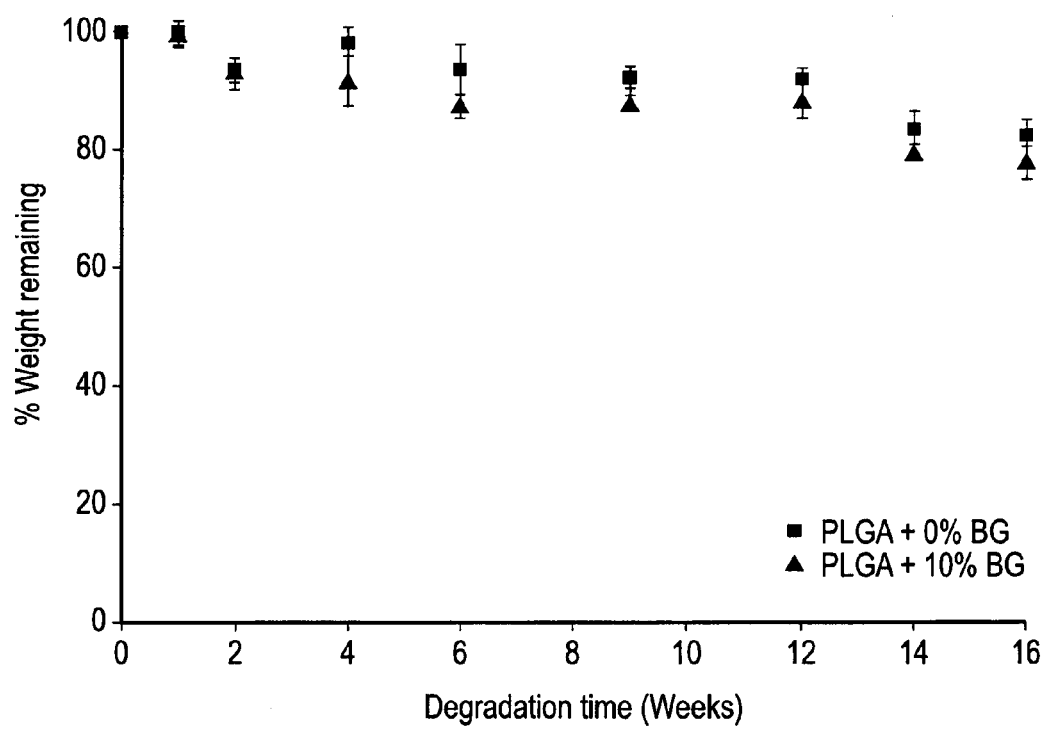

FIG. 39 shows percentage weight change of neat PLGA or PLGA-BG microspheres following degradation in PBS.

Figure 40:
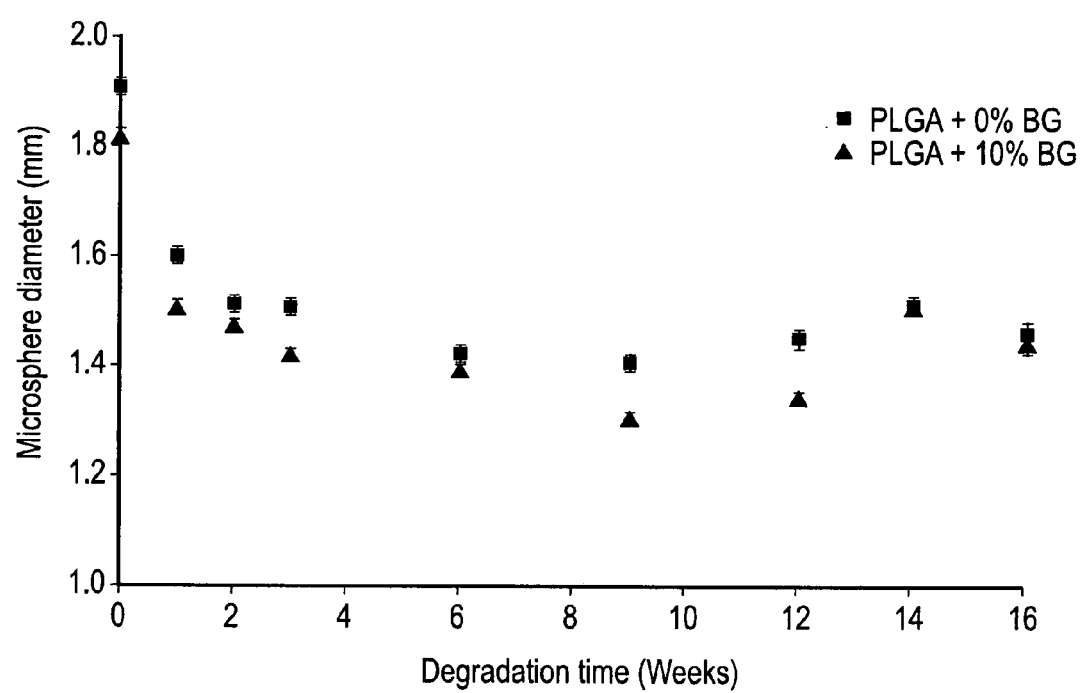

FIG. 40 shows change in size of neat PLGA or PLGA-BG microspheres following degradation in PBS. Both types of microsphere follow similar pattern of size reduction.

Figure 41:
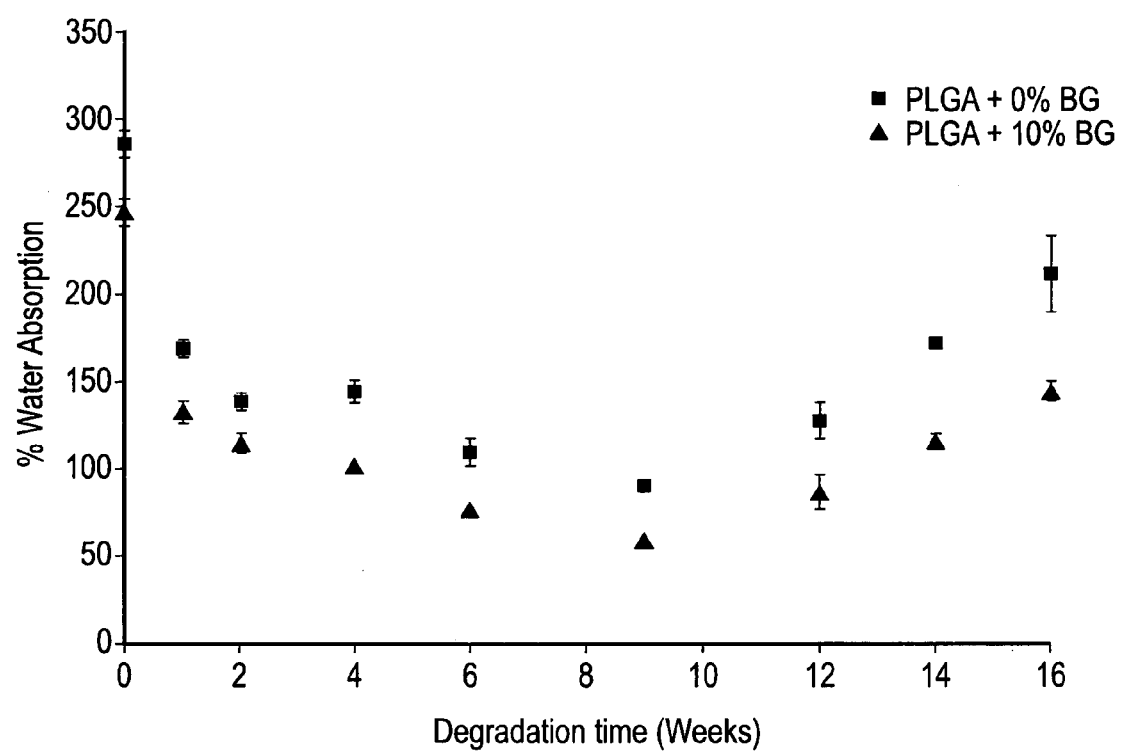

FIG. 41 shows water absorption by neat PLGA or PLGA-BG microspheres following degradation in PBS.

Figure 42:
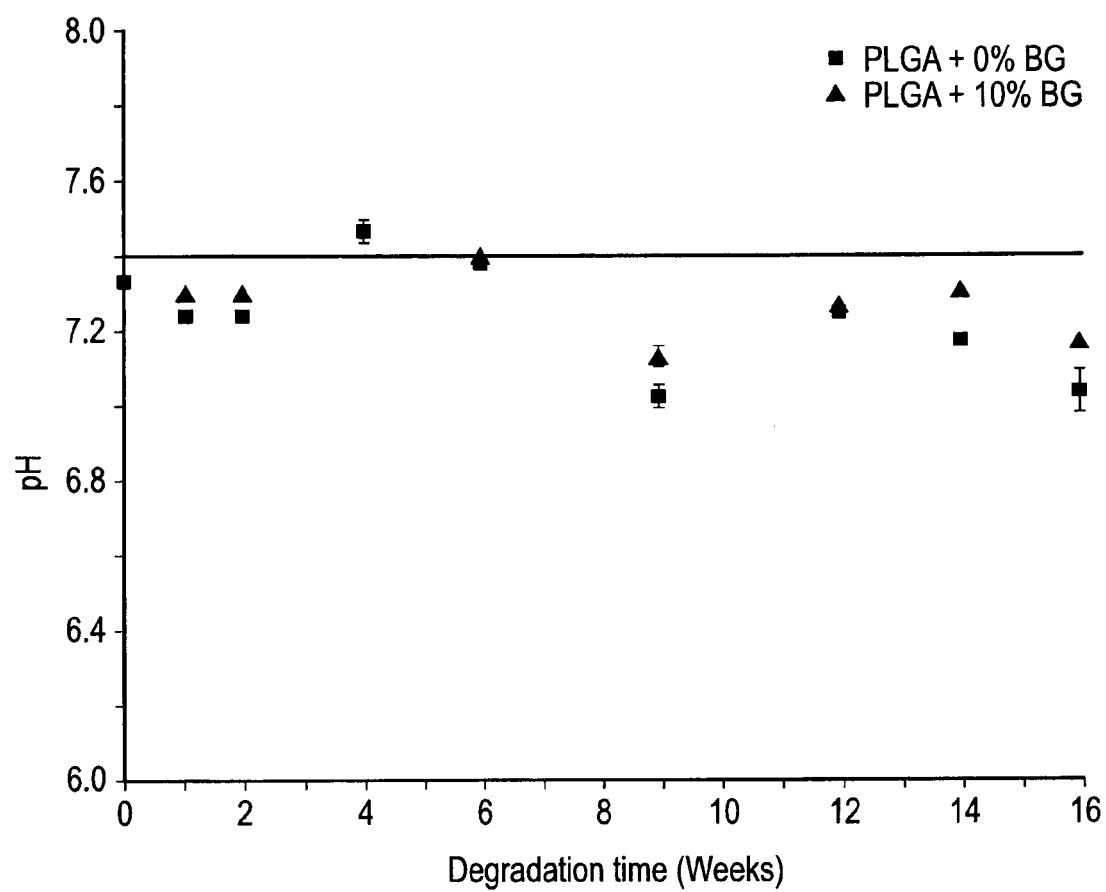

FIG. 42 shows that pH of the degradation medium remained above 7.0 throughout the study period. The pH for PLGA microspheres containing BG was slightly higher compared with the neat PLGA microspheres.

Figure 43:
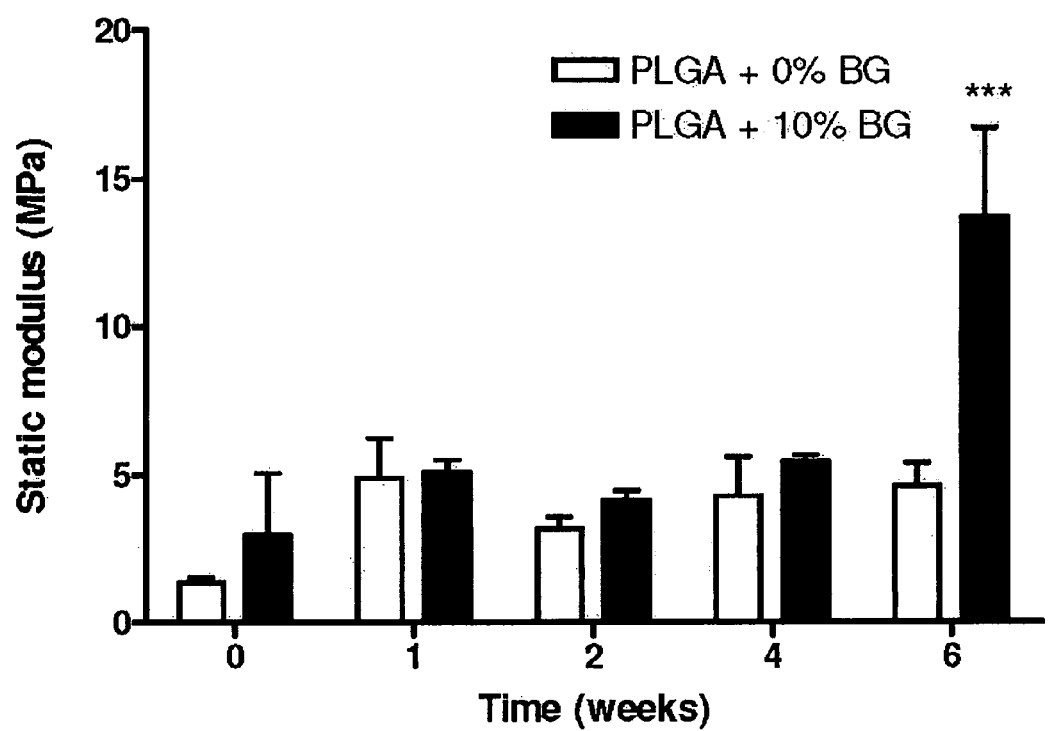

FIG. 43 shows the compressive mechanical strength of neat PLGA and PLGA microspheres containing 10% BG after degradation in PBS. The static modulus was similar for both sets of microspheres during degradation, except for microspheres containing 10% BG after 6 weeks when the modulus was significantly greater compared with neat PLGA microspheres at the same time-point (p<0.001).

Figure 44A:
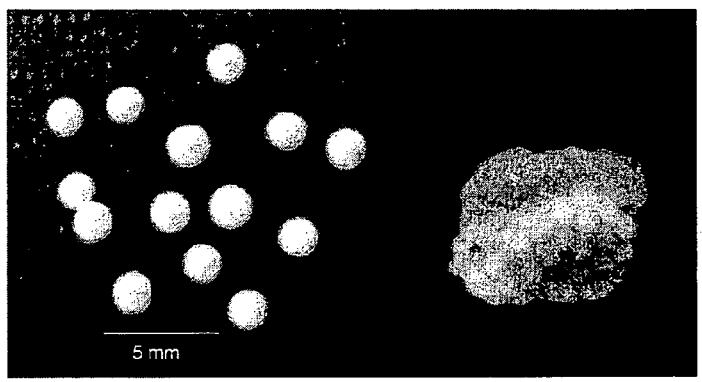
Figure 44B:
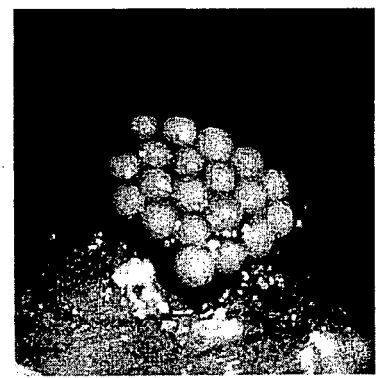
Figure 45A:
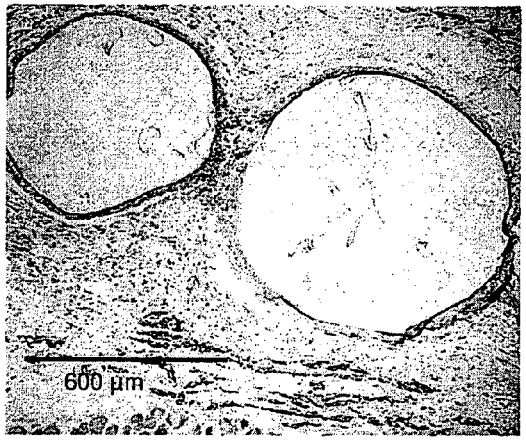
Figure 45B:
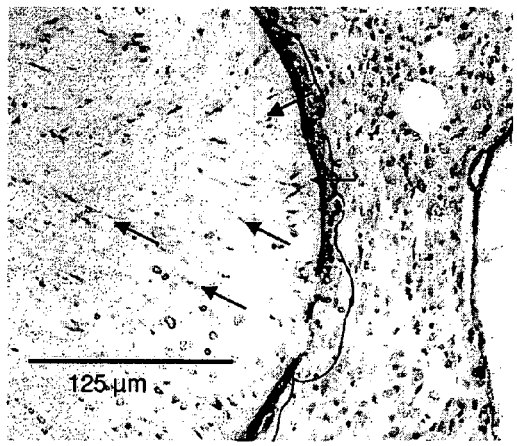
Figure 45C:
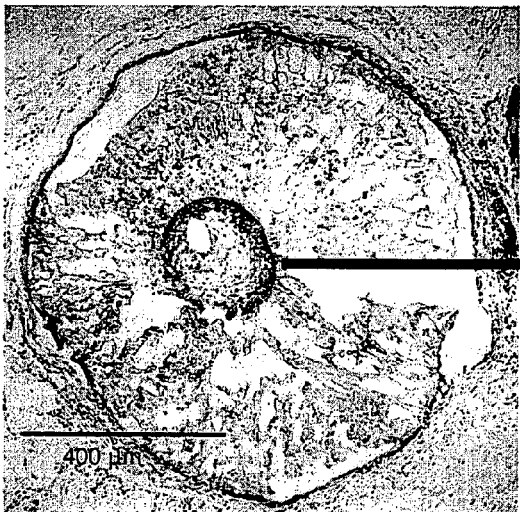
Figure 45D:
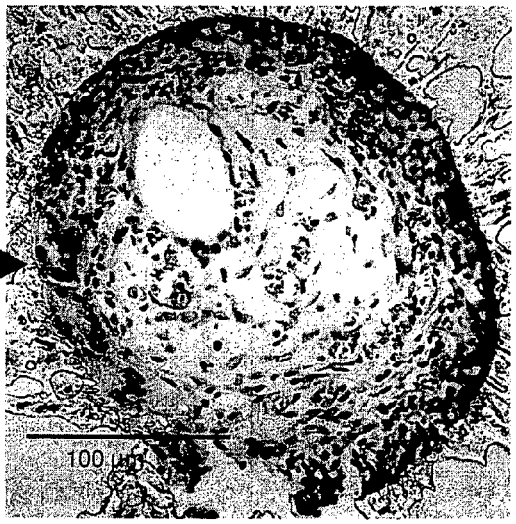

FIG. 44 shows (a) Microspheres pre-implantation and embedded in resected tissue after 6 weeks implantation. The implanted microspheres have become visibly smaller compared with their starting size due to polymer degradation. (b) Implanted microspheres in situ prior to resection. The microspheres are completely embedded in vascularised tissue.

FIG. 45 is a histological analysis of microspheres implanted into subcutaneous tissue. (a) Tissue rapidly infiltrates interstices between packed microspheres (neat PLGA microspheres; 2 weeks post-implantation). (b) Cells (arrows) also rapidly infiltrate the radial tubular macropores originating at the surface of the microspheres with their migration being directed by the orientation of pores (direction of arrows) (neat PLGA microspheres; 1 week post-implantation). (c-d) Voids inside the microspheres became rapidly filled by fibrovascular tissue (PLGA microspheres containing 10% (w/w) BG; 2 weeks post-implantation).

Figure 46:
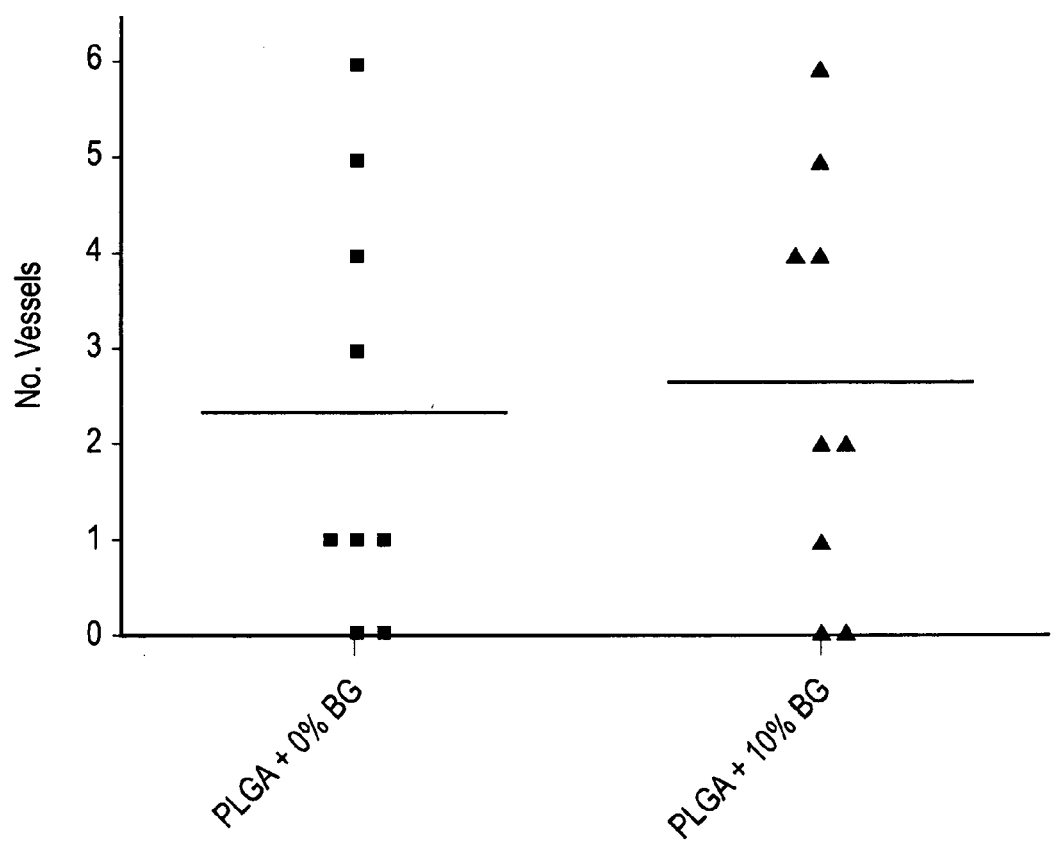

FIG. 46 shows the number of blood vessels counted in the voids of microspheres after 2 weeks subcutaneous implantation. Blood vessels were counted using a using a 25-point Chalkley point eyepiece graticule at a magnification of ×250.

Figure 47:
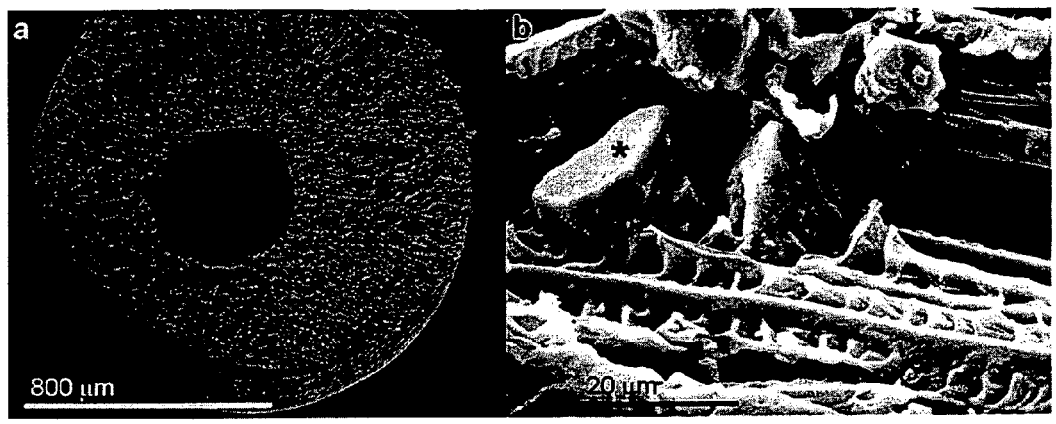

FIG. 47 shows scanning electron microscopy (SEM) images of a bi-sected phosphate glass containing microsphere (1a) showing the porous interior and the presence of a void in the centre of the sphere. The glass particles (*) can be seen embedded within the polymer matrix (1b). SEM was conducted as previously described.

Figure 48:
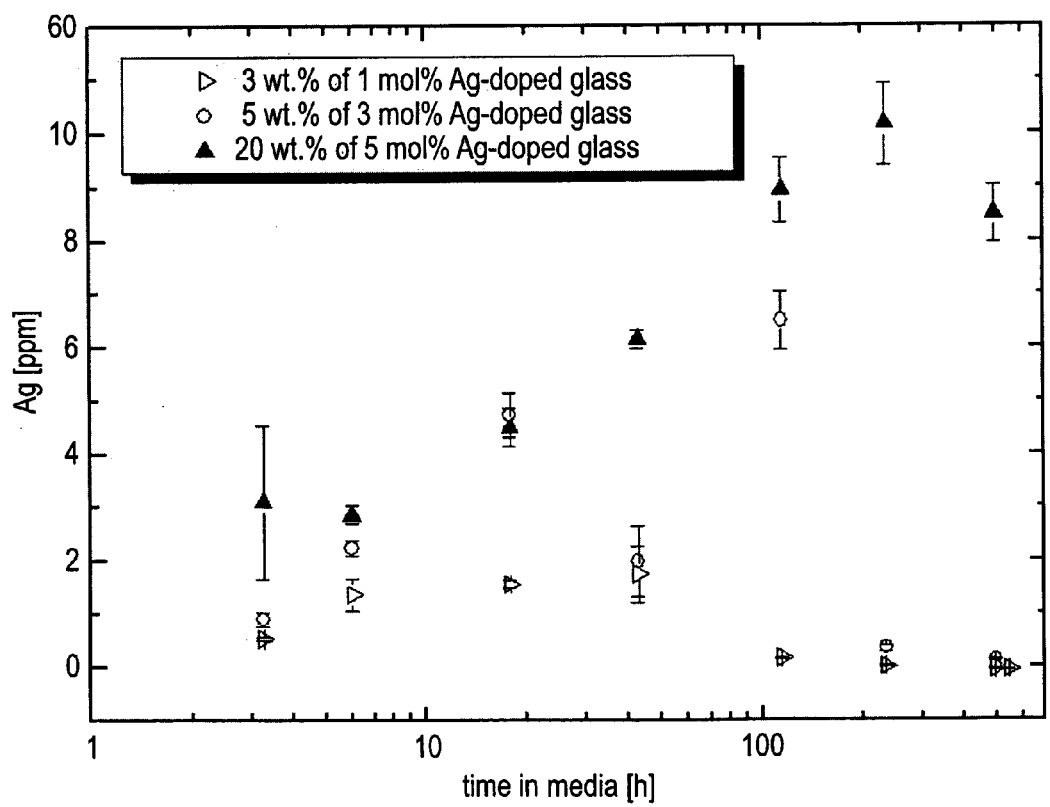

FIG. 48 shows dissolution of silver (Ag) from the PLGA microspheres as a function of immersion time in phosphate buffered saline.

Figure 49:
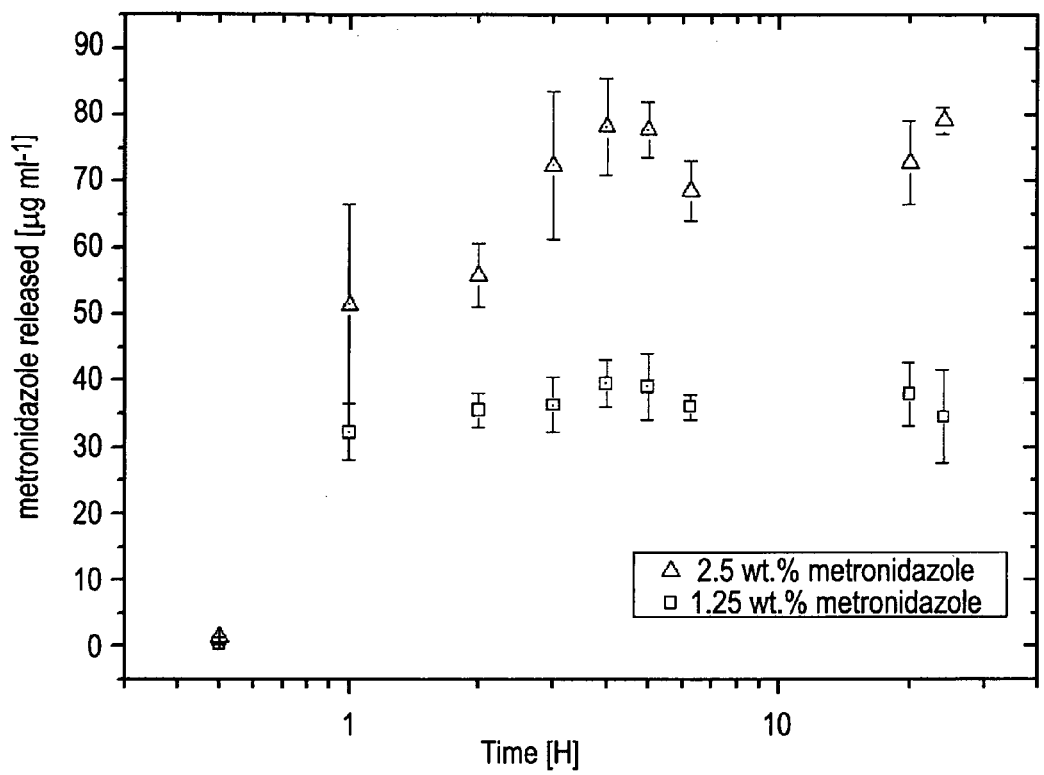

FIG. 49 shows time-dependent release profile of metronidazole from porous spheres.

Figure 50:
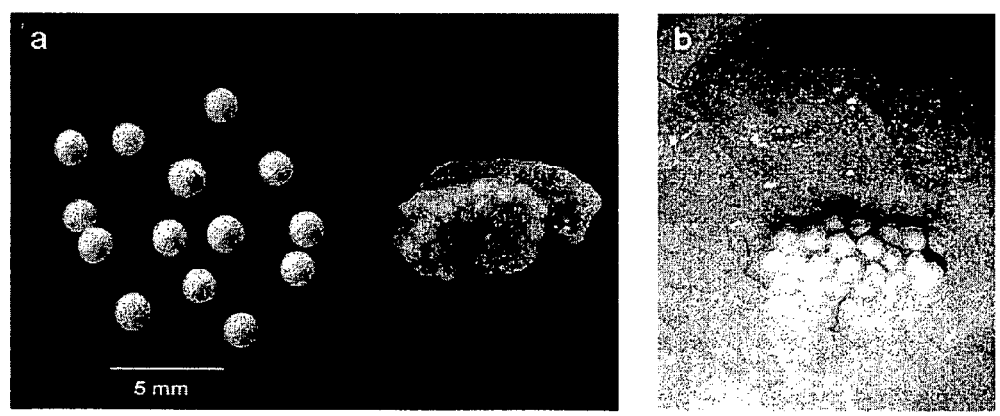

FIG. 50 shows (a) Microspheres pre-implantation and in resected tissue after 6 weeks implantation. The implanted microspheres have become smaller due to polymer degradation. (b) Implanted microspheres in situ prior to resection. The microspheres are completely embedded in vascularised tissue.

Figure 51:
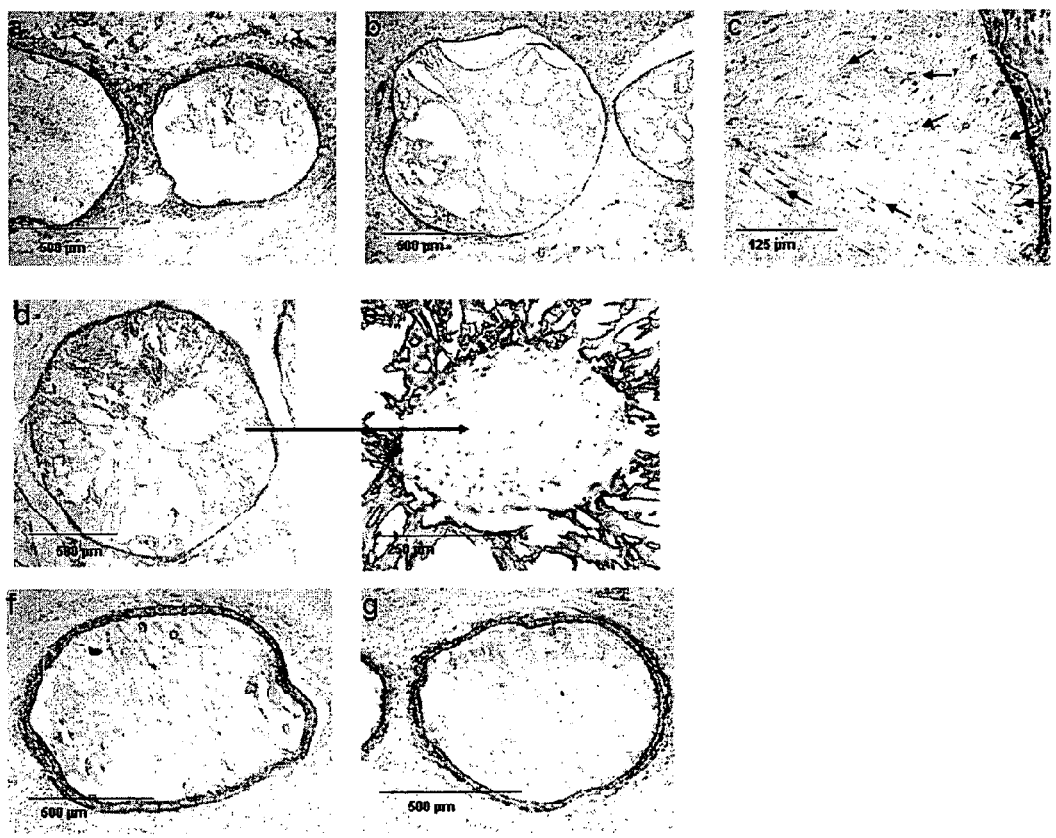

FIG. 51 is a histological analysis of implanted microspheres.

(a) Neat PLGA microspheres resected 1 week after subcutaneous implantation.

(b) Resected tissue containing PLGA microspheres filled with 5 wt % phosphate based glass doped with 3 mol % silver.

(c) Cell infiltration of the porous microsphere structure. Arrows indicate cells and their direction of migration.

(d and e) Cell infiltration of the void present toward the centre of the microspheres.

(f) Neat PLGA microspheres 6 weeks post-implantation.

(g) PLGA microspheres filled with 5 wt % phosphate based glass doped with 3 mol % silver 6 weeks post-implantation.

EXAMPLES

Example 1

Production of Microspheres Using the Thermally Induced Phase Separation Process (TIPS Microspheres)

Materials and Method

Poly(D,L-lactide-co-glycolide) (PLGA) (75:25) (Medisorb, Alkermes, USA) was used as the polymeric matrix, dissolved in dimethyl carbonate (of >99.9% purity, Sigma Alrich, UK). PLGA was dissolved in dimethyl carbonate (DMC) at 1:6 w/v (0.833 g PLGA was dissolved in 5 ml DMC for 2 h in a 25 ml Falcon tube, under magnetic stirring). The polymer solution was dripped from a syringe fitted with various sized needle orifices, into liquid nitrogen to rapidly induce the phase separation. Each drop of polymer solution was allowed to equilibrate to the liquid nitrogen temperature, demarked by sinking, prior to the addition of further drops to prevent microsphere agglomeration during processing. The frozen spheres were subsequently freeze-dried overnight to yield the TIPS microspheres. TIPS microspheres were sectioned using a Wilkinson Sword® razor blade to permit examination of the interior pore structure by scanning electron microscopy (SEM).

Results and Discussion

Figure 1:
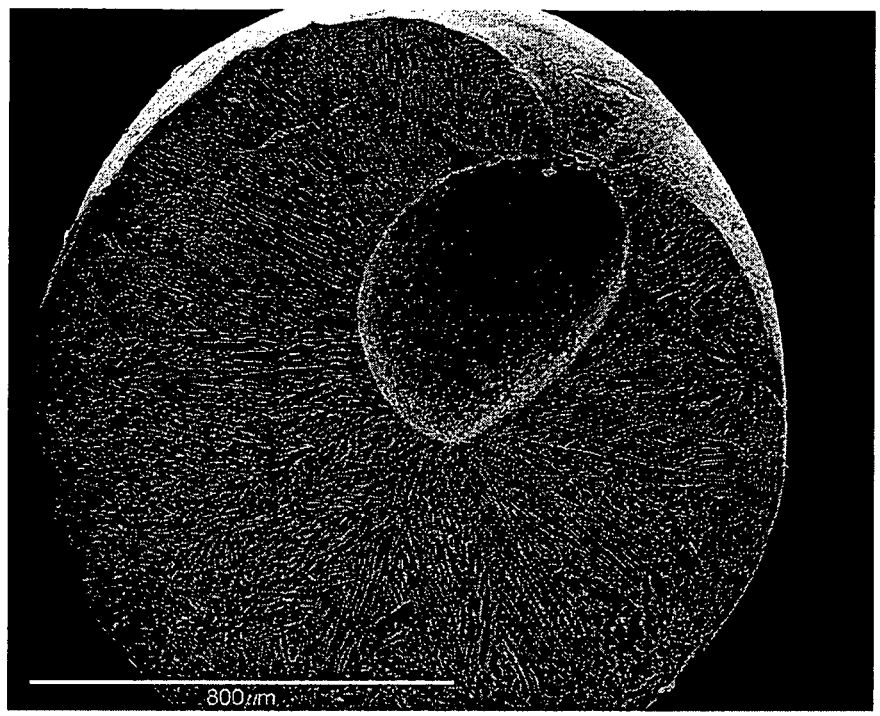
FIG. 1 is a scanning electron microscope (SEM) image of a sectioned microsphere made in accordance with the invention from PLGA. The radial tubular pore structure can be seen.
Figure 2:
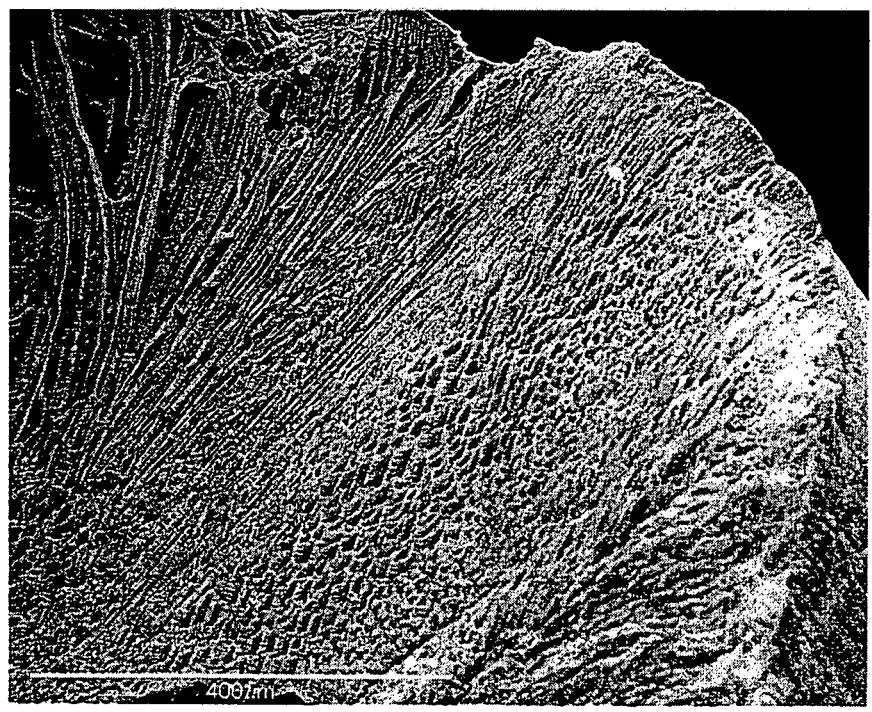
FIG. 2 is a higher magnification SEM image of the microsphere shown in FIG. 1.

The pore structure is highly interconnected with a structure typical of such TIPS foams. Specifically the DMC solvent has a freezing temperature of −1° C. and if the polymer solution is frozen rapidly using liquid nitrogen tubular pores develop due to the crystallisation front of the freezing solvent. Significantly here, the freeze front is from the outside in; therefore a radial pore structure of tubular pores, interconnected by a ladder-like structure of smaller pores occurred, as shown in FIGS. 1 and 2.

The size of the microspheres is related to the size of the needle orifice, smaller needle orifices give smaller microspheres, as shown in Table 1, below.

TABLE 1

Effect of needle orifice size on microsphere size

| Needle orifice size | ~Microsphere size |
|---|---|
| 700 μm | 1.7 mm |
| 350 μm | 1.2 mm |
| 200 μm | 900 μm |

Smaller microspheres have been achieved in our lab by spraying PLGA dissolved at 1:6 (w/v) using a plant spray hand pump into liquid nitrogen. It is difficult to include particulate inclusions at these sizes due to the limiting size of the nozzles.

Conclusion

TIPS microsphere fabrication using dimethyl carbonate as a solvent and rapid quenching in liquid nitrogen resulted in highly ordered interconnected porosity, with radial pores (channel-like) produced from the advancement of the solvent crystallisation front towards the centre of the sphere (parallel to the direction of heat transfer) for a neat PLGA TIPS microsphere. During TIPS the solution is separated into a polymer-rich phase and a polymer-lean phase due to the crystallisation of the solvent, when the temperature of the polymer solution is lower than the freezing point of the solvent and the polymer is expelled from the crystallisation front to form a continuous polymer-rich phase. The solvent is sublimed to leave the pores, which are a three-dimensional fingerprint of the geometry of the solvent crystals. At higher magnification the structure of the neat PLGA TIPS microsphere is observed to have a highly anisotropic channel-like morphology with an internal ladder-like structure, which is a characteristic morphology of foams formed by solid-liquid TIPS (Maquet V, Boccaccini A R, Pravata L, Notingher I, Jerome R. Porous poly (alpha-hydroxyacid)/Bioglass composite scaffolds for bone tissue engineering. I: Preparation and in vitro characterisation. Biomaterials 2004 (18) 4185-94, Zhang R and Ma P X. Poly(α-hydroxyl acids)/hydroxyapatite porous composites for bone-tissue engineering. I. Preparation and morphology. J. Biomed. Mater. Res. 1999 (44) 446-455.). The exterior of the neat PLGA microspheres, composite and protein encapsulated TIPS microspheres consist of a skin region of about 2 μm thickness with a smooth polymer surface, peppered with pores of 1 to 5 μm and covered with chevron like patterns due to the initial freeze front of the solvent across the droplet surface. Once the freeze fronts progress towards the centre of the droplet, the pore structure becomes more ordered, interconnected and ladder-like. The size of the spheres can be controlled by the size of the needle orifice, with smaller spheres produced from needles of narrower orifice (Table 1). The microspheres are monodisperse due to the consistent droplet formation. Voids are evident in the samples and are due to the entrapment of air during the manual droplet formation method, and the short drop distance to the liquid nitrogen used in the current study. The voids consist of a neck extending from the exterior surface of the sphere. Formation of these air pockets might be prevented by the use of a vibrating needle and a more optimized processing technique. The microstructure of the pores and walls can be controlled by varying the polymer concentration, filler loading content, quenching temperature and solvent used. Porosity increases with decreasing polymer concentration and filler content (Maquet V, Boccaccini A R, Pravata L, Notingher I, Jerome R. Porous poly(alpha-hydroxyacid)/Bioglass composite scaffolds for bone tissue engineering. I: Preparation and in vitro characterisation. Biomaterials 2004 (18) 4185-94.). Foams of up to 95% porosity can be achieved using the TIPS technique (Maquet V, Boccaccini A R, Pravata L, Notingher I, Jerome R. Porous poly(alpha-hydroxyacid)/Bioglass composite scaffolds for bone tissue engineering. I: Preparation and in vitro characterisation. Biomaterials 2004 (18) 4185-94., Zhang R and Ma P X. Poly($\alpha$-hydroxyl acids)/hydroxyapatite porous composites for bone-tissue engineering. I. Preparation and morphology. J. Biomed. Mater. Res. 1999 (44) 446-455.). Our method using DMC as solvent and PLGA polymer enables the formation of a slightly dense skin region and radial pores, thereby enhancing the mechanical properties over a random pore structure.

The use of an electromagnetic vibrating needle may be employed to i) maintain dispersion of the particulates in the polymer solution, ii) prevent blocking of the needle and iii) achieve smaller microspheres (100 to 800 μm) by vibrating the nozzle itself. The deviations in sphere size will depend on the density and surface tension of the matrix. Roughly, the smallest achievable drop diameter is 1.5 to 2 times larger than the nozzle diameter used.

Example 2

Composite TIPS Microspheres of PLGA Filled with Solid Particulate: Anti-Microbial Phosphate Glasses as Solid Particulate and In Vitro Bacteriology Study The incidence of biomaterial-centred infections underlies the need to improve the properties of existing biomaterials. Combining the bioactive properties of phosphate-based glasses with that of the silver has been shown to inhibit infections without the use of antibiotic drugs. Inclusion of phosphate-based glass doped with silver into biodegradable poly(D,L-lactide-co-glycolide) porous microspheres is explored using in vitro characterisation techniques. By incorporating glass particles a composite with tailored mechanical properties can be achieved.

Materials and Method

Poly(D,L-lactide-co-glycolide) (PLGA) (75:25) (Medisorb, Alkermes, USA) was used as the polymeric matrix, dissolved in dimetyl carbonate (of >99.9% purity, Sigma Alrich, UK), and kindly provided by Dr Ifty Ahmed (Eastman Dental Institute UCL). Phosphate glasses were produced from $NaH_2PO_4$, $CaCO_3$, $P_2O_5$ (BDH, UK) and $Ag_2SO_4$ (Sigma Aldrich, UK). The compositions investigated has a fixed phosphate content of 50 mol %, with a fixed CaO content of 30 mol %, with $Na_2O$ substituted with Ag 5 mol %. Glasses were ground using a rotating ball mill and sieved to <20 μm. Glasses were stored in a cool, dark environment prior to the investigation. PLGA was dissolved in dimethyl carbonate (DMC) at 1:6 w/v (0.833 g PLGA was dissolved in 5 ml DMC for 2 h in a 25 ml falcon tube, under magnetic stirring). Three batches of TIPS microspheres were produced: i) PLGA-filled with 20 wt % phosphate based glass, ii) PLGA-filled with 20 wt % phosphate based glass doped with 5 mol % Ag, iii) neat PLGA (1.25 ml of PLGA/DMC solution). To ensure adequate mixing of the bioactive glass particulates and homogenous distribution within the polymer solution, all mixtures were sonicated for 15 minutes and subsequently vortexed immediately prior to dripping from a syringe fitted with a 25G needle, into liquid nitrogen to rapidly induce the phase separation. Each drop of polymer solution was allowed to equilibrate to the liquid nitrogen temperature, demarked by sinking, prior to the addition of further drops to prevent microsphere agglomeration during processing. The frozen spheres were subsequently freeze-dried overnight to yield the TIPS microspheres. Bactericidal inhibition studies were conducted by sinking the spheres in bacterial culture media and various numbers of spheres were added to the wells of 96 well tissue culture plate (from 1 to 25 spheres, with 5 repeats of each number), and the media inoculated with $E.\ coli$ at $10^4$ bugs per well. The culture was left overnight at 37° C. in a humidified incubator with 5% $CO_2$. The turbidity of the media was measured spectrophometrically after the culture period to determine the influence of the materials on bacterial inhibition.

Results and Discussion

Composite TIPS Microspheres

Silver-doped phosphate-based glass particles were incorporated successfully within the PLGA TIPS microspheres with no apparent loss of glass particles during the processing, demonstrated by none remaining in the vial containing the liquid nitrogen. The glass particles were distributed homogeneously throughout the microsphere foam structure, as evidenced by scanning electron microscopy of a 20 wt % phosphate glass containing sample. Glass particles can be observed on the exterior surface of the spheres. The pore structure became progressively less well ordered with increasing glass content, due to perturbation of the crystallizing solvent by the solid phosphate-based glass particles. This resulted in more irregular crystal growth, with the pores becoming less well ordered, more isotropic, with lesser channel structures or ladder-like partitions observed with increasing glass content.

The inclusion of silver-doped phosphate glass within the spheres resulted in marked bacterial inhibition/kill, as shown in FIG. 7, over the neat PLGA and phosphate glass containing PLGA TIPS microspheres. The mechanical properties (determined by tactile examination only) seemed superior to those of the PLGA TIPS microspheres alone (they were apparently stiffer and stronger).

The release profile of silver ions over time from the PLGA microspheres containing silver-doped phosphate glasses was determined by inductively coupled plasma optical emission spectroscopy (FIG. 9). Ten microspheres from each concentration of silver containing phosphate glass were placed into individual wells of a 48-well tissue culture plate in replicates of three and immersed in 420 μl cell culture medium. The release profiles from the spheres were assessed after incubation at 37° C. for 30 minutes, 3, 6, 18 h and 2, 7, 12, 16 and 21 days.

The continued dissolution of silver ions from the PLGA microspheres containing 20 wt. % silver-doped phosphate glass was apparent (FIG. 9). Silver concentration was at ~3 ppm after 6 h incubation, and steadily increased to ~10 ppm at day 10, after which a moderate drop off was detected.

Conclusion

The inclusion of phosphate glass and silver-containing phosphate glass particulates within the PLGA TIPS microspheres was successful in terms of achieving apparent total encapsulation of the particles and their homogenous distribution within the TIPS microspheres. The release of silver from the microspheres resulted in dramatic bacterial inhibition/kill. Such anti-bacterial microspheres could be of use in tissue engineering in providing a mechanism to prevent infection (without the use of antibiotics) and to enhance the mechanical properties of the PLGA microspheres. It is possible to include solid particulates, even nano particulates using this rapid cryogenic TIPS technique.

Example 3

TIPS Microspheres Loaded with Protein and Emulsion TIPS Microspheres

This experiment investigates the feasibility of incorporating proteins (in aqueous solutions) into poly(D,L-lactide-co-glycolide) (PLGA) TIPS processed microspheres. The encapsulation, homogeneity and distribution of a model protein were assessed by fluorescence microscopy of Rhodamine-labelled antibody IgG at two different concentrations (0.0625% and 0.0156% by weight to the polymer). The addition of an aqueous phase with the polymer/solvent solution is likely to alter the pore structure (to generate a more homogeneous pore structure, with less orientated macro-pores) and to create cavities within the microspheres and on their periphery. As controls PLGA/solvent solution was combined with $dH_2O$, and neat PLGA/solvent solutions were prepared.

Materials and Method

Protein

Rhodamine-labelled affinity purified antibody to Mouse IgG (H+L) was obtained from Kirkegaard & Perry Laboratories Inc. (Gaithersburg, Md., USA). According to the manufacturers, this antibody was isolated from a pool of serum from goats immunised with purified mouse IgG, and was labelled with tetrametyl rhodamine isothocyanate (TRITC). The antibody is stabilised and preserved with goat serum and bovine serum albumin. PLGA (75:25) (Medisorb, Alkermes, USA) was dissolved in dimethyl carbonate (DMC) at 1:6 w/v (0.833 g PLGA was dissolved in 5 ml DMC for 2 h in a 25 ml Falcon tube, under magnetic stirring). The antibody was incorporated either directly to the polymer solution or rehydrated and dispersed in 250 μl of $dH_2O$ at two different concentrations (0.0625% and 0.0156% w/w to the polymer). Solutions were homogenised for 3 minutes at 5000 rpm using a T8 Ultra-Turrax® homogeniser (IKE®-WERKE, Staufen, Germany). Solutions were delivered dropwise into liquid nitrogen via a 25G needle and the TIPS microspheres were obtained as described above. All compositions were homogenized (speed 5) for 3 minutes, prior to dripping from a syringe fitted with a 25G needle, into liquid nitrogen to rapidly induce the phase separation. Each drop of polymer solution was allowed to equilibrate to the liquid nitrogen temperature, demarked by sinking, prior to the addition of further drops to prevent microsphere agglomeration during processing. The frozen spheres were subsequently freeze-dried for 24 h to yield the TIPS microspheres.

Emulsion

PLGA was dissolved in DMC as described above and $dH_2O$ was added to the solution at various volume ratios of 0.05, 0.1, 0.25, 0.5 and 1:1 of $dH_2O$ with respect to the polymer solution. Solutions were homogenised as described above for 5 minutes prior to dropping the emulsified solutions into liquid nitrogen using a 25G needle to yield the TIPS microspheres as indicated previously.

Fluorescence Microscopy

Spheres were examined in both whole states and as sections (prepared using a Wilkinson Sword® razor blade), placed on glass microscope slides and mounted with Immunofluor™ prior to the addition of glass cover slips. Control and antibody encapsulated samples were assessed with an excitation of 552 nm (for the TRITC fluorochrome, colour: red-orange) and at 495 nm to detect the spheres, as they auto-fluoresce green under these conditions.

Results and Discussion

Emulsion TIPS Microspheres

The inclusion of an aqueous phase that is immiscible with the polymer resulted in an emulsion after homogenising. The emulsion became thicker with increasing ratio of $H_2O$ to polymer solution, almost to a mayonnaise-like consistency at a 1:1 ratio upon homogenisation. Droplet formation became progressively difficult with increasing $H_2O$ beyond this ratio, as the solution became too viscous to deliver manually dropwise from the syringe needle. At lower ratios of water to polymer solution (up to 0.5:1) increasing the aqueous phase resulted in less well-ordered pore morphology and the generation of larger, more spherical pores. The addition of $H_2O$, a non-solvent, reduced the solubility of the PLGA, with liquid-liquid phase separation occurring prior to solvent crystallisation, resulting in a more disrupted pore structure, and at lower concentrations (0.25:1 and 0.5:1 of $H_2O$ relative to the polymer solution) a more wrinkled exterior surface could be observed on SEM examination compared with neat TIPS microspheres prepared by PLGA/DMC (FIG. 4a). The pore morphology became progressively less channel-like and resulted in larger, interconnected spherical pores of between 30 to 70 μm diameter and a fibre-like network with increasing $H_2O$ content, as shown in FIGS. 4b and 4c for the spheres produced with water concentrations of 0.25:1 and 0.5:1 relative to the polymer solution, respectively. Spheres produced using 1:1 ratios of $H_2O$ to polymer solution were very fragile and crumbled on handling (FIG. 6a). SEM examination revealed their inside contained a large number of discrete well-formed microspheres of 10 to 200 μm diameter, which have open porous surfaces as shown in FIGS. 6b and 6c, at low and high magnification, respectively.

Protein Incorporation

The labelled antibody could clearly be observed within the spheres when excited at 552 nm (as shown in FIG. 8). Spheres at the lower concentration were far less contrasted. Control spheres exhibited no red-orange fluorescence at this wavelength; however, both antibody-encapsulated and neat PLGA TIPS spheres did auto-fluoresce green at an excitation wavelength of 495 nm. The antibody encapsulated spheres are more contrasted towards their centres due to the 3-D nature of the samples (thicker in the z plane towards their centres). The radial pore structure typical of such TIPS foams is observed (image top left of FIG. 8), resulting from the directions of freeze-fronts during thermal phase separation. The pockets observed in some of the spheres are an artefact of processing, which is most likely due to trapped air, as the droplet forms. Such pockets may be advantageous, especially in allowing cellular invasion. Formation of these air pockets could be prevented by the use of a vibrating needle and a more optimised processing technique. Conversely, homogenising the polymer solution with aqueous or other liquid or leachable solid phases and air could induce such cavities.

Conclusion

It is possible to incorporate antibodies into PLGA TIPS microspheres by mixing the protein into aqueous suspensions and homogenising this with the PLGA/solvent solution to form an emulsion, prior to TIPS. The fluorolabelled antibody appears to be distributed homogeneously throughout the sphere.

Example 4

A Rapid Vacuum Technique to Sink the Microspheres and Infiltrate them with Desired Liquids Sometimes it may be desirable to use the TIPS microspheres' property of low apparent density and initial high hydrophobicity for use as floating systems, or when filling blind pockets (in tissue) to allow air to escape during the filling procedure. However it is also desirable to sink the spheres for in vitro investigations and to determine drug release profiles. More importantly by rapidly displacing the air within the microspheres with water or for example cell culture media containing a cell suspension, the foam spheres can be rapidly infiltrated with the cells or liquid and thereby used as carriers for applications of liquid drug release, cell transplantation within the scaffold or for cell culture within bioreactors eliminating the problems of shear wall stress and cell detachment commonly encountered with solid microspheres. A method has been developed to rapidly infiltrate the spheres with liquids as outlined below.

Materials and Methods, Results and Discussion 1500 spheres were placed into a Falcon tube (50 ml capacity) and a barrier membrane (with 100 μm pores) was added at the 35 ml mark to keep the spheres submersed (FIG. 10). Media was added to 45 ml and then the open Falcon tube placed in a vacuum for 10 minutes. Upon removal of the vacuum, all the air is rapidly removed from the microspheres and displaced by the liquid (cell culture medium in this case) as the spheres are maintained submersed beneath the membrane. This technique could be applied to clinical situations whereby, the material is maintained dry and sterile, prior to the introduction of suitable media (under vacuum in a vessel) and subsequent release of the vacuum to rapidly sink the spheres. The technique could also be applied to draw cells into the pores and inner cores of the spheres to allow an already seeded scaffold to be introduced. Moreover, culture in a bioreactor may be used to build up the cell density prior to implantation. The technique could also be applied as a liquid carrier. We have fabricated thermo-reversile gels (gels that are a solution at room temperature and solidify at body temperature), therefore TIPS microspheres with this macromer solution drawn into them, could be injected into the body and bond physically (gel) to each other in situ, maintaining the macroporous structure achieved by the gaps between the spheres themselves. This technique could also be applied to other hydrogel systems which may be photo-curable (the inventors have achieved this in the lab) and with cross-linkable Michael-type conjugate addition hydrogels, thereby creating a method to form in situ scaffolds which can deliver drugs, provide an open-porous structure of predicable porosity and then degrade.

Example 5

Degradation and Local pH Effect of PLGA TIPS Microspheres

This example demonstrates that TIPS microspheres possess advantageous properties compared with solid microspheres.

Materials and Methods

Microspheres (both solid and TIPS microspheres) with a total sample mass of 40 mg were added to 15 ml Falcon tubes (in triplicate) containing 10 ml PBS and incubated for 1, 7, 15, 45, 65, 80, 116 days. 5 ml of PBS was extracted at each time-point for pH measurements and replaced with fresh PBS to 45 days, thereafter, samples were left in capped volumes of PBS. Mass loss of microspheres collected at time-point of degradation was calculated after drying the samples in a vacuum oven. The samples were weighed on an analytical balance. The degraded sample mass relative to the starting mass of the sample was used to calculate % mass loss. Gel permeation chromatography (GPC) analysis was conducted using chloroform as the solvent.

For most samples, a single solution of the sample was prepared by adding 10 mL of solvent to 20 mg of sample (part of the material being taken from each of the three vials or the single vial); for those samples with more than 3% glass filler, the sample mass was increased to allow for the filler content. For most of the '140 Days' samples, less than 20 mg of material was obtained from all five vials and the volume of solvent added was adjusted to give approximately 2 mg/mL with respect to the polymer content. All of the solutions were left overnight to dissolve; were thoroughly mixed and then filtered through a 0.2 μm polyamide membrane. The dissolved samples were subsequently injected into the column (PLgel guard plus 2× mixed bed-B, 30 cm, 10 μm) using chloroform as a solvent with a flow-rate of 1.0 mL/min at a temperature of 30° C.

Results

Mass Loss of TIPS Microspheres

The change in weight average polymer molecular weight (Mw) as a function of degradation time is shown in FIG. 11. The TIPS samples exhibit a quasi-linear drop in molecular weight with increasing degradation time, whereas the solid microspheres exhibit a more rapid increase in degradation rate. The degradation half-lives of the microspheres were calculated according to the method previously described (Wu L and Ding J. In vitro degradation of three-dimensional porous Poly(D,L-lactide-co-glycolide) scaffolds for tissue engineering. Biomaterials 2004 (25) 5821-5820) and are given in Table 2. These data show that the solid microspheres (also of initially the same mass as the TIPS spheres) degraded approximately twice as fast as the TIPS microspheres. The onset of autocatalysis associated with solid PLGA is slowed down in the TIPS microspheres due to the higher surface area available for hydrolysis. The drop in pH and onset of sudden (degradation associated) mass loss occurred at Mn values of ~10000 kg mol$^{-1}$.

TABLE 2

Apparent degradation half-lives for the investigated materials

| Material | Half-life according to Mw |
|---|---|
| PLGA TIPS | 9.31 |
| 3% PG-TIPS | 9.38 |
| 5% PG-TIPS | 9.58 |
| 20% PG-TIPS | 10.60 |
| Solid PLGA microspheres | 5.03 |

Effect of PLGA Microspheres on pH of Local Environment

The pH of the TIPS microspheres remains within the range of physiological pH (6.8-7.4) up to 80 days, whereas the pH of solid microspheres drops below pH 6.8.

At 116 days, the pH falls to ~6.4±0.1 pH units for TIPS spheres but this is much less acidic compared with the solid PLGA microspheres whose pH is below 3.5.

Beyond day 65, the PLGA solid microspheres appear to undergo autocatalysis (a result which will be confirmed by GPC) and begin to meld together, becoming a solid plug at 80 days, whereas the TIPS microspheres remain intact until at least 116 days. By 116 days, the solid spheres have turned into a viscous gel of low molecular weight polymer.

Conclusion

Degradation of the porous TIPS microspheres is delayed compared with solid PLGA microspheres. Degradation appears to occur predominantly via surface mediated hydrolysis due to the higher surface area exposed to the media, whereas the solid microspheres appear to undergo earlier autocatalysis. Similar findings have been found for PDLLA and PLGA foams produced by compression moulding (Wu & Ding, 2004). The example demonstrates the advantageous ability of PLGA TIPS microspheres to maintain the pH of the local environment within a physiological range for a longer period of time compared with solid microspheres, overcoming an existing problem associated with acidic degradation products associated with the use of PLGA and other similar FDA approved polymers.

Example 6

In Vivo Implantation of TIPS Microspheres

This example demonstrates that the TIPS microspheres are well tolerated when implanted in vivo. Tissue infiltrates the microspheres and colonizes the void in the centre of the spheres. Bioactive phases, such as 45S5 bioactive, added to microspheres maintain their ability to stimulate cellular responses.

Materials and Methods

Materials

Poly(D,L-lactide-co-glycolide) (PLGA) (75:25 LA to GA ratio) (Medisorb, Alkermes, USA) was used as the polymeric matrix, dissolved in dimethyl carbonate (DMC) (of >99.9% purity, Sigma Aldrich, UK). 45S5 bioactive glass (kind gift from Schott Glas, Germany) was incorporated as a known stimulant of angiogenesis (R Day. Bioactive glass stimulates the secretion of angiogenic growth factors and angiogenesis in vitro. Tissue Engineering, 2005; 11:768-777).

Porous Bioactive Glass-Loaded Microspheres Produced by Thermally Induced Phase Separation Control PLGA and 45S5 bioactive glass-containing PLGA microspheres were produced using the novel thermally induced phase separation method outlined in the invention. Bioactive glass was loaded at 10% (w/w), with respect to the PLGA by blending the glass particles (~4 µm) with the polymer dissolved in DMC. To ensure adequate mixing of the bioactive glass particulates and homogenous distribution within the polymer solution, all mixtures were sonicated for 15 minutes and subsequently vortexed immediately prior to dripping from from a syringe fitted with a 25G needle, into liquid nitrogen (~40 ml of liquid $N_2$ in a 50 ml Faclon tube) to rapidly induce the phase separation. Each drop of polymer solution was allowed to equilibrate to the liquid nitrogen temperature, demarked by sinking, prior to the addition of further drops to prevent microsphere agglomeration during processing. The frozen spheres were subsequently freeze-dried for 24 h (using an Edwards Freeze-dryer, model EF03 (refrigerated version), West Sussex, UK).

Assessment of Microspheres Implanted Subcutaneously into Wistar Rats

Implantation studies of PLGA TIPS microspheres were performed on inbred adult male Wistar rats (200-250 g) in compliance with the Animals (Scientific Procedures) Act 1986. All the animals were fed on commercial standard pelleted rat diet. Rats were anaesthetized and the TIPS microspheres that had been sterilized by UV irradiation were place into subcutaneous pockets on the ventral aspect of each rat. The pockets were closed with sutures and the rats kept under standard laboratory conditions until 7, 14, 28 and 42 days post-implantation, at which point the tissue containing the microspheres was harvested.

The tissue samples were routinely processed for light microscopy by fixation in 10% buffered formalin and embedded in paraffin-wax. Five micrometer tissue sections were cut to include cross-sections of the embedded microspheres and stained with haematoxylin and eosin.

Results

Microspheres were implanted into the subcutaneous tissue of Wistar rats (FIG. 14a). The microspheres were well tolerated with fibrovascular tissue being clearly visible adjacent to the surface and within the interstices of microspheres at 1 week post implantation (FIG. 14b). Higher power magnification demonstrates cells infiltrating the microspheres and following the pore structure (FIG. 14c).

The microspheres continue to remain well tolerated at longer time points post-implantation (FIG. 15). Fibrovascular tissue continues to remain closely apposed to the microsphere surface.

The void in the centre of microspheres becomes rapidly filled by tissue. Cells are visible in the void at 1 week post implantation (not shown) and are seen to completely fill the void at 2 weeks post-implantation (FIG. 16). The addition of 45S5 bioactive glass to the microspheres, a known stimulus of angiogenesis, results in an increased number of blood vessels in the void (FIGS. 16c and d) compared with control microspheres composed of neat PLGA (FIGS. 16a and b).

Conclusion

TIPS microspheres are well tolerated when implanted in vivo and become infiltrated by cells from the surrounding tissue, which will accelerate integration of the implanted device with tissue when used as a tissue engineering scaffold. Tissue integration is further enhanced by the presence of voids in the microspheres. These will allow the tissue to key into the microspheres providing greater mechanical strength to the implanted device when exposed to forces encountered during tissue movement. Furthermore, the void increases the surface area for tissue exposure to medicaments incorporated into the microspheres.

The structure and size of voids can be modified (or eliminated) by adjusting the processing parameters, e.g. polymer viscosity, dropping method (height above coolant, speed of delivery, manual versus electrostatic delivery, particulate inclusion).

Example 7

TIPS Microspheres and Drug Delivery

This example demonstrates the high encapsulation efficiency and drug release profile of TIPS microspheres using a model drug, metronidazole.

Materials and Methods

Poly(D,L-lactide-co-glycolide) (PLGA) (75:25 LA to GA ratio) (Medisorb, Alkermes, USA) was used as the polymeric matrix, dissolved in dimethyl carbonate (DMC) (of >99.9% purity, Sigma Alrich, UK). Metronidazole (Sigma Aldrich, UK) was incorporated as antibacterial drug effective against anaerobic bacteria within the PLGA, intended as a local delivery device for controlled release of antibiotics.

Porous Drug-Loaded Microspheres Produced by Thermally Induced Phase Separation

Control PLGA and metronidazole-containing PLGA microspheres were produced using the novel thermally induced phase separation method outlined in the invention. Metronidazole was loaded at 1.25% and 2.5% (w/w), with respect to the PLGA by dissolving the polymer and drug in DMC. A stock solution of metronidazole was dissolved in DMC (4.17 mg/ml) and further diluted using DMC to provide final working concentrations of the drug. PLGA was dissolved into the DMC solutions containing the drug at a polymer to solvent ratio of 1:6 w/v (using 2.5 ml of the drug/DMC solutions) for 2 h in 50 ml Falcon tubes, under magnetic stirring. TIPS microspheres were produced by manually dripping the polymer/drug solution from a 1 ml syringe fitted with a 25G needle into liquid nitrogen (~40 ml of liquid $N_2$ in a 50 ml Faclon tube) to rapidly induce the phase separation. Each drop of polymer solution was allowed to equilibrate to the liquid nitrogen temperature, demarked by sinking, prior to the addition of further drops to prevent microsphere agglomeration during processing. The frozen spheres were subsequently freeze-dried for 24 h (using an Edwards Freeze-dryer, model EF03 (refrigerated version), West Sussex, UK).

Preparation of Solid PLGA Drug-Loaded Microspheres

Solid microspheres were prepared for a comparison of the encapsulation efficacy with TIPS microspheres. Solid microspheres containing metronidazole (2.5% w/w drug to polymer) were produced using the oil-in-water emulsion technique (oil-in-oil-in-water). Metronidazole was dissolved in methanol (20.83 mg/ml) prior to combining with PLGA dissolved in DMC at a polymer to solvent ratio of 1:6 w/v (0.833 g PLGA was dissolved in 5 ml DMC for 2 h in a 50 ml Falcon tube, under magnetic stirring). The primary oil-in-oil phase was produced by addition of the methanol and the solution homogenised for 5 minutes at 5000 rpm (using a T8 Ultra-Turrax®, IKE®-WERKE homogeniser, Staufen, Germany). This mixture was poured into a stirred poly(vinyl alcohol) (PVA) solution (200 ml of dH$_2$O with 0.5% w/v PVA). The solution was stirred at 300 rpm. Microspheres were allowed to harden for 4 h prior to washing three times with dH$_2$O, filtering and vacuum drying at room temperature. Spheres were subsequently sieved in the range 300-500 µm diameter.

Immersion Protocol

An immersion process to displace air from within the TIPS microspheres was used to facilitate the exposure of the encapsulated drug with the test fluids. Samples were placed into Falcon® tubes with cell strainers (100 µm nylon membrane, Falcon®) press-fitted into the tubes at the 37.5 ml mark. Immersion fluid was added to the level 45 ml; thereby TIPS microspheres were entrapped by the membrane and below the fluid level. Samples in tubes were placed inside a vacuum desiccator and a vacuum was applied (using an Edwards M3 vacuum pump (Edwards, West Sussex, UK)) with a cold trap (immersed in liquid nitrogen) in-line, to prevent vapors entering the vacuum pump. Samples were kept under vacuum for 40 minutes, during which the fluids out-gassed and air was displaced from the foams (the solutions effervesced vigorously initially). After 40 min (when effervescence was no longer observed) the vacuum desiccator was rapidly let to atmosphere, resulting in immediate sinking of the samples and complete displacement of air. Cell strainers were removed and the lids replaced on the tubes.

Drug Encapsulation Efficacy

TIPS microspheres containing 1.25% (w/w) and 2.5% (w/w) metronidazole, and solid drug-containing microspheres were added to 15 ml Falcon tubes (in triplicate) with a sample mass of 20 mg and dissolved in 1 ml DMC. Subsequently 5 ml dH$_2$O was added and the samples incubated in an agitated platform for 3 days at 37° C. to allow the drug to migrate into the aqueous phase. Samples were then centrifuged and 250 µl taken from each for HPLC analysis.

Drug Release Study

The drug release profile was assessed using the following time points: 1 h, 2 h, 3 h, 4 h, 5 h, 6 h, 20 h, 24 h and 2, 3, 5, 7, 14 and 21 days. Each condition was performed in triplicate. Details of the compositions of the materials tested are given in Table 2. The drug release medium PBS was added (at 37° C.) to the container containing the samples. At each time point 250 µl of media was extracted and replenished with fresh PBS to maintain sink conditions. Samples were frozen prior to HPLC analysis.

TABLE 3

Material composition and metronidazole drug loading.

| | Metronidazole content (% w/w) with respect to PLGA | Media drawn into sphere |
|---|---|---|
| PLGA TIPS microspheres | 1.25 | PBS only |
| PLGA TIPS microspheres | 2.5 | PBS only |
| Solid PLGA microspheres | 2.5 | — |

High Performance Liquid Chromatography (HPLC)

The encapsulation efficacy and the drug release profiles were assessed using HPLC. The chromatographic separation was performed following a modified version of a previously described method (Ramos J R, Howard R D, Pleasant R S, Moll H D, Blodgett D J, Maginin G, Inzana T J. Elution of metronidazole and gentamicin from polymethylmethacrylate beads. *Veterinary Surgery* 2003 (23) 251-261). Each sample was filtered (0.2 µm). 50 µl of each sample was injected through a 30.0×4.6 mm C18 column, with a 3 µm particle size. The solvent used was a mixture of 85% methanol and 15% sodium phosphate buffer (0.01 mol l$^{-1}$, pH 4.0) delivered at a flow rate of 1 ml min$^{-1}$ with UV detection at 313 nm. Standard curves were generated using stock solutions of metronidazole dissolved in PBS (0.13M, pH 7.4) to obtain the following concentrations of metronidazole: 0.05, 0.1, 0.25, 0.5, 1, 5, 10, 25, 50, and 100 µg ml$^{-1}$. The lowest detection of metronidazole was 0.1 µg ml$^{-1}$.

Results

Encapsulation Efficiency

Encapsulation efficiency of a model drug (metronidazole) was investigated for TIPS microspheres containing 1.25% or 2.5% (w/w) and compared with solid microspheres containing 2.5% (w/w) metronidazole produced by oil-in-water processing. The encapsulation efficiency of the solid microspheres is poor (0.53%). This is likely to be caused by the drug leaching out from the micro spheres as they are hardened during the fabrication process (Table 4).

The encapsulation efficiency for the drug-loaded microspheres using the TIPS process is much higher, exceeding 80% for microspheres loaded with 1.25% (w/w) metronidazole (Table 3). Furthermore the amount of metronidazole released from the microspheres containing 2.5% (w/w) is approximately double that released from microspheres containing 1.25% (w/w), indicating a linear relationship between drug loading and drug release from the microspheres.

TABLE 4

Encapsulation efficiency of metronidazole in solid microspheres and TIPS microspheres

| | Metronidazole Detected (µg/ml) | | | Average (±SD) | Average encapsulation efficacy % (±SD) |
|---|---|---|---|---|---|
| Solid PLGA Microspheres + 2.5% (w/w) Metronidazole | 0.51 | 0.54 | 0.54 | 0.53 ± 0.02 | 0.53 ± 0.00 |
| PLGA TIPS Microspheres + 2.5% (w/w) Metronidazole | 158.87 | 167.64 | 156.97 | 161.16 ± 5.69 | 78.36 ± 0.02 |

TABLE 4-continued

Encapsulation efficiency of metronidazole in solid microspheres and TIPS microspheres

| | Metronidazole Detected (µg/ml) | | | Average (±SD) | Average encapsulation efficacy % (±SD) |
|---|---|---|---|---|---|
| PLGA TIPS Microspheres + 1.25% (w/w) Metronidazole | 82.14 | 83.11 | 83.81 | 83.02 ± 0.84 | 82.13 ± 0.02 |

Drug Release

Metronidazole was successfully released from the TIPS microspheres. Both sets of TIPS microspheres incorporating metronidazole (1.25% and 2.5% [w/w]; FIGS. 17 and 18 respectively) exhibit a burst release within the first 24 hours of incubation—a normal feature for drug inclusion in polymers. The release of metronidazole then tails off with increasing time.

Example 8

Production and Companson of Fibrin Microspheres According to the Invention and Collagen Microspheres Using the Method of U.S. Pat. No. 4,837,285

Previous studies have prepared porous microspheres from natural polymers using TIPS processing.

1. Formation of Collagen Beads:

0.1 g of Type III collagen from calf skin (Sigma Aldrich, UK) was suspended in 10 ml of 0.5 M acetic acid (1% weight/volume). The sample was mixed with a magnetic stirrer at high speed for 24 hours. The collagen dispersion was dispensed dropwise from a syringe fitted with a 28 gauge (inner diameter 0.17 mm) needle into liquid nitrogen to rapidly induce freezing. Each drop of collagen was allowed to equilibrate to the liquid nitrogen temperature, demarked by sinking, prior to the addition of further drops to prevent microsphere agglomeration during processing. After allowing the liquid nitrogen to evaporate the frozen spheres were subsequently freeze-dried overnight.

Collagen microspheres were sectioned using a Wilkinson Sword Razor® blade to permit examination of the interior pore structure by scanning electron microscopy (SEM).

2. Fibrin

Fibrin is a naturally occurring product of the physiological blood coagulation cascade. It is produced from the conversion of fibrinogen into fibrin monomers by the serine protease thrombin. Fibrin monomers aggregate to form a weak clot, which is cross-linked by factor XIIIa (activated from factor XIII by thrombin and calcium ions) solidifying the clot. The addition of aprotinin inhibits serine proteases, such as plasmin, that breakdown the fibrin clot via the process of fibrinolysis as wound healing progresses.

Fibrin has been widely used as a tissue sealant, including use as haemostatic agent to control bleeding during surgery or to stop leakage of other types of fluid, such as in fistula repair.

Formation of Fibrin Beads:

0.5 ml of pre-warmed (37° C.) bovine aprotinin solution (3000 Kallidinogenase Inactivator Units/ml; Tisseel Kit Two-Component Fibrin Sealant, Baxter Healthcare Ltd, UK) was added to 0.07 g of pre-warmed (37° C.) Tisseel powder (total protein 50-65 mg of which 37.5 g-57.5 mg is human fibrinogen; Tisseel Kit Two-Component Fibrin Sealant, Baxter Healthcare Ltd, UK). The solution was mixed by swirling and incubated at 37° C. for 10 minutes to allow complete dissolution of the Tisseel powder, indicated by no particles being visibly detectable. 250 µl of distilled $H_2O$ was added to the aprotinin/Tisseel solution.

0.5 ml of calcium chloride (10 µM) was added to 250 IU human thrombin (in 22.5-27.5 mg total protein; Tisseel Kit Two-Component Fibrin Sealant, Baxter Healthcare Ltd, UK). The solution was mixed by swirling to dissolve the powder and incubated at 37° C. for 5 minutes.

Two 2 ml syringes filled with equal volumes of the Tisseel solution and thrombin solution were fitted into a Duploject two-syringe clip (Tisseel Kit Two-Component Fibrin Sealant, Baxter Healthcare Ltd, UK), which enabled the simultaneous delivery of the Tisseel solution and thrombin solution into a joining piece, where quick and thorough mixing of the two solutions occurred resulting in the initiation of the clotting process immediately prior to the drop wise dispensing of the mixed solutions through a 23 gauge needle into a bath of liquid nitrogen. The reduced concentration of calcium chloride (10 µM) used in this example compared with the concentration (40 µM) recommended for use with the Tisseel Kit Two-Component Fibrin Sealant reduces the rate of conversion of fibrinogen into and crosslinkage of fibrin, enabling easier drop wise delivery of the mixed Tisseel solution and thrombin solution into liquid nitrogen. The concentration of other components of the system could also be adjusted (e.g. reducing the thrombin concentration) to affect the rate of conversion and facilitate the fabrication of different sized (particularly smaller) microspheres. Moreover, higher fibrinogen concentrations may produce a mechanical stronger network of fibrin fibrils and thus stronger microspheres. After allowing the liquid nitrogen to evaporate from the spheres in a −70° C. freezer the frozen spheres were subsequently freeze-dried overnight. Fibrin microspheres were sectioned using a Wilkinson Sword® razor blade to permit examination of the interior pore structure by scanning electron microscopy (SEM).

The collagen beads and fibrin microspheres look very different, the collagen beads having irregular pores when compared to the radial pores seen in the fibrin microspheres (see FIGS. 19 and 20). Further, according to U.S. Pat. No. 4,837,285, the collagen beads require crosslinking. The collagen beads absorbed 10 to 50 times their weight of liquid and became swollen, with the bead swelling ratio being inversely proportional to the degree of crosslinking. Microspheres produced in the current study do not require further crosslinking steps since they are stable and also do not expand on fluid uptake, which will ensure the scaffold maintains its porous properties on application. The collagen matrix defining the collagen microsphere structure was in the form of fine fibres having thickness varying from about 5 to 35 microns. The mechanical properties of the collagen microspheres were much lower than that likely to be achieved with microspheres of the invention. Collagen matrix stiffness was found to be 1 kPa to 100 kPa, whereas the matrix mechanical properties of PLGA TIPS foams are ~0.5 to 1 MPa. The formation of channel-like radial pores and a slightly denser skin layer, in conjunction with hard particulate inclusions result in mechanically strong spheres, which are difficult to compress between the fingers. Chitosan is another protein that has been used to fabricate microspheres using TIPS (Roh I J and Kwon I C. Fabrication of a pure porous chitosan bead matrix: influences of phase separation on the microstructure. J. Biomater. Sci. Polym. Ed. 2002 13(7) 769-782., Madihally S V and Matthew H W T. Porous chitosan scaffolds for tissue engineering. Biomaterials 1999 (20) 1133-1142.) Chitosan is an enzymatically degradable polysaccharide, which may lead to degradation varying from patient to patient. Conversely, synthetic poly(α-hydroxyesters) such as PLGA, are advantageous as degradation is predominantly hydrolytic (by water) which will not vary significantly between patients and can be predetermined by polymer composition. As with the collagen microspheres, a major disadvantage with TIPS chitosan microspheres is their poor mechanical resistance properties (6 kPa). Furthermore due to the acidic pH dependent solubility it may be difficult to include basic compounds and bioactive glasses.

TIPS processing using PLGA or other poly(α-hydroxyesters) allows for a variety of different solvents/non-solvents and water with different quench rates to be used which can form different porous structures as their crystallization on freezing differs. Additionally, the viscosity is less of a limiting factor (1 to 30 wt % polymer to solvent ratio can readily be used) and can be adjusted by polymer composition and addition of water to create an emulsion.

Microspheres currently being investigated as scaffolds for tissue engineering are based chiefly on solid microspheres, which present more polymeric material and therefore more degradation products at the site of implantation. The erosion process of TIPS microspheres is more likely to be by surface erosion than autocatalysis, which is commonly encountered with dense poly(α-hydroxyester) systems where water ingresses by diffusion and oligomeric degradation products cannot readily escape, thus causing autocatalysis and the eventual sudden release of acidic degradation products.

Moreover the ability to produce microspheres by TIPS presented here enables microspheres to be produced with control over both the open pore structure (determined by microsphere size) and internal structure, which could be matched to the tissue of interest by adjusting the processing parameters. A network of biologically active microspheres could be applied as a tissue engineering scaffold, or act as a filler material for inaccessible soft and hard tissue repair/augmentation. The current method can also be tailored through polymer composition to be resorbed in days to years.

A major disadvantage of the oil-in-water (o/w) emulsion method is poor encapsulation efficiency of moderately water-soluble and water-insoluble drugs, mainly due to the need to expose the hardening microspheres to an aqueous continuous phase for approximately 4 h to extract the solvent. This causes proteins to agglomerate at the interface between the oil and water phase and the drugs are prone to diffuse out or partition from the dispersed oil phase into the aqueous continuous phase. Improvements to drug encapsulation efficiencies have been made by using oil-in-oil emulsification (Jain R A. The manufacturing techniques of various drug loaded biodegradable poly(lactide-co-glycolide) (PLGA) devices. Biomaterials 2000 (21) 2475-2490.) or by emulsifying the polymer-solvent mix with a small amount of water, prior to addition to the continuous phase. The double (multiple) emulsion process or water-in-oil-in-water (W/O/W) method is best suited to encapsulating water-soluble drugs like peptides, proteins, and vaccines. Drug encapsulation using the TIPS method is far more rapid with the amount of time the drug is exposed to (non-frozen) solvent being minutes rather than hours. The TIPS microspheres described in the current study are suitable to act as scaffold structures that conform to inaccessible body cavities when delivered either dry or in a suitable matrix. Spheres may be used to fill blind tissue pockets and give a predictable porosity once delivered to the site. Spheres may be delivered by catheter alone, by rolling over each other to fill the site and thereby allowing air pockets to be displaced, thereby filling the entire pocket. A further benefit of the technique described herewith is that it eliminates the need for cutting/forming to shape the foams, which can be particularly difficult when hard (glass/ceramic) inclusions are present in the polymer foam.

Moreover, different sized spheres can be used to create graded porosities, which might be of use for example in mimicking the differences between cortical and cancellous bone. By tailoring the pore structure cells may be drawn into open porous network for use as cell carriers. The technique is amenable to the application of gas foaming agents, such as citric acid and sodium bicarbonate, in the polymer mixture prior to freezing to produce a wider variety of pores and more specifically larger pores at the surface for cell infiltration.

Conclusion

The current study presents a novel technique for producing highly porous biodegradable microspheres produced by TIPS that are suitable for localized drug delivery, tissue regeneration/augmentation and tissue engineering. Processing can be adjusted to tailor the pore structure (radial pores or interconnected pores). The inclusion of particulates within the PLGA TIPS microspheres was successfully demonstrated in terms of achieving apparent total encapsulation of the particles and their homogenous distribution within the TIPS microspheres. Proteins can also be incorporated into the PLGA TIPS microspheres. The protein appears to be distributed homogeneously throughout the sphere. The reduction in time when the protein is exposed to a solvent/water interface (approximately 1 minute as compared to ~4 h in conventional oil in water emulsion techniques) is likely to result in less protein denaturation and agglomeration. To further reduce the effect of solvent exposure on the biological activity of proteins they can be added to an aqueous phase to create an emulsion that subsequently undergoes TIPS.

Example 9

Methodology for Automated Manufacture of TIPS Microspheres:

A polymer solution consisting of 8.33% (w/v) poly(lactide-co-glycolide) (PLGA; Purasorb PDLG, PURAC Biochem, Netherlands) in dimethyl carbonate (DMC) (1 g PLGA in 12 ml DMC) was loaded into a 20 ml plastic syringe (Plastipak, Becton Dickinson). The syringe was placed into a syringe pump (Harvard Apparatus pump II) and a length of silicone tubing attached to its nozzle. The other end of the tubing was attached to the vibration unit. The syringe pump provides steady pulsation free flow of polymer solution through the vibrating nozzle, eliminating variability in delivery flow (and subsequent variable microsphere production) that is likely to be encountered with the manual fabrication process. A sapphire nozzle with a 150 μm opening was attached to the vibration unit head. A polyethylene beaker containing 400 ml liquid nitrogen was placed beneath the vibration unit in order to catch the polymer droplets. A range of polymer delivery rates and vibration frequencies and amplitudes were assessed to determine the optimal settings for producing a stable stream of droplets from the unit, which for this polymer solution was found to be 3 ml/minute, 1.80 kHz and 100%, respectively. The polymer droplets froze upon contact with liquid nitrogen in the collecting beaker and remained free from each other. The frozen droplets and a quantity of liquid nitrogen (~30 ml) were placed into 50 ml Falcon tubes and placed into a −80° C. freezer to allow the liquid nitrogen to evaporate. The freeze-drying process was conducted in an identical manner to that previously described in the other examples. After freeze-drying the microspheres were sieved according to the desired size range. The majority of the microspheres fabricated with the parameters described in this example were ~500-700 μm in diameter, but with sieving it is also possible to produce batches of microspheres with defined range sizes, for example 150-300 μm, as shown in FIG. 21. Scanning electron microscopy revealed that the characteristic properties of TIPS microspheres were retained (FIG. 21). By adjusting the solvent to polymer ratio the porosity and inherent mechanical strength of the microspheres can be adjusted. Higher weight/volume % of polymer resulted in lower porosity of the microspheres (FIG. 22).

Example 10

Preparation of TIPS Microspheres Loaded with Growth Factor
Background:
The TIPS fabrication process incorporating the encapsulation unit was used to fabricate microspheres containing basic fibroblast growth factor. The microspheres were assessed in vitro for their ability to release biologically active growth factor.
Experimental:
One ml of dimethyl carbonate (DMC) was added to a vial containing 10 μg of lyophilized recombinant human basic fibroblast growth factor (bFGF) and dispersed by a combination of vortexing and sonication in an ultrasonic water bath. The growth factor solution was added to a polymer solution consisting of 9.09% (w/v) poly(lactide-co-glycolide) (PLGA; Purasorb PDLG, PURAC Biochem, Netherlands) in DMC (1 g PLGA in 11 ml DMC), producing a final polymer concentration of 8.33% (w/v) PLGA. The polymer solution containing growth factor was loaded into a 20 ml plastic syringe (Plastipak, Becton Dickinson) and TIPS microspheres were prepared using the same parameters as outlined above. A batch of control PLGA microspheres were made in an identical manner, with the exception of omitting the lyophilized bFGF. After freeze-drying the microspheres were sieved to produce a size range of 425-500 μm. The microspheres were placed in sterile microfuge tubes and were immersed in tissue culture medium (Eagle's minimum essential medium (EMEM) (Sigma, Poole, UK) supplemented with 10% fetal bovine serum (FBS) (Gibco, Paisley, UK), 2 mM L-glutamine (Sigma), 1 mM sodium pyruvate (Sigma), 1% non-essential amino acids, 50 U/ml penicillin and 50 μg/ml streptomycin (Gibco)) to produce a final concentration of 30 mg microspheres/ml culture medium. Five tubes for each condition were incubated at 37° C. for 24 hours after which the supernatants were collected. One hundred μl of supernatant from bFGF or control microspheres was added to individual wells of a 96-well plate seeded with CCD-18Co myofibroblast cells (seeded 48 hours prior at a density of $1\times10^3$ cells/well) and incubated for 24 hours at 37° C. and 5% $CO_2$. At 24 hours the total number of viable cells was measured using a CellTiter 96® Aqueous Non-Radioactive Cell Proliferation Assay (Promega, UK).
Microspheres containing bFGF stimulated a significant increase in total cell number compared with microspheres containing no bFGF, indicating that growth factors such as bFGF retain their biological activity when incorporated into TIPS microspheres (FIG. 23).

Example 11

Degradation of TIPS and Control (Solid) Microspheres
Long term in vitro degradation studies were conducted in phosphate buffered saline (PBS) at 37° C. on PLGA TIPS microspheres and PLGA TIPS microspheres filled with either 3, 5 or 20 wt. % silver ion doped phosphate based glass and compared to solid PLGA microspheres (control).
All TIPS produced microspheres were prepared as previously described (having sizes of between 1.5-1.7 mm diameter); solid PLGA microspheres were prepared by a traditional oil-in-water technique and sieved to between 300 and 500 μm diameter.
An immersion process was devised to sink and displace air within the initially hydrophobic TIPS microspheres and facilitate the exposure of the encapsulated particles with test fluids. Microspheres were placed into a 50 ml Falcon tube and a modified disposable nylon cell strainer with 70 μm pores was inserted into tube down to the 35 ml mark. Media was added to 45 ml resulting in the microspheres remaining submersed. The open Falcon tube was placed in a vacuum desiccator for 20 minutes to remove air from the microspheres. Upon removal of the vacuum, the air in the microspheres was displaced by the medium and the spheres remained submerged due to the membrane.
Incubation and Degradation of the Microspheres
Microspheres with a sample mass of 40 mg were added to 15 ml Falcon tubes (in triplicate) containing 10 ml PBS and incubated for 1, 7, 15, 45, 65, 80, 116 and 140 days. 5 ml of PBS was extracted at each time-point for pH measurements and replaced with fresh PBS. Mass loss of microspheres collected at time-point of degradation was calculated after drying the samples in a vacuum oven. The samples were weighed on an analytical balance. The degraded sample mass relative to the starting mass of the sample was used to calculate % mass loss. pH measurements were taken at each time-point using a Mettler-Toledo micro pH electrode (Mettler-Toledo Ltd, Leicester, UK). To assess the molecular weight changes with degradation time, Gel permeation chromatography (GPC) analysis was carried by Rapra using chloroform as the solvent. For most samples, a single solution of the sample was prepared by adding 10 mL of solvent to 20 mg of sample (part of the material being taken from each of the three vials or the single vial); for those samples with more than 3% glass filler, the sample mass was increased to allow for the filler content. For most of ultimate time point (140 day) samples, less than 20 mg of material was obtained from all five vials and the volume of solvent added was adjusted to give approximately 2 mg/mL with respect to the polymer content. All of the solutions were left overnight to dissolve; were thoroughly mixed and then filtered through a 0.2 μm polyamide membrane. The dissolved samples were subsequently injected into the column (PLgel guard plus 2× mixed bed-B, 30 cm, 10 μm) using chloroform as a solvent with a flow-rate of 1.0 mL/min at a temperature of 30° C. Morphological and microstructure changes were followed by scanning electron microscopy (SEM) Foams were sectioned using Wilkinson Sword® foil razor blades to enable examination of the interior of samples. Samples were gold sputter coated for 120 s under a current of 20 mA before examination under an accelerating voltage of 20 kV using a JEOL 5610LV SEM (JEOL, USA).
Results
The mass loss profile for the TIPS microspheres as a function of degradation time is shown in FIG. 24. The glass containing spheres show an initial weight loss during the first 15 days of incubation, due to the dissolution and loss of phosphate glass particles; whereas there is little initial loss for the neat PLGA TIPS microspheres. There is a further increase in mass loss observed at the final time point (after a plateau) due to autocatalysis (the onset of rapid degradation), this finding is corroborated by results from GPC, pH profile and SEM (as discussed further below).

Change in number and weight average molecular weight as a function of degradation time are shown in FIGS. 25 and 26. It is evident that solid PLGA microspheres degraded more rapidly than TIPS microspheres. The degradation half-lives of the microspheres (Table 5) were calculated according to the method applied by Wu and Ding [Ref=A] and show that the solid microspheres (also of initially the same mass as the TIPS spheres) degraded approximately twice as fast as the TIPS microspheres. The onset of autocatalysis associated with solid PLGA is slowed down in the TIPS microspheres due to the higher surface area available for hydrolysis. The drop in pH and onset of sudden (degradation associated) mass loss occurred at Mn values of ~10000 kg mol$^{-1}$. The pH of the PBS media used to degrade the spheres in is shown as a function of time in FIG. 27. The pH of aqueous media used to incubate TIPS microspheres remained within the range of physiological pH (6.8-7.4) up to 80 days, whereas the pH of solid microspheres dropped below pH 6.8. At 116 days, the pH fell to ~6.4±0.1 pH units for TIPS microspheres but this was much less acidic compared with the solid PLGA microspheres whose pH was below 3.5. Beyond day 65, the PLGA solid microspheres appeared to undergo autocatalysis confirmed by GPC and begin to meld together, becoming a solid plug at 80 days, whereas the TIPS microspheres remain intact until at least 116 days, in contrast, the solid spheres had turned into a viscous gel of low molecular weight polymer by this time point. The results from this study support the use of TIPS microspheres in chronic wound repair and confirm that the onset of autocatalysis associated with PLGA is retarded due to the higher surface areas available for hydrolysis.

TABLE 5

| Material | Half-life according to Mw |
| --- | --- |
| PLGA TIPS | 9.31 |
| 3% PG-TIPS | 9.38 |
| 5% PG-TIPS | 9.58 |
| 20% PG-TIPS | 10.60 |
| Solid PLGA microspheres | 5.03 |

Degradation of the porous TIPS microspheres is delayed compared with solid PLGA microspheres. Degradation appears to occur predominantly via surface mediated hydrolysis due to the higher surface area exposed to the media, whereas the solid microspheres appear to undergo earlier autocatalysis. Similar findings have been found for PDLLA and PLGA foams produced by compression moulding [REF:A]. The example demonstrates the advantageous ability of PLGA TIPS microspheres to maintain the pH of the local environment within a physiological range for a longer period of time compared with solid microspheres, overcoming an existing problem associated with acidic degradation products associated with the use of PLGA and other similar FDA approved polymers.

Changes in morphology during degradation are described in FIGS. 28 to 34 for the TIPS microspheres. There was little change in the solid microspheres until 80 days, whereupon they became to join together and eventually meld into a viscous polymer plug, in comparison to the TIPS microspheres which evolved spherical pore structures and remained spherical at the end of the study (116 days).

Example 12

Assessment of Porous Polymer/Bioactive Glass-Composite Microspheres for Tissue Regeneration Applications Conformable scaffold materials capable of rapid vascularization and tissue infiltration would be of value in the therapy of inaccessible wounds. Highly porous microspheres of poly (D,L-lactide-co-glycolide) (PLGA) containing bioactive glass (BG) were prepared using a thermally induced phase separation (TIPS) technique, and the bioactivity, in vitro degradation and tissue integration of the microspheres were assessed. Microspheres containing 10% (w/w) BG stimulated a significant increase in VEGF secretion from myofibroblasts consistently over a 10 day period (P<0.01) compared with neat PLGA microspheres. The microspheres degraded steadily in vitro over a 16 week period, with neat PLGA microspheres retaining 82% of their original weight and microspheres containing 10% (w/w) BG retaining 77%. Both types of microsphere followed a similar pattern of size reduction throughout the degradation study, resulting in a 23% and 20% reduction after 16 weeks for neat PLGA microspheres and PLGA microspheres containing 10% (w/w) BG, respectively (p<0.01). Following in vivo implantation into a subcutaneous wound model the TIPS microspheres became rapidly integrated (inter- and intra-spherically) with host tissue, including vascularization of voids inside the microsphere. The unique properties of TIPS microspheres make them ideally suited for regenerative medicine applications where tissue augmentation is required.

Introduction:

In regenerative medicine, bioresorbable polymer scaffolds are used to provide a provisional matrix to guide the growth of cells until complete replacement by host tissue is achieved. Ideally the scaffold structure and its constituent biomaterial should create an optimal environment to integrate and direct tissue regeneration. Conformable scaffolds for guided tissue regeneration are advantageous for applying to inaccessible tissue defects, such as undermining partial- or full-thickness wounds, due to their ability to completely fill the space and be in direct contact with host tissue surfaces, thus facilitating cell infiltration from surrounding tissue. Microspheres are ideal structures for filling inaccessible tissue defects because they can be efficiently packed into asymmetrical spaces. Once implanted microspheres can act as a scaffold, with predictable interstices produced between adjacent spheres guiding tissue infiltration. As with any tissue engineering scaffold, microspheres should have suitable surface properties that are able to direct tissue in-growth, combined with appropriate mechanical and degradation properties. If the scaffold is resorbable it should also be eventually replaced by the host tissue. PLGA is a bioresorbable co-polymer frequently used in tissue engineering applications, with mechanical and degradation properties controlled by adjusting the molecular weight and co-polymer ratio.

Neovascularization is an essential component of wound healing and tissue regeneration, replacing damaged capillaries and re-establishing a supply of oxygen and nutrients. The porosity of a scaffold will dictate the extent of vascular infiltration from host tissue. Targeted delivery of angiogenic agents can be desirable, especially when systemic delivery of the agent could cause damage elsewhere in the body. The introduction of angiogenic growth factors directly into chronic wounds has demonstrated a positive effect on accelerating chronic wound healing. Examples include platelet-derived growth factor, available as a topical gel (Becaplermin) and licensed as an adjunct treatment for full-thickness diabetic ulcers. Enhanced healing and angiogenesis after the introduction of naked plasmid DNA encoding the gene for VEGF has also been achieved in selected patients with ulcers due to vascular occlusive disease. Stimulation of angiogenesis both in vivo and in vitro using BG has also been reported. Incorporation of BG into polymer composites for use as an angiogenic stimulus is advantageous because it avoids the risk of denaturing angiogenic peptides with solvents during scaffold fabrication processes.

A conformable scaffold material capable of rapid vascularization and tissue infiltration to promote healing of chronic deep inaccessible wounds would be of therapeutic value. Novel porous PLGA microspheres containing BG were fabricated using a TIPS process, resulting in highly porous structures. The biological activity and mechanical properties of the microspheres were assessed, along with their ability to integrate with host tissue in a wound model.

Materials and Methods

Preparation of PLGA TIPS Microspheres

PLGA (75:25) (Purasorb® PDLG 7507 0.63 dl/g iv; Purac Biomaterials, Gorinchem, The Netherlands) was dissolved in dimethyl carbonate (DMC) (of >99.9% purity, Sigma Aldrich, UK) under magnetic stirring to produce a polymer weight to solvent volume ratio of 16% (w/v). Neat PLGA TIPS microspheres were prepared by manually delivering the PLGA solution drop-wise from a syringe fitted with a stainless steel nozzle (outer diameter of 0.35 mm and an inner diameter of 0.17 mm) into liquid nitrogen to induce phase separation between the polymer and the crystallizing solvent as rapidly as possible.

PLGA TIPS microspheres containing BG were produced by mixing 45S5 bioactive glass particles (mean particle size of 4 μm and identical in composition to 45S5 Bioglass® (45% $SiO_2$, 24.5% $Na_2O$, 24.5% CaO, 6% $P_2O_5$ wt %); kind gift from Schott Glass, Germany) into the polymer solution to produce 10% w/w BG:PLGA. The solution was sonicated for 20 minutes to disperse glass particle aggregates and mixed at 200 rpm to ensure homogenous distribution of the BG particles in the polymer solution. The 10% w/w solution was further diluted in neat PLGA solution to produce 0.1% and 1% w/w BG in PLGA. Control microspheres consisting of poly(ε-caprolactone) (PCL) were also prepared using the TIPS process. PCL was added to DMC at a ratio of 1:6 w/v, briefly heated in a water bath to 60° C. to assist polymer dissolution and stirred at 200 rpm until it had completely dissolved. BG:PLGA and PCL solutions were dropped into liquid nitrogen as described for the neat PLGA. The frozen microspheres were subsequently transferred in a polythene container to a freeze-dryer (Edwards Modulyo) and sublimated overnight to yield the TIPS microspheres. Microspheres were UV sterilized for 30 minutes prior to use.

In Vitro Assessment of PLGA TIPS Microspheres

VEGF Secretion from Fibroblasts Cultured with Microspheres

Secretion of VEGF and cell viability was assessed using CCD-18Co myofibroblasts derived from human colon (passage 14-20; CRL-1459, American Type Culture Collection, Rockville, Md., USA). Cells were seeded into wells of a 48-well plate at a density of $1\times10^4$ cells/well in 500 μl complete medium (Eagle's minimum essential medium (EMEM) (Sigma, Poole, UK) supplemented with 10% fetal bovine serum (FBS) (Gibco, Paisley, UK), 2 mM L-glutamine (Sigma), 1 mM sodium pyruvate (Sigma), 1% non-essential amino acids, 50 U/ml penicillin and 50 μg/ml streptomycin (Gibco)) and cultured for 4 days.

Prior to co-culturing, the microspheres were immersed in phosphate buffered saline (PBS at 0.13M, pH 7.4) and air within the porous microspheres removed under vacuum. When the vacuum was removed, the microspheres became impregnated with PBS and sank. Thirty-five TIPS microspheres (PLGA, PLGA-BG, or PCL) were transferred into wells containing 500 μl of fresh complete medium in replicates of five. The cells were incubated at 37° C. in 5% $CO_2$-95% humidity. Conditioned medium was collected from each of the wells and replaced with fresh medium at 1 day intervals for a period of 10 days. Collected medium was stored at −70° C. until further analysis. The amount of VEGF secreted from the cells cultured with the different types of microspheres over the 10 day study period was determined using quantitative sandwich enzyme immunoassays (Quantikine® human VEGF; R&D Systems, UK) performed according to the manufacturer's instructions.

Viability of Cells Cultured with PLGA TIPS Microspheres

The viability of cells cultured with the microspheres was assessed after 10 days using the MTT assay. Following collection of supernatant on day 10, fresh medium containing 0.5 mg/ml MTT was added to each well and incubated for 4 hours at 37° C. The resulting formazan product was solubilized with 20% sodium dodecyl sulphate:formamide (1:1) overnight. An aliquot (100 μl) was taken from each well, added to a 96-well plate and the optical density was measured at 570 nm using a microplate reader.

In Vitro Degradation of PLGA TIPS Microspheres

An equal number of dry microspheres (neat or containing 10% (w/w) BG; n=30) were weighed ($W_0$) using a four place digital balance (Mettler Toledo Classic). The microspheres were immersed in PBS and air within the porous microspheres removed under vacuum to ensure the degradation medium permeated the porous structure of the microspheres. The microspheres were placed in 15 ml polypropylene conical tubes containing 10 ml of PBS. The samples were degraded in vitro at 37° C. for up to 16 weeks, in triplicate. The pH of the solution for each degrading sample was measured at weekly intervals, at which point half of the solution was replaced with 5 ml of fresh PBS. After selected degradation times the microspheres were removed from the tubes and weighed ($W_1$) after surface blotting on filter paper to remove excess PBS. The samples were then washed in deionized water and vacuum-dried overnight at room temperature before being weighed ($W_2$) again.

Percentage water absorption (WA) and percentage change in dry weight (WC) of the microspheres were calculated at each time point, using the following equations respectively:

$$WA = (W_1 - W_0) \times \frac{100}{W_0}$$

$$WC = W_2 \times \frac{100}{W_0}$$

Changes to the size of the microspheres during degradation were measured from photomicrographs using image analysis software (Image-Pro Plus). A total of 30 microspheres were measured at each time point and the data presented as the mean value±the standard error of the mean.

Mechanical Testing of PLGA TIPS Microspheres

Changes in the compressive mechanical strength of the PLGA and BG composite TIPS microspheres were determined following 0, 1, 2, 4, and 6 weeks of degradation in PBS. The compressive mechanical property of vacuum-dried microspheres was measured using a Dynamic Mechanical Analyzer (DMA) 7e (PerkinElmer™ Instruments) operated in the static stress scan mode. Tests were performed on individual microspheres at 37° C. using a parallel plate (rectangle) measuring system. Static force was applied from 1 mN to 8000 mN at a rate of 500 mN.min$^{-1}$. The static modulus of the microspheres was determined at 30% strain and plotted as a function of time. Measurements were taken in replicates of four and the mean value±the standard error of the mean plotted.

Structural Morphology of PLGA TIPS Microspheres

Microsphere morphology at each degradation time-point was assessed by scanning electron microscopy (SEM). To examine the interior, microspheres were bisected with a razor blade. Microspheres were mounted onto aluminium stubs via adhesive carbon tabs and sputter coated with gold/palladium alloy for 3 minutes in an argon atmosphere and viewed under SEM (JEOL JSM 550LV operated at 20 kV).

In Vivo Assessment of PLGA TIPS Microspheres

Implantation of PLGA TIPS Microspheres

Implantation studies were performed in compliance with the Animals (Scientific Procedures) Act 1986 on male Wistar rats weighing between 200 and 250 g. All animals were fed on commercial standard pelleted diet. Rats were anaesthetized with Hypnorm 0.4 ml/kg (fentanyl citrate and fluanisone) and diazepam 5 mg/kg. Twenty neat PLGA TIPS microspheres or PLGA TIPS-BG microspheres, sterilized by ultraviolet light, were then placed into subcutaneous pockets created on the ventral aspect of each rat and closed with 3/0 Mersilk® sutures (Ethicon®). Twelve rats per group were kept under standard laboratory conditions until sacrifice at 1, 2, 4 and 6 weeks, when the tissue containing the microspheres was harvested. The resected tissue constructs were placed into 10% buffered formalin and embedded into paraffin-wax for light microscopy.

Histological Assessment of Implanted Microspheres

Five-micrometer tissue sections were cut and stained with haematoxylin and eosin for histological assessment by light microscopy. Neovascularization was assessed in tissue that had infiltrated the voids inside the microspheres. Only clearly delineated voids were selected for assessment. Quantification of blood vessel density was conducted as previously described[7,11]. Briefly, blood vessels were identified by the inclusion of erythrocytes within the blood vessel lumen. The number of blood vessels was quantified using a 25-point Chalkley point eyepiece graticule (Graticules Ltd, Tonbridge Wells, UK) at a magnification of ×250. The graticule was rotated so that the maximum number of graticule points overlaid the blood vessels present in the field of view. The mean of nine Chalkley counts was generated for each type of microsphere implanted and used for statistical analysis. The counting was conducted in a blinded manner regarding the inclusion of BG in the PLGA microspheres.

Data Analysis

Data were expressed as mean±standard error of the indicated number of observations. Statistical comparisons between groups were performed using a two-tailed unpaired t test or ANOVA followed by Dunnet's post hoc test. Differences were considered significant when $P<0.05$.

Results

Microsphere Morphology

Highly porous neat PLGA microspheres and PLGA microspheres containing 10% BG were prepared by solid-liquid phase separation and freeze-drying. The mean diameter of microspheres (n=30), measured by light microscopy and image analysis software was 1.91±0.02 mm and 1.82±0.01 mm for neat and 10% BG microspheres, respectively.

The surfaces of both types of microsphere were similar, consisting of a skin about 2 μm thick containing pores ranging from approximately 1-5 μm, frequently arranged in a chevron-like pattern. Cross-sectioned neat microspheres or microspheres containing 10% BG showed similar highly-ordered interconnected tubular morphologies, ranging from approximately 10-50 μm, with a ladder-like substructure that was orientated in a radial pattern (FIG. 35). Voids were present towards the centre of the microspheres that were connected to the exterior surface via a neck. Pores that passed through the microsphere also opened out into the void. Pore volume in the BG composite microspheres was similar to that of neat microspheres, but the walls of pores contained evenly distributed BG particles.

In Vitro Characterization

Secretion of VEGF from Cells Cultured with Microspheres

The secretion of VEGF from cells cultured with microspheres containing different quantities of BG was assessed over a 10 day period (FIG. 36). Between days 2 and 10, all compositions of PLGA TIPS microspheres stimulated a significant increase in VEGF secretion compared with control cells (p<0.01). Although all of the PLGA microspheres containing BG stimulated a significant increase in VEGF secretion compared with neat PLGA microspheres, only microspheres containing 10% BG produced a significant increase throughout the whole study period (p<0.01). PCL microspheres, included as a negative control, did not stimulate a significant increase in VEGF secretion, yielding values similar to control cells.

Cell Viability

The effect of different microsphere compositions on the number of viable cells was assessed at the end of the 10 day culture period using the MTT assay (FIG. 37). All of the different microspheres tested produced a significant reduction in the number of viable cells compared with control cells (p<0.01), but viability improved with increasing concentrations of BG. Cell viability in response to PLGA microspheres containing 1% and 10% BG was significantly greater compared with neat PLGA microspheres. PCL microspheres led to a significant decrease in cell viability (p<0.01).

Based on results from the in vitro cell culture studies, PLGA TIPS-BG microspheres containing 10% w/w BG were used for the subsequent detailed characterization and in vivo studies.

Degradation of PLGA TIPS Microspheres

The morphology of both types of TIPS microsphere was comparable up to 9 weeks, with the surface porosity and highly ordered interconnected tubular morphology being similar to non-degraded microspheres. At 9 weeks, the skin of the microspheres appeared slightly thicker and the pore widths reduced. At 12 weeks, the tubular morphology and ladder-like substructure was still evident in bisected microspheres, but the wrinkled surface of the microspheres was markedly different, and the small pores arranged in chevron-like pattern had been replaced by a more open porous structure (FIG. 38).

Neat PLGA TIPS microspheres exhibited a mild and gradual weight loss over the 16 week degradation period, retaining 82.24±2.38% of the starting weight after 16 weeks degradation in PBS (FIG. 39). The PLGA TIPS microspheres containing 10% BG followed a similar weight loss profile to neat PLGA microspheres, with 76.99±2.61% of the starting weight retained at 16 weeks.

The reduction of microsphere weight correlated with an overall reduction in size of the microspheres (FIG. 40). Both types of microsphere followed a similar pattern of size reduction throughout the degradation study. After 1 week, the size of neat PLGA microspheres was reduced by 15.94±1.05% and the PLGA microspheres containing 10% BG by 17.12±0.93% compared with their original size (p<0.01 for both). The greatest reduction in size for both types of microsphere occurred after 9 weeks, when the size of microspheres was reduced by 26.01±0.84% and 27.82±0.91% for neat PLGA microspheres and PLGA microspheres containing BG, respectively (p<0.01). After 9 weeks, the size of microspheres gradually increased until the end of the study at 16 weeks, when the sizes were reduced by 22.84±0.96% and 20.13±0.95% for neat PLGA microspheres and PLGA microspheres containing 10% BG, respectively (p<0.01).

The neat PLGA TIPS microspheres showed a greater capacity for water absorption (a weight increase of 285.92±7.92% compared with their dry weight at the beginning of the study) compared with microspheres containing 10% BG (a weight increase of 246.89±7.81% (p<0.05) (FIG. 41). Water absorption by both types of microsphere subsequently decreased from the beginning of study until week 9, when absorption was significantly lower for PLGA microspheres containing 10% BG (down to 58.19±0.87%) compared with neat PLGA microspheres (down to 89.51±1.41%) (p<0.0001). After week 9, water absorption steadily increased again for both types of microsphere, reaching 210.96±19.93% and 143.99±5.30% at the end of the study for neat PLGA microspheres and PLGA microspheres containing 10% BG, respectively (p<0.05).

Changes to the pH of the degradation medium for both types of microsphere are shown in FIG. 42. The pH of the degradation medium was lower than the starting value (7.4) for both types of microspheres at all time points except at 4 weeks, when the pH for both types of microspheres increased to between 7.4-7.5. The pH was generally higher for microspheres containing 10% BG compared with the neat PLGA microspheres. A drop in pH was recorded at weeks 9 weeks for both types of microspheres, after which the pH steadily began to rise before dropping again at 16 weeks.

Compressive strength tests were performed on the microspheres after degradation for 0, 1, 2, 4, and 6 weeks in PBS, corresponding with the in vivo implantation time-points. The modulus was increased for both types of microsphere throughout the degradation study compared with non-degraded microspheres (FIG. 43). After 6 weeks degradation the modulus value of PLGA TIPS microspheres containing 10% BG was significantly higher compared with neat PLGA microspheres at the same time-point (p<0.001).

In Vivo Studies

Histological Assessment of Implanted Microspheres

Microspheres (neat PLGA microspheres or PLGA microspheres containing 10% (w/w) BG) were implanted into subcutaneous pockets created on the ventral aspect of each rat to simulate filling of an undulating wound. At pre-determined time points (1, 2, 4 and 6 weeks) the implants and surrounding tissue were resected and processed for histological analysis (FIG. 44). The microspheres were well tolerated at all time points studied, with no macroscopic differences between the neat PLGA microspheres and those containing 10% BG. After 6 weeks implantation degradation of the microspheres was evident by an obvious reduction in size compared with their size pre-implantation. The microspheres were initially implanted as a multi-layered cluster but the loose skin of the rodent wound model resulted in movement of the microspheres after implantation. This led to the majority of implanted microspheres resting as a single layer rather than maintaining their original cluster formation (FIG. 44). Within 1 week of implantation tissue had infiltrated the interstices between packed microspheres. This consisted mainly of fibrovascular tissue (FIG. 45). There was no apparent difference between neat PLGA microspheres and those containing 10% BG. Higher magnification revealed cells from the surrounding tissue infiltrating the radial tubular macropores originating at the surface of the microspheres (FIG. 45). Fibrovascular tissue remained close to the surface of the microspheres at all time-points studied becoming denser after 6 weeks implantation. At 1 week post-implantation cells were visible in the voids present towards the centre of the microspheres. These were completely filled by fibrovascular tissue after 2 weeks implantation (FIG. 45). Quantitative assessment of the number of blood vessels infiltrating the voids at 2 weeks post-implantation revealed no significant difference between neat PLGA microspheres and those containing 10% BG (FIG. 46).

Discussion

Healing of inaccessible wounds that also require tissue augmentation could be accelerated using conformable scaffolds capable of promoting rapid tissue infiltration. Microspheres are ideal structures for creating porous scaffolds for guided tissue regeneration by readily conforming to the shape of the void to be filled. Microsphere-based scaffolds have been investigated for a wide variety of tissue engineering applications, including bone, cartilage, adipose tissue, and skin. Many of these studies have involved using solid microspheres fabricated using conventional oil-in-water emulsion and solvent extraction/evaporation techniques. Despite providing conformable scaffolds, solid microspheres fail to promote both rapid inter- and intra-spherical tissue integration.

The microspheres described in the current study were produced using TIPS, resulting in highly porous structures. Compared with solid microspheres, TIPS microspheres of an equal size contain less polymer material (up to 90% less). As a consequence much less degradation product is released at the implantation site as the microspheres degrade. This is an important feature, especially with materials such aliphatic polyesters, such as PLGA, that degrade by ester hydrolysis releasing acidic compounds capable of stimulating an inflammatory response at the implant site. Moreover, degradation of solid microspheres is accelerated by autocatalysis. Diffusion of aqueous fluids and their subsequent entrapment in the interior of solid microspheres leads to 'bulk degradation'. If the acidic degradation products cannot readily escape from within the system this leads to more rapid, proton-catalyzed, polymer degradation. In contrast to solid microspheres, the porous structure of TIPS microspheres investigated in the current study makes them more prone to degrade through surface erosion, and allows the acidic degradation products to diffuse away, reducing autocatalysis. The degradation kinetics of the TIPS microspheres was determined in vitro as a function of the hydrolysis time in PBS. A steady decrease in microsphere weight and pH was observed during the 16 week degradation period, rather than a sudden drop in weight and pH typical of autocatalysis. Even though the pH fluctuated during the degradation study it did not drop below 7.0, indicating that such variations are unlikely to cause any significant physiological effect when implanted in vivo. The slightly greater weight loss (~5%) by the PLGA microspheres containing 10% BG compared with the neat PLGA microspheres was probably caused by the dissolution and loss of glass particles from the microspheres. Similar effects on weight loss have been reported in other studies investigating PLGA TIPS foams containing bioactive glass particles.

The exterior of the TIPS microspheres consisted of a skin about 2 μm thick with a semi-smooth surface containing pores (1-5 μm) that were frequently arranged in chevron-like patterns, suggested to be caused by the initial freeze front of the solvent across the droplet surface. As the freeze fronts progress towards the centre of the microsphere, the pore structure becomes more ordered, interconnected, and ladder-like. These structural properties make the microspheres quite rigid, despite their porosity and help to maintain their integrity and thus that of the scaffold as a whole during degradation. The presence of BG did not significantly affect the static modulus of the microspheres, except after 6 weeks degradation. At this time-point there was no significant difference in the diameter or weight remaining between the neat PLGA microspheres and those containing 10% BG. It is possible that the differences observed could be attributed to the formation of hydroxyapatite in the microspheres containing BG.

Water absorption by TIPS microspheres was assessed according to a method previously described for TIPS foams. Although the assessment of water absorption in the current study reflected fluid trapped in the microsphere pores rather than fluid absorption by the poor walls, the results obtained correspond with what was happening to the size of the microspheres, i.e. as the microspheres became reduced in size less fluid was trapped inside.

The neat PLGA TIPS microspheres showed a greater capacity for water absorption compared with microspheres containing 10% BG. Reduced pore volume in TIPS foams containing bioactive glass has previously been reported, therefore the differences in water absorption occurring from the beginning of the degradation study onwards probably result from a smaller volume of bulk fluid being trapped in the pores. The overall smaller values for water absorption in the current study compared with previous studies reflect differences in the porosities of the materials assessed. Previous studies have used higher polymer weight to solvent volume ratios resulting in high porosities (>90%) and therefore a greater capacity to trap water in the pores. Furthermore, the microspheres assessed retained their skin. This is less porous than TIPS foam specimens assessed elsewhere, which have been trimmed to expose their more porous internal structure.

Morphological analysis of the degraded microspheres at 9 weeks revealed thickened skins and shrinkage of the interconnected porous network. These structural changes are likely to have caused expulsion of fluid from the microspheres and could account for the decreased water absorption seen at 9 weeks. Shrinkage of the microspheres, observed both in vitro and in vivo, is likely to have resulted from stresses in the aligned pores radiating from the centre of the microspheres during degradation, similar to that suggested for the shrinkage of cylindrical disks of TIPS PLGA foam scaffolds. Subsequent plasticization due to the presence of water between the polymer chains is likely to have further facilitated their shrinkage in the short term. The surface of the microspheres at 12 weeks was blistered with larger pores resulting from polymer degradation. The blistering effect may have caused the observed increase in microsphere size, which would allow more fluid to enter the microspheres and account for the increase in water absorption seen at 12 weeks and beyond.

Previous studies investigating soft tissue integration with monolithic TIPS polymer foam scaffolds have raised questions regarding the suitability of scaffolds produced using this technique. For example, studies have shown host tissue infiltration into TIPS PLGA foam cubes cut from a monolith to be dependent on the orientation of the pore structure. Also, studies have described tissue in-growth into the pores of TIPS scaffolds being limited by a significant foreign body giant cell response that blocked tissue infiltration into pores smaller than 300 μm. With TIPS microspheres, pores radiate from the centre of the microsphere towards the surface, therefore pore orientation does not need to be controlled for when implanting scaffolds composed of TIPS microspheres and macroporousity is maintained due to the predicatable gaps between spheres. The semi-smooth porous surface of the TIPS microspheres combined with the large void opening onto the surface appears to provide an ideal topology and structure for rapid cell attachment and infiltration into the microspheres. Rapid tissue infiltration into the pores on the surface and the large void inside the microsphere (created by the entrapment of air as the droplet of polymer solution forms during the microsphere fabrication process) occurred within 1 week of implantation. This rapid tissue in-growth is likely to integrate the microspheres into the host tissue, preventing subsequent movement. The infiltration of tissue into the voids inside the microspheres is likely to occur mainly via movement of cells along a neck that extends from the exterior surface of the microsphere. In addition to this, cells may also enter via the pores that open out into the void. The cellularized voids are likely to provide delivery of oxygen, nutrients, and chemotactic signals to cells infiltrating the radial pores from the microsphere surface, thus helping to accelerate fibrovascular tissue infiltration and maintaining intra-spherical tissue viability. Unlike previous studies investigating the in vivo response to TIPS scaffolds, a foreign body giant cell response was not observed with TIPS microspheres.

During wound healing in healthy tissue, angiogenesis results in new capillaries sprouting from pre-existing vessels and organizing into a microvascular network throughout the granulation tissue. VEGF is a specific and critical regulator of angiogenesis, controlling endothelial proliferation, permeability and survival. It has been proposed that certain chronic wounds, where revascularization of damaged tissue is unregulated or insufficient, might benefit from molecular manipulation of growth factors, such as VEGF, to enhance microcirculation and promote tissue infiltration into the wound area. Recent studies have demonstrated the ability of BG to stimulate angiogenesis both in vitro and in vivo. Both neat PLGA TIPS microspheres and those containing BG demonstrated their potential angiogenic properties by stimulating a significant increase in the secretion of VEGF from myofibroblasts in vitro. Quantitative assessment of angiogenesis in tissue surrounding microspheres that had been implanted subcutaneously was not possible due to the dispersal of microsphere cluster at the implant site follow implantation. The extent of intra-spherical vascularization of the microsphere voids was not affected by this, but the ability to count vessels within the voids was dependent upon whether tissue sectioning bisected the microspheres in an appropriate plane. Therefore, it was only possible to quantitatively assess a limited number of microspheres in the current study. A sufficient number of voids for quantitative assessment was visible inside both types of microsphere at 2 weeks, but no significant difference in the number of blood vessels infiltrating the voids existed between microspheres containing 10% BG or control microspheres. The presence of well-vascularized voids inside neat PLGA TIPS microspheres suggests either that the inclusion of an angiogenic stimulus is not necessary to promote neovascularization of the scaffold at the implant site, or that the normal wound healing response in current model, which used 'healthy' animals, masked the angiogenic stimulus initiated by BG. The latter issue could be addressed in future studies by assessing the angiogenic response to TIPS microspheres, with or without BG, in wound models created with animals that have impaired angiogenesis, such as spontaneously hypertensive rats, a well-established experimental model of essential hypertension that has documented impaired angiogenesis compared with normotensive rats.

TIPS microspheres composed of PLGA demonstrated good integration with host tissue. As the spheres degrade, the volume they occupy becomes reduced allowing space for further tissue infiltration into the interstices. Although the inclusion of BG as an angiogenic stimulus was successfully demonstrated in vitro, the inherent structure of the microspheres may also facilitate neovascularization of the microspheres. Rapid vascular integration of the TIPS microspheres with host tissue is likely to ensure improved viability of cells infiltrating the microspheres intra- and inter-spherically. The study demonstrates that PLGA TIPS microspheres integrate well with host tissues and degrade at predictable rates, suggesting they could be readily used as a scaffold/filler material for wounds associated with tissue insufficiency.

Example 13

Assessment of Antimicrobial Microspheres as a Prospective Novel Treatment Targeted Towards the Repair of Perianal Fistulae Methods and Results:

Poly(D,L-lactide-co-glycolide) (PLGA) porous microspheres containing either antibacterial silver-releasing degradable phosphate glass or metronidazole were prepared using thermally-induced phase separation. Ion- and drug-release profiling of the microspheres revealed continued release of silver ions from microspheres filled with silver-doped phosphate glass and high encapsulation efficiency for metronidazole (78% and 82% for microspheres loaded with 2.5% and 1.25% (w/w), respectively). Microbicidal activity was confirmed by growth inhibition of bacterial species (*S. aureus, E. coli* and *B. fragilis*), which characteristically dominate the colonization of perianal fistula tracts. Microspheres containing >3 mol % silver or metronidazole resulted in strong bacterial inhibition/kill against *B. fragilis*; the presence of 1 sphere containing >3 mol % silver had a potent inhibitory effect against all the microbes studied. Microspheres became rapidly integrated with host tissue following subcutaneous implantation into a rodent wound model.

Conclusions:

The study demonstrates a novel scaffold for guided tissue regeneration providing local release of antimicrobial agents sufficient to counter bacterial colonization and warrants further investigation.

Introduction

Perianal fistulae are hollow tracks connecting the anal canal with the perianal skin. Their aetiology includes anorectal abscess caused by bacterial infection, Crohn's disease, trauma, and anal fissure. The pathogenesis of perianal fistulae remains uncertain, but there are two main hypotheses which may not be mutually exclusive. The first suggests fistulae may begin as deep penetrating ulcers in the anus or rectum that extend over time due to faeces being forced into the ulcer with the pressure of defaecation. The second suggests that fistulae occur as a consequence of infection or frank abscess of the anal glands which are at the base of the anal crypts. In both models fistulae appear to form when there is no rapid compensatory fibrogenic response to fill the defect caused. Perianal fistulae are probably perpetuated due to bacterial colonization by the commensals of the lower gastrointestinal tract and/or skin.

Although the options for treating perianal fistulae are continuing to evolve, fistulae rarely heal fully without surgery. In the case of Crohn's disease-associated fistulae there is proven efficacy from the thiopurines and from infliximab and probable benefit from antibiotics, ciclosporin, and tacrolimus. Antimicrobial drugs are the most commonly used agents for Crohn's fistulae, with clinical improvement usually seen after 6-8 weeks, but with early relapse on withdrawal. Surgery for fistulating perianal Crohn's disease can be very successful but may require multiple operative procedures, and can carry the heavy penalty of provoking faecal incontinence.

Tissue cavities, such as fistulae, may be filled with biomaterials to promote healing. Injection of fibrin glue has been proposed as an alternative to the cutting seton and mucosal advancement flap repair of complex fistulae. This procedure is technically straightforward and usually painless, and is considered safe, and free from important morbidity. However, the long-term success rates have been disappointing, being as low as 16% in a recent study. The limited success from fibrin glue may reflect its semi-liquid consistency and the difficulty of filling complex fistulae rather than any adverse biological characteristic, and the glue when set contracts and ceases to fill even those areas previously adequately addressed. In an alternative approach fistula plugs fabricated from porcine small intestine submucosa (Surgisis® Anal Fistula Plug, Cook® Surgical Products) have recently been developed with the aim of plugging the fistula track. Controlled trial data are lacking, and inevitably devices of this nature cannot completely fill the track when there is more than trivial tortuosity or branching Moreover, it is uncertain whether the collagen material used in the preparation of these devices is fully compatible in fistulae associated with increased matrix metalloproteinase activity.

There is clearly a continuing need for novel treatment strategies for perianal fistulae, but better filling agents and approaches to their use might be expected to bear fruit. It is proposed that rates and speed of healing could be improved through adjustment of the physical properties of filler materials, combining this with bioactive phases which treat the underlying disease and/or lessen the incidence of infections related to implanted materials.

The aim of the current study was to develop and assess porous poly(D,L-lactide-co-glycolide) (PLGA) microspheres containing either metronidazole or silver-doped phosphate glass particles for use as a potential alternative filler/anti-microbial strategy for the treatment of fistulae. Recent work has demonstrated that the inventors' technique allows the formation of well-formed highly porous microspheres. Moreover, the pore structure of the spheres can be tailored by adjusting the processing parameters, and it is possible to incorporate inorganic bioactive phases (e.g. bioactive glasses) and drugs with high encapsulation efficacies. The release of ions and drugs, and the anti-microbial activity of the microspheres were assessed in vitro, and tissue integration of implanted microspheres was studied using an in vivo animal model to gauge the likely tissue response in a human fistula tract.

Materials and Methods

Porous antimicrobial and biodegradable microspheres were produced from PLGA (75:25) as a matrix using the novel processing technique previously described. The microspheres were processed to include either phosphate-based glass particulates containing different amounts of silver, or metronidazole (Sigma Aldrich). Neat PLGA spheres were used as a control. Briefly, the polymer was dissolved in a suitable organic solvent (dimethyl carbonate) and the bioactive phase either dissolved or mixed into the solution. The solution was then dripped into liquid nitrogen via a 23 G hypodermic needle, whereupon frozen spheres were formed ranging in size from 1-1.7 mm. The porous microspheres were obtained after freeze-drying.

Preparation of Microspheres Containing Phosphate-Based Glass Doped with Silver

The composition of the phosphate glass investigated had a fixed phosphate content of 50 mol %, with a fixed CaO content of 30 mol %, with $Na_2O$ substituted with silver to either 0, 1, 3, or 5 mol %. The glass particle size was <20 μm. The composition of the phosphate glass-containing microspheres evaluated in this study is given in Table 6.

Microspheres were loaded with metronidazole at 1.25% and 2.5% (w/w), with respect to the PLGA by dissolving the polymer and drug in the organic solvent. A stock solution of metronidazole was dissolved in the organic solvent (4.17 mg/ml) and further diluted in solvent to provide the final working concentrations of the drug. PLGA was then dissolved into the solvent solutions containing the drug at a polymer to solvent ratio of 1:6 w/v (using 2.5 ml of the drug/solvent solutions) for 2 h in 50 ml Falcon tubes, under magnetic stirring. Microspheres were then produced as described above.

Solid PLGA microspheres loaded with metronidazole were prepared for a comparison of the encapsulation efficiency with that of porous microspheres. Solid microspheres containing metronidazole (2.5% w/w drug to polymer) were produced using an oil-in-oil-in-water emulsion technique.

Microspheres (40 mg) were immersed in 5 ml phosphate buffered saline (PBS at 0.13M, pH 7.4) and air within the porous structures removed under vacuum to facilitate exposure of the encapsulated particles/drug to the test fluids. The drug release profile for metronidazole was assessed hourly to 6 h, then at 20 h, 24 h and selected time points to 21 days. Each condition was studied in triplicate. At each time point 250 µl of media were extracted and replenished with fresh PBS to maintain sink conditions. Samples were frozen prior to high-performance liquid chromatography (HPLC).

To measure encapsulation efficacy, microspheres (20 mg) containing metronidazole were added to 15 ml Falcon tubes (in triplicate) and dissolved in 1 ml of organic solvent. Subsequently, 5 ml de-ionized water was added and the samples incubated using an agitated platform for 3 days at 37° C. to allow the drug to diffuse into the aqueous phase. Samples were then centrifuged and 250 µl taken for HPLC analysis.

HPLC was performed following a modified version of a previously described method. Each sample was filtered (0.2 µm) and 50 µl of each sample was injected through a 30.0×4.6 mm C18 column, with a 3 µm particle size. The solvent used was a mixture of 85% methanol and 15% sodium phosphate buffer (0.01 mol $l^{-1}$, pH 4.0) delivered at a flow rate of 1 ml $min^{-1}$ with UV detection at 313 nm. Standard curves were generated using stock solutions of metronidazole dissolved in PBS to obtain the following concentrations of metronidazole: 0.1, 0.5, 10, 50, and 100 µg $ml^{-1}$.

The release profile of silver ions over time from the microspheres containing silver-doped phosphate glasses was determined by inductively coupled plasma optical emission spectroscopy. Ten microspheres from each concentration of silver containing phosphate glass were immersed as described above and placed into individual wells of a 48-well tissue culture plate in replicates of three, and a further 420 µl of cell culture medium added. The release profiles from the spheres were assessed after incubation at 37° C. for 30 minutes, 3 h, 6 h, 18 h, then at 2, 7, 12, 16 and 21 days. Media were exchanged at all time points beyond 2 days better to represent the in vivo environment.

Inhibition of microbial growth by microspheres containing silver-doped phosphate glasses or metronidazole was assessed using bacterial cultures pertinent to colonization of perianal fistulae. Cultures obtained from the National Collection of Type Cultures (Health Protection Agency, Colindale, UK) were *Staphylococcus aureus* (NCTC6571), *Escherichia coli* (NCTC10418), *Bacteroides fragilis* (NCTC9343). The three organisms under investigation were inoculated into 25 ml of Nutrient Broth (Oxoid Ltd, Basingstoke, UK) and incubated overnight at 37° C. with continuous agitation in an orbital shaker (Stuart Scientific, UK). The agitation speed was set at 200 rpm.

Bactericidal inhibition studies were conducted after sinking the microspheres aseptically in Nutrient Broth using the vacuum technique described above. Various numbers of microspheres (from 1 to 20 spheres, in replicates of 5) were added to the wells of a 96 well tissue culture plate containing 100 µl of Nutrient Broth. The wells were inoculated with $10^4$ bacteria per well. Cultures were left overnight at 37° C. in a humidified incubator with 5% $CO_2$. The turbidity of the media was measured using a UV/Visible Spectrophotometer after the culture period to determine the influence of the materials on bacterial inhibition. The effectiveness of metronidazole-containing spheres was tested solely against *B. fragilis* given the expected intrinsic resistance of *S. aureus* and *E. coli* to this antibiotic. Analysis of the optical density readings obtained in the presence of differing numbers of spheres was carried out using the Mann-Whitney U-test. Data were analysed using SPSS software and the 5% level of statistical significance was used throughout these analyses. The statistical test was performed to determine significant difference in optical density/number spheres versus one sphere of the same material, inferring bacterial inhibition or kill.

Implantation studies were performed in compliance with the Animals (Scientific Procedures) Act 1986 on male Wistar rats weighing 200-250 g. All the animals were fed on commercial standard pelleted diet. Rats were anaesthetized, and 24 neat PLGA microspheres or PLGA microspheres filled with 5 wt. % phosphate based glass doped with 3 mol % Ag, sterilized by ultraviolet light, were placed into subcutaneous pockets measuring approximately 15 $mm^2$ created on the ventral aspect of each rat by blunt dissection and closed with 3/0 Mersilk® sutures (Ethicon®). Rats were then kept under standard laboratory conditions until sacrifice at 7, 14, 28 and 42 days, when the tissue containing the microspheres was harvested. The resected tissue constructs were placed into 10% buffered formalin and embedded into paraffin-wax for light microscopy.

Results

The microspheres selected for the study measured ~1.5 mm, and had a good interconnected porous structure, with the presence of tubular macropores radiating towards the centre of the spheres (FIG. 47a). As a result of the microsphere fabrication process voids were present in the centre of the material (extending to the exterior) due to the polymer solution droplet formation and its subsequent freezing. The spheres had sufficient mechanical integrity to withstand handling. The phosphate glass particles were uniformly incorporated within the polymer walls of the microspheres (FIG. 47b).

A continued dissolution of silver from the PLGA microspheres containing 20 wt. % silver-doped phosphate glass was apparent (FIG. 48). Silver concentration steadily increased to ~10 ppm at day 21, after which moderate drop off was detected, whereas silver ion dissolution for microspheres containing the lowest silver concentration (1 mol. %) increased steadily to a maximum of 1.7 ppm at 48 h. The release profile of silver ions correlates with silver content in the starting material.

The encapsulation efficiency using the thermally-induced phase separation process was 78% and 82% for microspheres loaded with 2.5% and 1.25% (w/w) metronidazole, respectively, compared with 0.53% for solid microspheres processed using traditional oil-in-water techniques (p<0.0001; unpaired t-test). Metronidazole was successfully released from the microspheres (FIG. 49). Both porous and solid microspheres incorporating metronidazole exhibited a burst release within the first 24 hours of incubation.

The release of silver ions from microspheres filled with silver-doped phosphate glass resulted in marked bacterial inhibition/kill, (Tables 7 a-c), compared to neat PLGA microspheres or microspheres filled with phosphate glass containing no silver. Microspheres containing 3 mol % silver provided a potent antibacterial effect against *S. aureus, E. coli* and *B. fragilis*. This concentration was subsequently used for the in vivo implantation studies. The metronidazole containing spheres also exhibited a significant inhibition of *B. fragilis*. Five or more neat PLGA microspheres and microspheres containing 20 wt % phosphate glass were needed to inhibit bacterial growth; however one sphere of any of the silver or metronidazole containing spheres resulted in near zero optical densities, indicating strong bacterial inhibition/kill.

The rats did not appear to suffer any untoward distress or discomfort from the implants during the study period. After sacrifice the implants were resected and processed for histological analysis (FIG. 50a). The microspheres appeared to have been well tolerated at the tissue level at all times, with no apparent differences between the neat PLGA microspheres and those filled with phosphate-based glass. After 6 weeks implantation degradation of the polymer microspheres was visible, with the microspheres being reduced in size compared with their pre-implantation state. Although the microspheres were implanted as a cluster, the nature of the wound pocket and the loose skin of the rodent model resulted in movement of the microspheres subsequent to implantation. The majority of implanted microspheres rested as a single layer rather than maintaining their original formation as a cluster (FIG. 50b). Histological analysis of the implants revealed tissue infiltrating the packed microsphere interstices (FIG. 51). Qualitative assessment of cellular infiltration between the implanted microspheres revealed fibrovascular tissue adjacent to the surface and within the interstices of microspheres at 1 week post implantation, with no apparent difference between the different microsphere types (FIGS. 51a and 51b). Higher power magnification demonstrated cells from the surrounding tissue infiltrating the microspheres, apparently guided by the radial tubular macropores orientated towards the centre of the spheres (FIG. 51c). The void present toward the centre of each microsphere became rapidly filled by tissue. Cells were visible in the void in samples studied at 1 week post implantation, and were found to fill the void completely from 2 weeks' implantation and onwards (FIGS. 51d and 51e). Fibrovascular tissue remained closely apposed to the surface of the microspheres at all time-points studied. After 6 weeks' implantation the fibrovascular tissue surrounding the microspheres appeared to have become contracted and denser (FIGS. 51f and 51g).

Discussion

Long-term closure rates of perianal fistulae after the use of fibrin glue have been disappointing, with success rates generally decreasing with length of follow-up. It has been suggested that some of the biological properties of fibrin glue may contribute to the low success rates. For example, although fibrin glue supports the proliferation of fibroblasts and epithelial cells it does not allow fibroblast infiltration and may also reduce deposition of ECM proteins. Furthermore, the fibrin glue is easily extruded through the fistula tract when subjected to high pressures, for example during coughing or straining and the majority of it is resorbed within five to ten days after instillation, which does not allow sufficient time for tissue regeneration required for a compensatory fibrogenic response to fill the defect.

The current study describes a novel filler biomaterial that is targeted for repair of perianal fistulae that facilitates fibrogenesis and has properties that could prevent sepsis during the healing process. Microspheres have properties ideally suited to filling fistulae since they can be efficiently packed into asymmetrical voids, such as the secondary side tracks often found in difficult fistulae. The subcutaneous wound studied limits inference on the applicability of the device in a fistula setting. However, the infiltration of the tissue into the defined gaps created by the sphere network is promising. Whilst some plugging devices are currently used (Surgisis® Anal Fistula Plug, Cook® Surgical Products), the device we propose based on microspheres may be more effective at filling complex tracts. Although the current study used ~1.5 mm microspheres, our subsequent work has demonstrated that it is possible to produce spheres as small as 10 µm (data not shown). The in vivo implantation study was designed to assess the integration of spheres with host tissue, rather than simulate an irregular fistula tract. The present results confirm that once implanted the spheres act as a scaffold, and that the predictable interstices produced between adjacent spheres appear to guide tissue infiltration.

The porous structure of the microspheres also imparts a roughened surface topology, known to improve cell attachment, facilitating cell infiltration within the spheres, which was clearly visible at 1 week post-implantation, and further tissue integration of the device with host tissue. This attribute will hopefully reduce the risk of extrusion of microspheres from the fistula track. Filling a fistula with biodegradable microspheres will provide a temporary structure that initially reduces the volume of new tissue required. It is proposed that the device developed could be injected into the fistula tract and that the internal opening of the fistula be closed surgically using, for example an advancement flap. It is clear that further work must be undertaken to assess the effectiveness of the device in a more realistic fistula model. Microspheres degrade at a predictable rate, which allows them to be replaced by regenerating tissue, unlike the collagen fistula plug, which may be susceptible to unpredictable degradation due to MMPs associated with fistula formation. Porous microspheres are advantageous over solid microspheres as they release fewer acidic degradation products. As the porous spheres degrade the volume they occupy is reduced allowing space for further fibrous tissue infiltration into the interstices. Elimination of acute sepsis is essential for the successful management of anal fistulae. Although it is reported that few pathologic organisms are actually detectable in non-filled fistula tracks, bacterial infections are a significant problem spontaneously, and more so in association with biomaterial implants. This may be particularly problematic with biomaterials implanted into perianal fistulae, where tracks may communicate between the gastrointestinal tract and skin providing a route for colonization by gut or skin flora. The antimicrobial activity of silver and of metronidazle shown in the present study is well documented in other contexts.

Microspheres loaded with silver ion-releasing degradable phosphate glass appeared to be well tolerated when implanted in vivo, becoming infiltrated by cells from the surrounding tissue in the same way as neat control microspheres.

Conclusion

The results in this study suggest that porous microspheres with the capacity to locally deliver drugs to the implant site could be effective in the perianal fistula repair setting. Whilst the study was limited to the filling of non-complex closed subcutaneous defects the device might be a candidate for further testing in the clinical context. We take advantage of the well known fact that the inherent packing efficiencies of microspheres provide the ability to pack complex shapes, which should enable them to effectively fill fistula tracks, where they could provide targeted delivery of drugs directly to sites of disease. The microspheres provide a scaffold for guided tissue regeneration whilst their controlled biodegradation allows sufficient time for tissue regeneration. Further pre-clinical studies are warranted to explore the therapeutic potential of microspheres towards perianal fistulae healing.

TABLE 6

Summary of material compositions evaluated containing glasses. The wt. % of phosphate glass indicated is relative to the mass of PLGA.

| Material type | Silver content (mol %) |
|---|---|
| PLGA + 20 wt. % Phosphate glass | 0 |
| PLGA + 3 wt. % Phosphate glass | 1 |
| PLGA + 5 wt. % Phosphate glass | 3 |
| PLGA + 20 wt. % Phosphate glass | 5 |

TABLE 7

Bacterial inhibition according to the optical density (OD).

| Number of spheres | 1 | 2 | 3 | 5 |
|---|---|---|---|---|
| (a) *E. coli.* | | | | |
| PLGA | 1.129 ± 0.035 | 1.046 ± 0.049 | 1.025 ± 0.107 | 0.961* ± 0.06 |
| PLGA 20 wt. % PG | 0.801 ± 0.131 | 0.877 ± 0.178 | 0.943 ± 0.055 | 0.856 ± 0.094 |
| PLGA 5 wt. % PG 3% silver | 0.000 ± 0.002 | 0.004 ± 0.005 | 0.004 ± 0.003 | 0.018 ± 0.022 |
| PLGA 20 wt. % PG 5% silver | 0.001 ± 0.001 | 0.006 ± 0.006 | 0.015 ± 0.003 | 0.018 ± 0.005 |
| (b) *S. aureus.* | | | | |
| PLGA | 1.033 ± 0.066 | 1.013 ± 0.028 | 0.964 ± 0.149 | 0.746* ± 0.029 |
| PLGA 20 wt. % PG | 0.944 ± 0.071 | 0.934 ± 0.078 | 0.866 ± 0.120 | 0.600* ± 0.110 |
| PLGA 5 wt. % PG 3% silver | 0.492 ± 0.288 | 0.010$^{1*}$ ± 0.005 | 0.012* ± 0.013 | 0.003* ± 0.022 |
| PLGA 20 wt. % PG 5% silver | 0.001 ± 0.001 | 0.006 ± 0.006 | 0.015 ± 0.003 | 0.018 ± 0.005 |
| (c) *B. fragilis* | | | | |
| PLGA | 0.132 ± 0.023 | 0.122 ± 0.004 | 0.128 ± 0.029 | 0.089* ± 0.008 |
| PLGA 20 wt. % PG | 0.069 ± 0.004 | 0.062 ± 0.01 | 0.042 ± 0.028 | 0.035* ± 0.01 |
| PLGA 5 wt. % PG 3% silver | 0.000 ± 0.001 | 0.000 ± 0.003 | 0.000 ± 0.002 | 0.000 ± 0.002 |
| PLGA 20 wt. % PG 5% silver | 0.000 ± 0.001 | 0.000 ± 0.003 | 0.001 ± 0.005 | 0.001 ± 0.004 |
| PLGA + 2.5% (w/w) Metronidazole | 0.001 ± 0.012 | 0.000 ± 0.003 | 0.000 ± 0.004 | 0.000 ± 0.002 |

| Number of spheres | 8 | 12 | 15 | 20 |
|---|---|---|---|---|
| (a) *E. coli.* | | | | |
| PLGA | 0.984* ± 0.088 | 0.927* ± 0.07 | 0.894* ± 0.026 | 1.042 ± 0.06 |
| PLGA 20 wt. % PG | 0.981 ± 0.147 | 0.474* ± 0.094 | 0.157* ± 0.18 | 0.000* ± 0.003 |
| PLGA 5 wt. % PG 3% silver | 0.004 ± 0.001 | 0.011 ± 0.006 | 0.012 ± 0.004 | 0.011 ± 0.004 |
| PLGA 20 wt. % PG 5% silver | 0.013 ± 0.004 | 0.006 ± 0.006 | 0.006 ± 0.007 | 0.005 ± 0.007 |
| (b) *S. aureus.* | | | | |
| PLGA | 0.817* ± 0.079 | 0.702* ± 0.026 | 0.669* ± 0.025 | 0.732* ± 0.103 |
| PLGA 20 wt. % PG | 0.454* ± 0.057 | 0.266* ± 0.028 | 0.147* ± 0.052 | 0.022* ± 0.021 |
| PLGA 5 wt. % PG 3% silver | 0.003* ± 0.001 | 0.005* ± 0.004 | 0.008* ± 0.004 | 0.013* |
| PLGA 20 wt. % PG 5% silver | 0.013 ± 0.004 | | | |
| (c) *B. fragilis* | | | | |
| PLGA | 0.082* ± 0.019 | 0.053* ± 0.019 | 0.037* ± 0.009 | 0.041* ± 0.022 |
| PLGA 20 wt. % PG | 0.002* ± 0.002 | 0.000* ± 0.004 | 0.02* ± 0.055 | 0.000* ± 0.003 |
| PLGA 5 wt. % PG 3% silver | 0.001 ± 0.002 | 0.004 ± 0.004 | 0.004 ± 0.005 | 0.002 ± 0 |
| PLGA 20 wt. % PG 5% silver | 0.000 ± 0.003 | 0.000 ± 0.001 | 0.000 ± 0.003 | 0.000 ± 0.003 |
| PLGA + 2.5% (w/w) Metronidazole | 0.000 ± 0.002 | | | |

*denotes a significant ($p < 0.05$) reduction in the OD compared to the value obtained with 1 sphere.

The invention claimed is:

1. A microsphere produced by thermally induced phase separation, said microsphere having a single void comprising a neck connecting the void to the exterior surface of the microsphere, wherein the ratio of diameters of the neck to the microsphere is from 1:1.9 to 1:18.9, and wherein the microsphere further comprises radial pores.

2. A method of treating a wound, comprising filling the wound with microspheres according to claim 1.

3. The microsphere of claim 1 wherein the void is located toward the center of the microsphere.

4. A microsphere according to claim 1 wherein the microsphere is about 10 to 2000 µm diameter.

5. A microsphere according to claim 1 wherein the microsphere is less than 300 µm in diameter.

6. A microsphere according to claim 1 wherein the pores are between 1 and 100 µm in diameter.

7. A microsphere according to claim 1 wherein the microsphere includes a skin region at its surface.

8. A microsphere according to claim 1 wherein the microsphere is skinless.

9. A microsphere according to claim 1 wherein the microsphere is produced from a polymer.

10. A microsphere according to claim 9 wherein the polymer is pharmaceutically acceptable.

11. A microsphere according to claim 9 wherein the polymer is degradable.

12. A microsphere according to claim 9 wherein the polymer is non-degradable.

13. A microsphere according to claim 9 wherein the polymer is synthetic.

14. A microsphere according to claim 9 wherein the polymer is non-synthetic.

15. A microsphere according to claim 9 wherein the polymer is a combination of a synthetic polymer and a non-synthetic polymer.

16. A microsphere according to claim 9 wherein the polymer is a copolymer.

17. A microsphere according to claim 13, wherein the polymer is selected from the group consisting of a poly($\alpha$-hydroxyester), polyanhydride, polyorthoester, polyphosphazine, polypropylene fumarate, poly propylene-fumarate-co-ethylene glycol), polyethylene oxide, polyhydroxybutyrate (PHB), polyhydroxyvalerate (PHV), a co-polymer of PHB and PHV, and a poly($\alpha$-hydroxyester)-co-PEG copolymer.

18. A microsphere according to claim 14, wherein the polymer is fibrin.

19. A microsphere according to claim 1 wherein the microsphere contains an encapsulated additive.

20. A microsphere according to claim 19 wherein the additive is selected from the group consisting of: a glass which contains $NaH_2PO_4$, $CaCO_3$, $P_2O_5$, or $Ag_2SO_4$, a glass-ceramic which contains $NaH_2PO_4$, $CaCO_3$, $P_2O_5$, or $Ag_2SO_4$, a ceramic which contains $NaH_2PO_4$, $CaCO_3$, $P_2O_5$, or $Ag_2SO_4$, proteins, peptides, antibodies, antibody fragments; nucleic acids; and therapeutic agents.

21. The microsphere of claim 1 further comprising an interconnected tubular morphology oriented in a radial pattern toward the void.

22. The microsphere of claim 7 wherein the skin is about 2 $\mu$m thick and comprises pores arranged in a chevron-like pattern.

23. A microsphere produced by thermally induced phase separation, said microsphere having a single void comprising a neck connecting the void to the exterior surface of the microsphere, wherein the neck has a diameter of from 75 to 250 $\mu$m.

24. A method of treating a wound, comprising filling the wound with microspheres according to claim 23.

* * * * *